United States Patent
Cochrane et al.

(10) Patent No.: US 11,413,297 B2
(45) Date of Patent: Aug. 16, 2022

(54) THERAPIES FOR TREATING AND PREVENTING CHRONIC RHINOSINUSITIS

(71) Applicants: Avanti Polar Lipids, LLC, Alabaster, AL (US); THE SCRIPPS RESEARCH INSTITUTE, La Jolla, CA (US)

(72) Inventors: Charles G. Cochrane, La Jolla, CA (US); Ronald A. Simon, La Jolla, CA (US); Stephen W. Burgess, Alabaster, AL (US); Walter A. Shaw, Alabaster, AL (US)

(73) Assignees: AVANTI POLAR LIPIDS, LLC, Alabaster, AL (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/649,534

(22) PCT Filed: Sep. 21, 2018

(86) PCT No.: PCT/US2018/052269
§ 371 (c)(1),
(2) Date: Mar. 20, 2020

(87) PCT Pub. No.: WO2019/060761
PCT Pub. Date: Mar. 28, 2019

(65) Prior Publication Data
US 2020/0306274 A1    Oct. 1, 2020

Related U.S. Application Data

(60) Provisional application No. 62/561,313, filed on Sep. 21, 2017.

(51) Int. Cl.
*A61K 31/6615* (2006.01)
*A61K 31/7036* (2006.01)
*A61K 9/00* (2006.01)
*A61K 45/06* (2006.01)

(52) U.S. Cl.
CPC ...... *A61K 31/6615* (2013.01); *A61K 31/7036* (2013.01); *A61K 9/0075* (2013.01); *A61K 9/0078* (2013.01); *A61K 45/06* (2013.01)

(58) Field of Classification Search
CPC .................................................. A61K 31/6615
USPC ......................................................... 514/114
See application file for complete search history.

(56) References Cited

U.S. PATENT DOCUMENTS

| 6,165,997 A | 12/2000 | Cohen |
| 2003/0139356 A1 | 7/2003 | Persing |
| 2012/0071442 A1 | 3/2012 | Yedgar |
| 2014/0134210 A1 | 5/2014 | Chuong |
| 2017/0173165 A1 | 6/2017 | Stremmel |
| 2017/0232029 A1 | 8/2017 | Deboeck |

FOREIGN PATENT DOCUMENTS

| EP | 2740479 | 6/2014 |
| WO | WO1999/26632 A1 | 6/1999 |
| WO | 2007071658 | 6/2007 |
| WO | 2013135571 | 9/2013 |
| WO | WO2016/133863 | 8/2016 |

OTHER PUBLICATIONS

Young, Lee, International Search Report and Written Opinion, PCT/US2018/52269, dated Dec. 6, 2018.
Dong Dong, et al. Distribution and Inhibition of Liposomes on *Staphyulococcus aureus* and Pseudomonas aeruginosa Biofilm, PLOS ONE, 10(6): 1-16 (Jun. 30, 2015).

*Primary Examiner* — Taofiq A Solola
(74) *Attorney, Agent, or Firm* — RatnerPrestia

(57) ABSTRACT

The invention provides compositions and methods for disrupting preformed bacterial biofilm or preventing formation of bacterial biofilm. Also provided in the invention are methods and compositions for treating and preventing chronic rhinosinusitis. Such compositions and methods utilize one or more antibiotic compounds in combination with at least one phospholipid compound described herein.

28 Claims, 37 Drawing Sheets

07:0-PC (DHPC)

MAPCHO-12

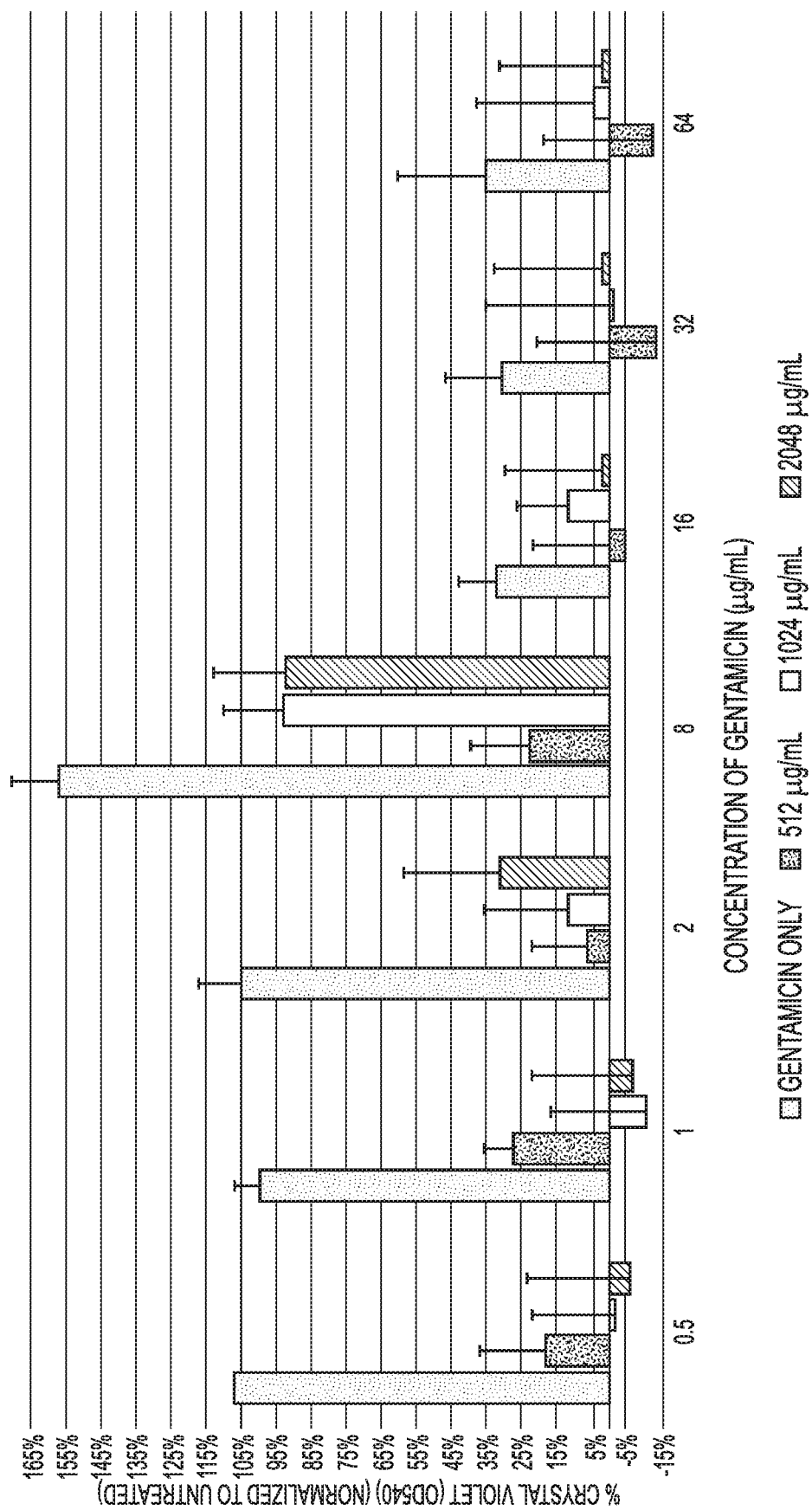

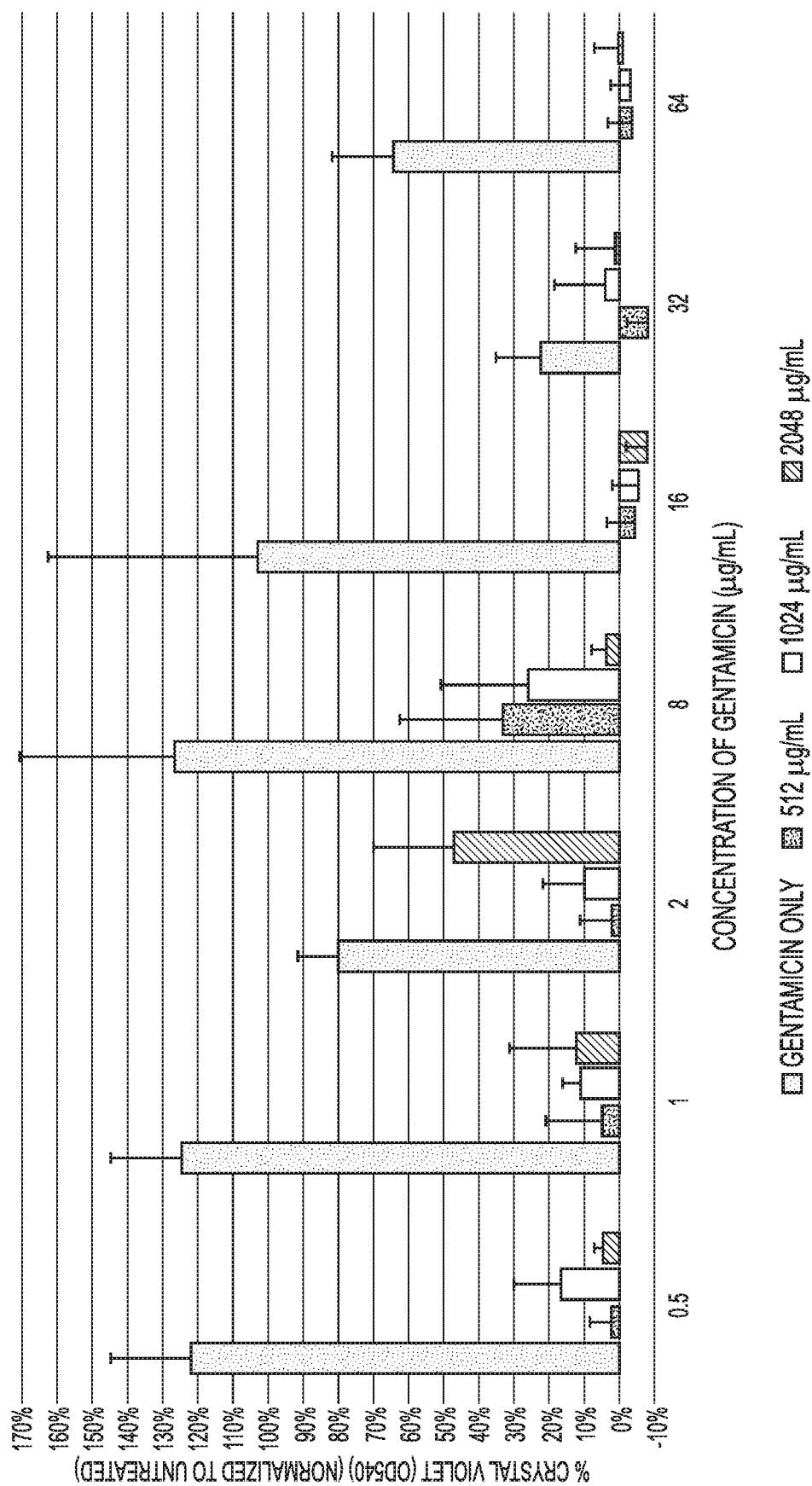

THERAPIES FOR TREATING AND PREVENTING CHRONIC RHINOSINUSITIS

CROSS-REFERENCE TO RELATED APPLICATIONS

This application is a national stage under 35 U.S.C. 371 of International Application No. PCT/US2018/052269, filed Sep. 21, 2018 (expired). International Application No. PCT/US2018/052269 cites the priority to and benefit of U.S. Provisional Application 62/561,313, filed Sep. 21, 2017.

CROSS-REFERENCE TO RELATED APPLICATIONS

This application claims priority to U.S. Provisional Application No. 62/561,313, filed Sep. 21, 2017. This Provisional application is incorporated by reference herein, in its entirety.

FIELD OF THE INVENTION

The invention relates to compositions and methods for disrupting preformed biofilm or preventing formation of biofilms by a bacterium as well as methods and compositions for treating and preventing chronic rhinosinusitis.

BACKGROUND OF THE INVENTION

Biofilms are protective films produced by bacterial communities that can allow bacteria to become resistant to treatment and can present problematic and sometimes life-threatening chronic infections. The clinical treatment of biofilm infections often proves to be particularly problematic because they are difficult to treat and generally display a reduced sensitivity to regular antibiotics, such as may result from protection and encasement of the bacteria in the biofilm matrix. Biofilms are known to be involved in a number of human disease and conditions.

One such disease is chronic rhinosinusitis (CRS). CRS is a disease affecting approximately 40 million people in the U.S. alone. This disease involves long-term inflammation of the nasal and paranasal sinus mucosa. In addition to causing physical suffering, it also impacts psychological wellbeing and daily functioning of patients. There is strong evidence supporting that bacterial biofilms are an important contributing factor to the development of chronic rhinosinusitis. In spite of the widespread prevalence of this disease, currently there are no satisfactory therapies for managing and treating CRS. Billions of dollars are spent annually in healthcare costs in attempts to palliate the condition.

Clearly, there is an unmet need in the art for effective compositions and methods to disrupt preformed biofilm or prevent formation of biofilms by a bacterium. Additionally, there is an unmet need in the art for effective compositions and methods to treat and prevent chronic rhinosinusitis. The present invention addresses these and other unfulfilled medical needs by providing novel methods and compositions useful for disrupting preformed biofilm or preventing formation of biofilms by a bacterium and for treating and/or preventing CRS.

SUMMARY OF THE INVENTION

In one aspect, the invention provides methods for disrupting preformed biofilm or preventing formation of biofilms by bacteria. These methods of the invention typically entail contacting the biofilm and/or bacteria with a therapeutically effective amount of at least one antibiotic and at least one phospholipid. In some methods of the present disclosure, the phospholipid compound typically contains (a) a hydrophilic head comprising a phosphate group and (b) a hydrophobic tail comprising one or more fatty acid chains that have at least about 8, 9 or 10 carbon atoms in total. Some of the methods are directed to biofilm and/or bacteria present in the sinonasal passage of a mammalian subject. In some methods, the antibiotic and the phospholipid compound are contacted with the bacterium in the form of dry powder or liquid formulation.

In some methods of the invention, the hydrophilic head of the employed phospholipid additionally contains a choline group that is linked to the phosphate group. In some embodiments, the hydrophobic tail of the phospholipid contains one fatty acid chain with at least 9, 10, 11, 12, 13, 14, or more carbon atoms and less than 50 or less than 20 carbon atoms. In some other methods, the hydrophobic tail of the phospholipid contains two fatty acid chains that each has at least 5, 6, 7, 8, or more carbon atoms and less than 25 or less than 15 carbon atoms. In some embodiments, the one or more fatty acid chains of the employed phospholipid contain no unsaturated hydrocarbon. In various embodiments, the phospholipid and the antibiotic are present in a composition, including a pharmaceutical composition. In some methods, the phospholipid and the antibiotic are contacted with the bacteria simultaneously. In some other methods, the phospholipid and the antibiotic are contacted with the bacteria sequentially.

Some methods of the invention employ a phospholipid that is a phosphoglyceride. For example, the employed phospholipid can be the phosphoglyceride 1,2-diheptanoyl-sn-glycero-3-phosphocholine (DHPC). In some other methods, the employed phospholipid is a lysophospholipid or a lysophospholipid derivative. For example, the methods can employ the lysophospholipid derivative dodecylphosphocholine or tetradecylphosphocholine. In some embodiments, the employed antibiotic can include one or both of gentamicin and tobramycin.

In a related aspect, the invention provides methods for treating or preventing chronic rhinosinusitis (CRS) in a mammalian subject. These methods involve administering to a subject afflicted with or at risk of developing CRS a therapeutically effective amount of at least one antibiotic and at least one phospholipid compound. In some methods of the present disclosure, the administered phospholipid contains (a) a hydrophilic head comprising a phosphate group and (b) a hydrophobic tail comprising one or more fatty acid chains that have at least about 8, 9 or 10 combined carbon atoms. In some methods, the hydrophilic head of the phospholipid can additionally contain a choline group that is linked to the phosphate group.

In some embodiments, the hydrophobic tail of the employed phospholipid contains just one fatty acid chain of at least 9, 10, 11, 12, 13, 14, or more carbon atoms and less than 50 or less than 20 carbon atoms. In some other embodiments, the hydrophobic tail of the employed phospholipid contains two fatty acid chains that each has at least 5, 6, 7, 8, or more carbon atoms and less than 25 or less than 15 carbon atoms. In some methods, the one or more fatty acid chains of the employed phospholipid contain no unsaturated hydrocarbon.

In some embodiments, the phospholipid and the antibiotic are administered to the subject simultaneously. In some other embodiments, the phospholipid and the antibiotic are administered to the subject sequentially. In some methods, a pharmaceutical composition comprising the phospholipid and the antibiotic are administered through the nasal sinus of the subject. In various embodiments, the administered pharmaceutical composition is a dry composition, an aerosolized composition or a liquid composition. In some of these embodiments, the pharmaceutical composition is administered to the subject via an inhaler, a syringe device, an aerosol device or a nebulizer. In some methods, the pharmaceutical composition is administered to the subject in combination with a steroid or an antifungal compound. Some methods of the invention can additionally include examining the subject for improved sinus symptoms, a lowered volume of nasal fluid or post-nasal drip, a partial or complete removal of biofilm in the sinuses, or a decreased appearance of inflammation in the sinuses.

Some methods of the present disclosure employ a phospholipid that is a phosphoglyceride. For example, the employed phospholipid can be the phosphoglyceride DHPC. In some other methods, the employed phospholipid is a lysophospholipid or a lysophospholipid derivative. For example, the methods can employ the lysophospholipid derivative dodecylphosphocholine or tetradecylphosphocholine. In some embodiments, the employed antibiotic can include one or both of gentamicin and tobramycin.

In another aspect, the invention provides therapeutic kits or combinations, as well as related pharmaceutical compositions, for treating or preventing chronic rhinosinusitis (CRS). Such therapeutic kits and compositions typically contain at least one antibiotic and at least one phospholipid compound. In some methods of the present disclosure, the phospholipid compound in the kits and related compositions contains (a) a hydrophilic head comprising a phosphate group and (b) a hydrophobic tail comprising one or more fatty acid chains that have at least about 8, 9 or 10 carbon atoms in total. In some embodiments, the hydrophobic tail of the employed phospholipid contains one fatty acid chain of at least 9, 10, 11, 12, 13, 14, or more carbon atoms and less than 50 or less than 25 carbon atoms. In some other embodiments, the hydrophobic tail of the employed phospholipid contains two fatty acid chains that each has at least 5, 6, 7, 8, or more carbon atoms and less than 25 or less than 15 carbon atoms. In some embodiments, the phospholipid is a phosphoglyceride. For example, the phospholipid can be the phosphoglyceride DHPC. In some embodiments, the employed is a lysophospholipid or a lysophospholipid derivative. For example, the lysophospholipid derivative can be dodecylphosphocholine or tetradecylphosphocholine. In some embodiments, the can include one or both of gentamicin and tobramycin.

In some embodiments, the one or more fatty acid chains of the employed phospholipid contain no unsaturated hydrocarbon. In some embodiments, the employed phospholipid compound is dodecylphosphocholine, tetradecylphosphocholine or 1,2-diheptanoyl-sn-glycero-3-phosphocholine (DHPC), and the employed antibiotic includes one or both of gentamicin and tobramycin. In some embodiments, the phospholipid and/or antibiotic are in the form of a dry powder of liquid formulation.

These and other objects and features of the invention will become more fully apparent in view of the following description of the invention.

DESCRIPTION OF THE DRAWINGS

FIGS. 5A, 5B, and 5C show disruption of preformed P. aeruginosa biofilms 24 h after treatment with gentamicin, either in the absence of a phospholipid or in the presence of a phospholipid at 512, 1024 or 2048 µg/ml concentrations. The phospholipids investigated are MAPCHO-12 (FIG. 5A), MAPCHO-14 (FIG. 5B), and MAPCHO-16 (FIG. 5C).

DETAILED DESCRIPTION

Figure 1:
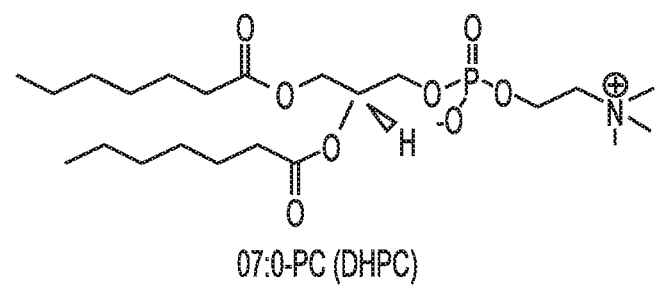
FIG. 1 shows structures of several phospholipids that have demonstrated positive activities when combined with antibiotics in disrupting preformed bacterial biofilm or preventing the formation of bacterial biofilms, 1,2-diheptanoyl-sn-glycero-3-phosphocholine (DHPC), dodecylphosphocholine (MAPCHO-12) and tetradecylphosphocholine (MAPCHO-14).
Figure 1:
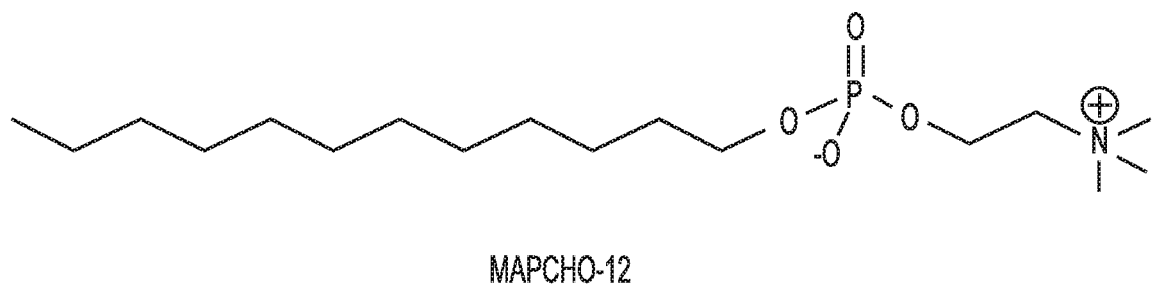
Figure 1:
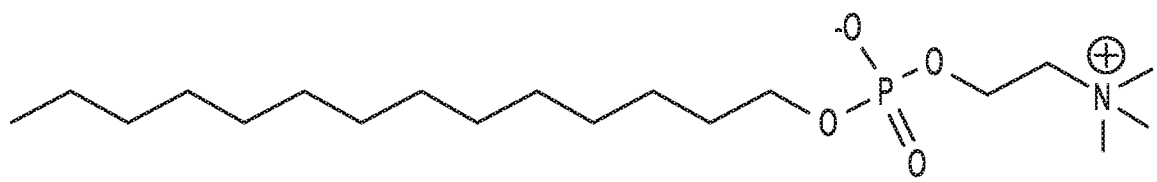

In one embodiment, compositions and methods for disrupting preformed bacterial biofilm or preventing formation of bacterial biofilms are provided. In one embodiment, a biofilm is present in the nasal and/or sinonasal passages of a subject. These methods of the present disclosure typically entail contacting the biofilm and/or bacteria with a therapeutically effective amount of at least one antibiotic and at least one phospholipid.

In another embodiment, the invention relates to compositions and methods for treating or preventing chronic rhinosinusitis (CRS). These methods involve administering to a subject afflicted with or at risk of developing CRS a therapeutically effective amount of at least one antibiotic and at least one phospholipid compound.

Typically, the compositions for use in such methods contain at least one antibiotic compound and at least one phospholipid compound described herein. It was observed by the present inventors that the combination of the antibiotics and the phospholipids lead to a synergistic effect in disrupting preformed bacterial biofilm or degrading bacterial biofilms, which represent an important factor in the development of CRS. Specifically, it was found that interaction of the phospholipids with biofilms produced by various bacteria (e.g., *S. aureus* and *P. aeruginosa*) allowed antibiotics such as gentamicin and tobramycin to cause cytotoxicity to the bacteria. In addition to disrupting/degrading preformed bacterial biofilms, it was also found that the combination of phospholipids and antibiotics also prevented formation of bacterial biofilms.

In accordance with the inventors' studies exemplified herein, the invention provides methods and compositions, including therapeutic compositions, for disrupting preformed bacterial biofilm and preventing bacterial biofilms, and for treating and preventing CRS in mammalian subjects. In addition to antibiotics and phospholipids, other compounds or agents useful for treating a bacterial biofilm, alleviating symptoms of CRS and/or for reducing damages to the nasal and paranasal sinus tissues of a subject can also be included in the compositions of the invention.

Definitions

The terms below have the following meanings, unless indicated otherwise.

As used herein and in the appended claims, the singular forms "a," "an," and "the" include plural reference unless the context clearly dictates otherwise.

Biofilms or bacterial biofilms refer to a collective of one or more types of microorganisms that can grow on many different surfaces. Bacteria exist in two distinct forms: biofilm and planktonic. Biofilm is the state in which an estimated 99% of bacteria exist. The bacteria that constitute a biofilm display several critical differences in regard to growth dynamics and genetic expression relative to their planktonic counterparts. In a biofilm, cells stick to each other and often also to a surface. These adherent cells become embedded within a slimy extracellular matrix that is composed of extracellular polymeric substances (EPS). The EPS components are produced by the cells within the biofilm and are typically a polymeric conglomeration of extracellular DNA, proteins, and polysaccharides. Biofilms may form on living or non-living surfaces and can be prevalent in natural, industrial and hospital settings. Microorganisms that form biofilms include bacteria, fungi and protists. There is increasing evidence that biofilms are critical to the pathophysiology of chronic infections including chronic rhinosinusitis.

As used herein, the term choline refers to the class of quaternary ammonium salts with the chemical formula $(CH_3)_3N^+(CH_2)_2OHX^-$, where $X^-$ is a counterion such as chloride, hydroxide or tartrate.

Chronic rhinosinusitis (CRS), commonly also known as 'chronic sinusitis', is a chronic disease that involves long-term inflammation of the nasal and paranasal sinus mucosa. The term CRS encompasses all inflammatory disorders of the nose and paranasal sinuses with a duration of many weeks. Despite being widespread, little is known about the etiology of CRS. Treatment has been symptomatic and focused on relieving symptoms. Most CRS patients have an eosinophilic infiltration of their nasal tissue (mucosa), regardless of atopy and elevated immunoglobulin E levels.

Although fungi are ubiquitous and in the nasal mucus of both healthy people and CRS patients, fungi can exacerbate bacterial infection in certain circumstances. Fungi in the nasal mucus are harmless, yet in CRS patients these same fungi stimulate an inflammatory response, inducing the eosinophils to leave the blood vessels and enter the nasal and sinus tissue and ultimately enter the nasal airway mucus. In the nasal mucus these eosinophils attack the fungi and destroy the fungi by the release of a toxic substance called major basic protein (MBP) from the granules in the eosinophils. This degranulation and release of the toxic MBP not only destroys fungi, but also produces collateral damage injuring the nasal and sinus mucosal lining tissue. The injury to the mucosal lining makes the nasal and sinus mucosa susceptible to penetration and potential infection by bacteria. When this tissue inflammation and damage is persistent and prolonged, the condition is called CRS.

Regardless of the underlying etiology, CRS patients exhibit impaired mucociliary clearance along with the formation of biofilms. Biofilm is a fine layer that forms on the surfaces of the sinus cavities as a result of inflammatory conditions. The film is generated by breakdown products of inflammation, including fragments of cell walls, cellular and plasma proteins, soluble degradation products including peptides, carbohydrates and lipids. As mixtures of these agents dry in the air-containing sinus, they form a film. The biofilm entraps bacteria and fungi that develop into colonies. Being surrounded by biofilm membrane, the colonies of bacteria and fungi are able to resist bactericidal and fungicidal therapeutic agents.

The diagnosis of CRS is based largely on symptomatic criteria, with anterior rhinoscopy or endoscopy, and, if there is any doubt about the diagnosis, computed tomography imaging is employed to confirm the presence of diseased sinus mucosa. Treatment of CRS, whether medical (intranasal corticosteroids, saline irrigations) or surgical, is aimed at decreasing inflammation and obstruction in the sinonasal passages. Antibiotics are commonly used in treating when there is suspicion of an acute bacterial infection. The theory behind the fungal and eosinophilic etiology of CRS has led to use of an antifungal compound, intranasal Amphotericin B.

When used as an adjective, "human" means compatible with human physiology and a noun associated with the term "human" need not be strictly derived from *Homo sapiens*. For example, a polypeptide or other material that is described as "human" will cause substantially no immune reaction in a human.

Microemulsions are clear, thermodynamically stable, isotropic liquid mixtures of oil, water and surfactant, frequently in combination with a cosurfactant. The aqueous phase may contain salt(s) and/or other ingredients, and the "oil" may actually be a complex mixture of different hydrocarbons and olefins. In contrast to ordinary emulsions, microemulsions form upon simple mixing of the components and do not require the high shear conditions generally used in the formation of ordinary emulsions. The three basic types of microemulsions are direct (oil dispersed in water, o/w), reversed (water dispersed in oil, w/o) and bicontinuous.

"Pharmaceutically acceptable" is a term that refers to molecular entities and compositions that do not produce an allergic or similar untoward reaction when administered to a human.

The terms "patient" and "subject" are used interchangeably and refer to mammals such as human patients and non-human primates, as well as experimental animals such as rabbits, rats, and mice, and other animals. Animals include all vertebrates, e.g., mammals and non-mammals, such as dogs, cats, sheeps, cows, pigs, rabbits, chickens, and etc. In certain embodiments, subjects for practicing the therapeutic methods of present invention are human. Subjects in need of treatment include patients already suffering from CRS as well as those prone to developing the disorder and patients suffering from a bacterial infection associated with biofilm formation as well as those prone to developing such a bacterial infection.

The terms "treating" or "treatment" includes (i) preventing a disease or disorder (e.g., CRS) from occurring (e.g. prophylaxis); (ii) inhibiting or arresting its development; and (iii) relieving symptoms associated with the condition. Thus, "treatment" includes the administration of a pharmaceutical composition of the invention and/or other therapeutic compositions or agents to prevent or delay the onset of the symptoms, complications, or biochemical indicia of the disease described herein, alleviating or ameliorating the symptoms or arresting or inhibiting further development of the disease, condition, or disorder. "Treatment" further refers to any indicia of success in the treatment or amelioration or prevention of the disease, condition, or disorder described herein, including any objective or subjective parameter such as abatement; remission; or diminishing of symptoms or making the disease condition more tolerable to the patient. Detailed procedures for the treatment or amelioration of the disease can be based on objective or subjective parameters, including the results of an examination by a physician.

"Purified" means that a material has been removed from the environment in which it was made. A material may be partially or substantially purified and need not be completely (100%) pure. For example, a phospholipid compound described herein may be purified after it has been synthesized by removing some or all of the unreacted chemicals, side products, and other components.

Unsaturated hydrocarbons are hydrocarbons that have double or triple covalent bonds between adjacent carbon atoms. Those with at least one carbon-to-carbon double bond are called alkenes and those with at least one carbon-to-carbon triple bond are called alkynes. An unsaturated compound (e.g., fatty acid chain) refers to a chemical compound that contains unsaturated hydrocarbons, such as those found in alkenes or alkynes. The unsaturated compounds need not consist only of a carbon atom chain. They can form straight chain, branched chain, or ring arrangements.

Phospholipids

The compositions and methods of the invention are aimed at disrupting preformed bacterial biofilm and/or preventing formation of bacterial biofilms. As such, the compositions and methods, particularly therapeutic compositions, are useful in the treatment of CRS and bacterial infections associated with biofilm formation. The treatment involves the use of at least one antibiotic in combination with at least one phospholipid compound described herein. Phospholipids are a group of amphipathic lipids that are composed of a nonpolar hydrophobic tail, a glycerol or sphingosine moiety (backbone), and a polar head. Phospholipids that can be employed in the practice of the present invention include both phosphoglycerides and their lysophospholipid derivatives. Thus, these phospholipid compounds can broadly include any organic compounds that fall under Formula Ia or Ib:

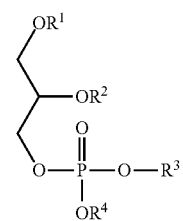

Ia

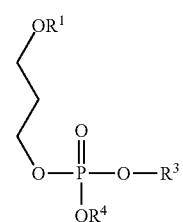

Ib where $R^1$ is a fatty acid residue, alkyl residue, or H, $R^2$ is a fatty acid residue, alkyl residue, or H, $R^3$ is H or a nitrogen containing compound such as choline ($HOCH_2CH_2N^+$ $(CH_3)_3OH^-$), ethanolamine ($HOCH_2CH_2NH_2$), inositol, or serine, and $R^4$ is a negative charge, H, or a cation such as an alkali metal cation (for example, $Li^+$, $Na^+$, or $K^+$). $R^1$ and $R^2$ are not simultaneously H. When $R^3$ is H, the compound is a dialkylglycerophosphate (also known as phosphatidic acid), while when $R^3$ is a nitrogen-containing compound, the compound is a phosphatide such as lecithin, cephalin, phosphatidyl serine, or plasmalogen. The $R^1$ site is referred to as position 1 of the phospholipid (per the stereospecific [sn] system of nomenclature), the $R^2$ site is referred to as position 2 of the phospholipid (the sn2 position), and the $R^3$ site is referred to as position 3 of the phospholipid (the sn3 position). Specific examples of phospholipids suitable for the invention include, but are not limited to, phosphatidylcholine, phosphatidylethanolamine, phosphatidylserine and phosphatidylinositol as well as corresponding lysophospholipids and lysophospholipid derivatives.

Phospholipids suitable for the invention may also include sphingolipids and phosphatidic acids. Sphingolipids (glycosylceramides) have the same phosphatidyl-based headgroup structure as in phosphoglycerides. But in contrast to a common phospholipid molecule, sphingolipids contain a single fatty acid and a long-chain alcohol as its hydrophobic components, as well as a sphingosine backbone (rather than glyercol).

As noted above, the hydrophobic tail of phospholipids can have either one or two linear fatty acid chains. In some embodiments of the invention, the hydrophobic tail of the employed phospholipids should contain at least about 8, 9, 10, or more carbon atoms in total. Thus, in some embodiments when phospholipids with two fatty acid chains are used, each chain should preferably contain at least 5, 6, 7, 8, or more carbon atoms. In some other embodiments when phospholipids with one fatty acid chain are used, the fatty acid chain should preferably contain at least about 9, 10, 11, 12, 13, 14, or more carbon atoms. In an embodiment (including any specific ranges above), a fatty acid chain of a phospholipid contains less than 50 carbon atoms, such as less than 45, less than 40, less than 35, less than 30, less than 25, less than 20, less than 19, less than 18, less than 17, less than 16, less than 15, less than 14, less than 13, less than 12, less than 11, or less than 10 carbon atoms. In an embodiment, a fatty acid chain of a phospholipid contains from 10 to 20 carbon atoms, 10 to 16 carbon atoms, 4 to 10 carbon atoms, 10 carbon atoms to 50 carbon atoms, such as from 10 carbon atoms to 16 carbon atoms, from 10 carbon atoms to 20 carbon atoms, from 10 carbon atoms to 25 carbon atoms, from 10 carbon atoms to 30 carbon atoms, from 10 carbon atoms to 35 carbon atoms, from 10 carbon atoms to 40 carbon atoms, or from 10 carbon atoms to 45 carbon atoms. In general, the nonpolar fatty acid hydrophobic tail in phospholipids can be either saturated or unsaturated. In some embodiments of the invention, the fatty acid hydrophobic tail does not contain any unsaturated hydrocarbon. In various embodiments, the fatty acid chain(s) can be an alkyl side chain, an aryl side chain or a chain of any other chemical composition that is hydrophobic in nature. The phosphate head group in the phospholipids suitable for the invention may be modified with various hydrophilic groups. As noted above, in some embodiments, the phosphate head group is attached to a nitrogen-containing base. In some of these embodiments, the phosphate group in the polar head is attached to a choline group. In some other embodiments, the phosphate group can be modified with another organic group, e.g., serine, ethanolamine or inositol.

In some methods of the invention, the employed phospholipids are phosphoglycerides (glycerophospholipids), the most common class of phospholipids. Phosphoglycerides are based on glycerol, a three-carbon alcohol with the formula $CH_2OH$—$CHOH$—$CH_2OH$. Two fatty acid chains are esterified to the glycerol backbone. The third hydroxyl group of glycerol reacts with phosphoric acid to form phosphatidate. In the practice of the invention, the two hydrophobic fatty acid chains of the employed phosphoglyceride should preferably contain a combined number of carbon atoms of at least about 5, 6, 7, 8, 9, 10, 11, 12, 13, 14, 15, 16, or more. For example, each of the two fatty acid side chain can have at least about 5, 6, 7, 8, 9 or more carbon atoms. In some embodiments, each of the two fatty acid side chain may have at least 10, 11, 12, 13, 14 or more carbon atoms. In any of the foregoing embodiments, each of the two fatty acid chains contains less than 20 carbon atoms. An exemplary phosphoglyceride that is suitable for the methods of the invention is 1,2-diheptanoyl-sn-glycero-3-phosphocholine (DHPC), as detailed in the Examples herein, which has two 7-carbon fatty acid side chains.

In some other methods of the invention, the employed phospholipids are lysophospholipids. Lysophospholipids refer to derivatives of phospholipids characterized by a single carbon chain and a polar head group. In one embodiment, the single hydrophobic fatty acid chain of the employed lysophospholipids should preferably have at least about 8, 9, or 10 carbon atoms. In an embodiment, a fatty acid chain of a lysophospholipid contains less than 50 carbon atoms, such as less than 45, less than 40, less than 35, less than 30, less than 25, less than 20, less than 19, less than 18, less than 17, less than 16, less than 15, less than 14, less than 13, less than 12, less than 11 or less than 10 carbon atoms. In an embodiment, a fatty acid chain of a lysophospholipid derivative contains from 6 carbon atoms to 50 carbon atoms, such as from 6 carbon atoms to 16 carbon atoms, from 7 carbon atoms to 20 carbon atoms, from 7 carbon atoms to 12 carbon atoms, from 10 carbon atoms to 30 carbon atoms, from 10 carbon atoms to 35 carbon atoms, from 10 carbon atoms to 40 carbon atoms, or from 10 carbon atoms to 45 carbon atoms.

In some other methods of the invention, the employed phospholipids are lysophospholipid derivatives. In various embodiments, the lysophospholipid derivatives used in the methods of the invention have a fatty acid chain that contains at least 11, 12, 13, 14, 15, 16, 17, 18, or even more carbon atoms. In an embodiment, a fatty acid chain of a lysophospholipid derivative contains less than 50 carbon atoms, such as less than 45, less than 40, less than 35, less than 30, less than 25, less than 20, less than 19, less than 18, less than 17, less than 16, less than 15, less than 14, less than 13, less than 12, or less than 11 carbon atoms. In an embodiment, a fatty acid chain of a lysophospholipid derivative contains from 10 carbon atoms to 50 carbon atoms, such as from 10 carbon atoms to 16 carbon atoms, from 10 carbon atoms to 20 carbon atoms, from 10 carbon atoms to 25 carbon atoms, from 10 carbon atoms to 30 carbon atoms, from 10 carbon atoms to 35 carbon atoms, from 10 carbon atoms to 40 carbon atoms, or from 10 carbon atoms to 45 carbon atoms. Specific lysophospholipid derivatives that have been exemplified herein for the methods of the invention include, e.g., dodecylphosphocholine with a 12-carbon fatty acid tetradecylphosphocholine with a 14-fatty acid chain and hexadecylphosphocholine with a 16-carbon fatty acid.

In an aspect, a phospholipid compound of the present disclosure has the general formula II:

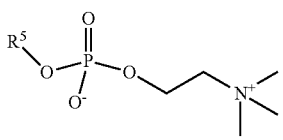

(II)

where $R^5$ is a saturated $C_9$ to $C_{17}$ alkyl chain, an unsaturated $C_9$ to $C_{17}$ alkyl chain, or

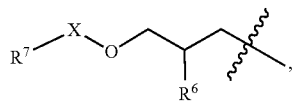

where $R^6$ is OH or

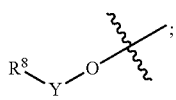

;

X and Y are each independently —$CH_2$— or —C(=O)—; $R^7$ is a saturated or unsaturated $C_3$ to $C_{14}$ alkyl chain; and $R^8$ is a saturated or unsaturated $C_3$ to $C_9$ alkyl chain, or pharmaceutically acceptable salts, solvates, and prodrugs thereof. In another related aspect, the phospholipid compound has the general formula II, where $R^5$ is a saturated or unsaturated $C_9$ to $C_{17}$ alkyl chain, or pharmaceutically acceptable salts, solvates, and prodrugs thereof.

In an aspect, $R^5$ is a saturated alkyl chain. In an aspect, $R^5$ is an unsaturated alkyl chain. In an aspect, $R^5$ is a $C_9$, $C_{10}$, $C_{11}$, $C_{12}$, $C_{13}$, $C_{14}$, $C_{15}$, $C_{16}$, or $C_{17}$ saturated alkyl chain. In an aspect, $R^5$ is a $C_9$, $C_{10}$, $C_{11}$, $C_{12}$, $C_{13}$, $C_{14}$, $C_{15}$, $C_{16}$, or $C_{17}$ unsaturated alkyl chain. In an aspect, $R^5$ is a $C_{11}$, $C_{12}$, $C_{13}$, $C_{14}$, or $C_{15}$ saturated alkyl chain. In an aspect, $R^5$ is a $C_{11}$, $C_{12}$, $C_{13}$, $C_{14}$, or $C_{11}$ unsaturated alkyl chain. In an aspect, $R^5$ is a $C_{12}$ or $C_{14}$ saturated alkyl chain. In an aspect, $R^5$ is a $C_{12}$ or $C_{14}$ unsaturated alkyl chain. In an aspect, $R^5$ is a $C_{12}$ saturated or unsaturated alkyl chain. In an aspect, $R^5$ is a $C_{14}$ saturated or unsaturated alkyl chain. In an aspect, $R^5$ is a $C_{12}$ saturated alkyl chain. In an aspect, $R^5$ is a $C_{12}$ unsaturated alkyl chain. In an aspect, $R^5$ is a $C_{14}$ saturated alkyl chain. In an aspect, $R^5$ is a $C_{14}$ unsaturated alkyl chain.

In an aspect, $R^5$ is an unsaturated alkyl chain comprising a mixture of between 1 to 3 double and/or triple bonds. In an aspect, $R^5$ is an unsaturated alkyl chain comprising between 1 to 3 double bonds. In an aspect, $R^5$ is an unsaturated alkyl chain comprising between 1 to 3 triple bonds. In an aspect, $R^5$ is an unsaturated alkyl chain comprising a mixture of 1 or 2 double or triple bonds. In an aspect, $R^5$ is an unsaturated alkyl chain comprising 1 or 2 double bonds. In an aspect, $R^5$ is an unsaturated alkyl chain comprising 1 or 2 triple bonds. In an aspect, $R^5$ is an unsaturated alkyl chain comprising 1 double or triple bond.

In an aspect, $R^5$ is an unsaturated alkyl chain comprising 1 double bond. In an aspect, $R^5$ is an unsaturated alkyl chain comprising 1 triple bond. In an aspect, $R^5$ is an unsaturated alkyl chain comprising 2 double bonds. In an aspect, $R^5$ is an unsaturated alkyl chain comprising 2 triple bonds. In an aspect, $R^5$ is an unsaturated alkyl chain comprising 1 double bond and 1 triple bond. In an aspect, $R^5$ is an unsaturated alkyl chain comprising 3 double bonds. In an aspect, $R^5$ is an unsaturated alkyl chain comprising 3 triple bonds. In an aspect comprising where the alkyl chain contains 2 double bonds and 1 triple bond. In an aspect, $R^5$ is an unsaturated alkyl chain comprising 1 double bond and 2 triple bonds.

In an aspect, $R^5$ is an unsaturated alkyl chain comprising between 1 to 3 double bonds, each having a cis- or trans-configuration. In an aspect, $R^5$ is an unsaturated alkyl chain comprising between 1 to 3 double bonds, each having a cis-configuration, a trans-configuration, or a mixture of cis- and trans-configurations. In an aspect, $R^5$ is an unsaturated alkyl chain comprising between 1 to 3 double bonds, each having a cis-configuration. In an aspect, $R^5$ is an unsaturated alkyl chain comprising between 1 to 3 double bonds, each having a trans-configuration. In an aspect, $R^5$ is an unsaturated alkyl chain comprising between 1 to 3 double bonds, each having a mixture of cis- and trans-configurations. In an aspect, $R^5$ is an unsaturated alkyl chain comprising 1 double bond having a cis-configuration. In an aspect, $R^5$ is an unsaturated alkyl chain comprising 1 double bond having a trans-configuration. In an aspect, $R^5$ is an unsaturated alkyl chain comprising 1 double bond having a mixture of cis- and trans-configurations. In an aspect, $R^5$ is an unsaturated alkyl chain comprising 2 double bonds, each having a cis-configuration. In an aspect, $R^5$ is an unsaturated alkyl chain comprising 2 double bonds, each double bond having a trans-configuration. In an aspect, $R^5$ is an unsaturated alkyl chain comprising 2 double bonds, each double bond having a mixture of cis- and trans-configurations. In an aspect, $R^5$ is an unsaturated alkyl chain comprising 2 double bonds, where 1 double bond has a cis-configuration and the other double bond has a trans-configuration.

In an aspect, $R^5$ is an unsaturated alkyl chain comprising more than one double bond, each double bond having a cis-configuration. In an aspect, $R^5$ is an unsaturated alkyl chain comprising more than one double bond, each double bond having a trans-configuration. In an aspect, $R^5$ is an unsaturated alkyl chain comprising more than one double bond, each double bond having a mixture of cis- and trans-configurations.

When $R^5$ is a saturated or unsaturated $C_9$ to $C_{17}$ alkyl chain, particularly a saturated $C_9$ to $C_{17}$ alkyl chain, the resulting phospholipid compound represents a structural analog of lysophosphatidylcholine, a type of monoalkylphosphocholine. In such a structure, the hydrophobic alkyl chain tail is linked to the phosphate moiety via an ether linkage, rendering the hydrophobic alkyl chain tail resistant to hydrolytic cleavage. By comparison, the corresponding lysophosphatidyl or glycerophosphatidylcholine compound, where the hydrophobic alkyl chain tail is linked to the phosphate moiety via an ester linkage, is more prone to hydrolysis.

Representative lysophosphatidylcholine structures IIa to IId are provided below.

In an aspect, a phospholipid compound of the present disclosure is N-decylphosphocholine (MAPCHO-10), as represented by formula IIa below:

(IIa)

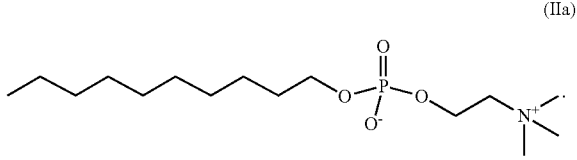 [SMILES: CCCCCCCCCCOP(=O)([O-])OCC[N+](C)(C)C]

In an aspect, a phospholipid compound of the present disclosure is N-dodecylphosphocholine (MAPCHO-12), as represented by formula IIb below:

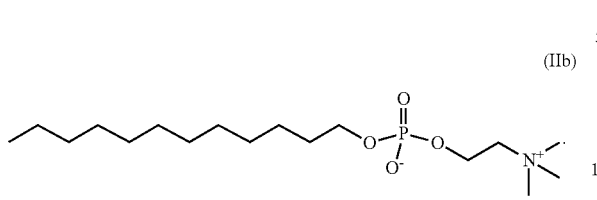
(IIb)

In an aspect, a phospholipid compound of the present disclosure is N-tetradecylphosphocholine (MAPCHO-14), as represented by formula IIc below:

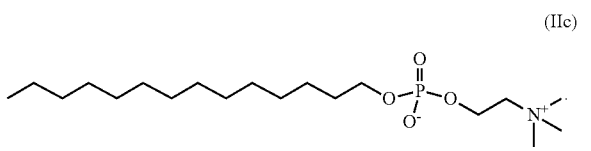 [SMILES: CCCCCCCCCCCCCCOP(=O)([O-])OCC[N+](C)(C)C]
(IIc)

In an aspect, a phospholipid compound of the present disclosure is N-tetradecylphosphocholine (MAPCHO-16), as represented by formula IId below:

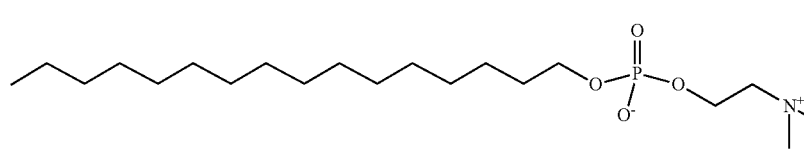
(IId)

In an aspect, a phospholipid compound of the present disclosure is chosen from the group consisting of N-dodecylphosphocholine, N-tetradecylphosphocholine, and N-hexadecylphosphocholine. In an aspect, a phospholipid compound of the present disclosure is either N-dodecylphosphocholine or N-tetradecylphosphocholine. In an aspect, a phospholipid compound of the present disclosure is either N-dodecylphosphocholine or N-hexadecylphosphocholine. In an aspect, a phospholipid compound of the present disclosure is either N-tetradecylphosphocholine or N-hexadecylphosphocholine. In an aspect, a phospholipid compound of the present disclosure is N-dodecylphosphocholine. In an aspect, a phospholipid compound of the present disclosure is N-tetradecylphosphocholine. In an aspect, a phospholipid compound of the present disclosure is N-hexadecylphosphocholine.

In an aspect, a phospholipid compound of the present disclosure has the general formula II, where $R^5$ is

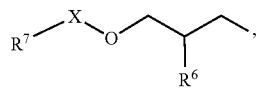

$R^6$ is OH, X is —$CH_2$— or —C(=O)—, and $R^7$ is a saturated or unsaturated $C_5$ to $C_{14}$ alkyl chain, resulting in a compound of the general formula III, or pharmaceutically acceptable salts, solvates, and prodrugs thereof:

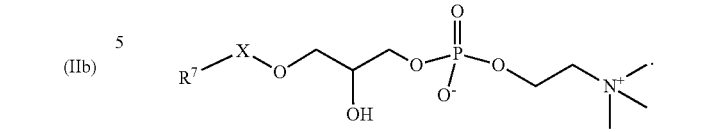
(III)

In a further aspect, X is —C(=O)—, and $R^7$ is a saturated or unsaturated $C_5$ to $C_{14}$ alkyl chain, resulting in a phospholipid compound of the general formula IIIa, or pharmaceutically acceptable salts, solvates, and prodrugs thereof:

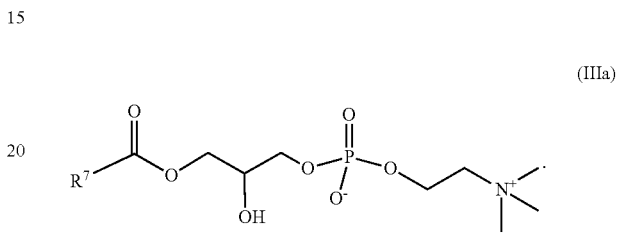
(IIIa)

In another further aspect, X is —$CH_2$—, and $R^7$ is a saturated or unsaturated $C_5$ to $C_{14}$ alkyl chain, resulting in a phospholipid compound of the general formula IIIb, or pharmaceutically acceptable salts, solvates, and prodrugs thereof:

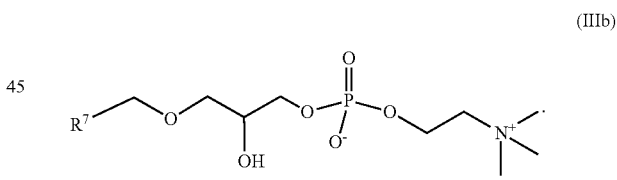
(IIIb)

In an aspect, a phospholipid compound has the formula III, IIIa, or IIIb, where $R^7$ is a $C_5$, $C_6$, $C_7$, C, $C_8$, $C_9$, $C_{10}$, $C_{11}$, $C_{12}$, $C_{13}$, or $C_{14}$ saturated or unsaturated alkyl chain. In an aspect, a phospholipid compound has the formula III, IIIa, or IIIb, where $R^7$ is a $C_8$, $C_9$, $C_{10}$, $C_{11}$, $C_{12}$, or $C_{13}$ saturated or unsaturated alkyl chain. In an aspect, a phospholipid compound has the formula III, IIIa, or IIIb, where $R^7$ is a $C_9$ or $C_{11}$ saturated or unsaturated alkyl chain. In an aspect, a phospholipid compound has the formula III, IIIa, or IIIb, where $R^7$ is a $C_9$ saturated or unsaturated alkyl chain.

In an aspect, a phospholipid compound has the formula III, IIIa, or IIIb, where $R^7$ is a saturated alkyl chain. In an aspect, a phospholipid compound has the formula III, IIIa, or IIIb, where $R^7$ is an unsaturated alkyl chain comprising a mixture of between 1 to 3 double or triple bonds. In an aspect, a phospholipid compound has the formula III, IIIa, or IIIb, where $R^7$ is an unsaturated alkyl chain comprising 1 or 2 double bonds. In an aspect, a phospholipid compound has the formula III, IIIa, or IIIb, where $R^7$ is an unsaturated alkyl chain comprising one or more double bonds, each double bond having a cis-configuration, a trans-configuration, or a mixture of cis- and trans-configurations. In an aspect, a phospholipid compound has the formula III, IIIa, or IIIb, where $R^7$ is an unsaturated alkyl chain comprising at 1 or more double bonds, where at least 1 of the double bonds has a cis-configuration. In an aspect, a phospholipid compound has the formula III, IIIa, or IIIb, where $R^7$ is an unsaturated alkyl chain comprising 1 or 2 double bonds, where each double bond has a cis-configuration.

In an aspect, a phospholipid compound has the formula III, IIIa, or IIIb, where $R^7$ is a $C_5$, $C_6$, $C_7$, C, $C_8$, $C_9$, $C_{10}$, $C_{11}$, $C_{12}$, $C_{13}$, or $C_{14}$ saturated alkyl chain. In an aspect, a phospholipid compound has the formula III, IIIa, or IIIb, where $R^7$ is a $C_8$, $C_9$, $C_{10}$, $C_{11}$, $C_{12}$, or $C_{13}$ saturated alkyl chain. In an aspect, a phospholipid compound has the formula III, IIIa, or IIIb, where $R^7$ is a $C_9$ or $C_{11}$ saturated alkyl chain. In an aspect, a phospholipid compound has the formula III, IIIa, or IIIb, where $R^7$ is a $C_9$ saturated alkyl chain.

A phospholipid compound having the formula III is a lysophosphatidylcholine. A phospholipid compound having the formula IIIa is a lysophosphatidylcholine with an ester linkage to $R^7$. A phospholipid compound having the formula IIIb is a lysophosphatidylcholine with an ether linkage to $R_7$. As described above, an ether linkage is resistant to hydrolytic cleavage.

Representative phospholipid compounds having the formula IIIa are represented by structures IIIc to IIIf below.

In an aspect, a phospholipid compound of the present disclosure is 08:0 Lyso PC (1-octanoyl-2-hydroxy-sn-glycero-3-phosphocholine), as represented by formula IIIc below:

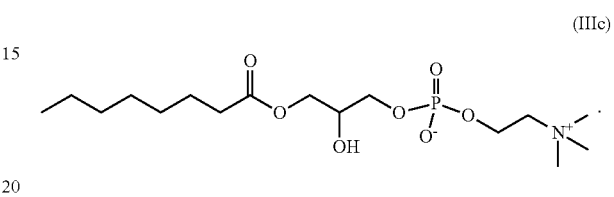

(IIIc)

In an aspect, a phospholipid compound of the present disclosure is 10:0 Lyso PC (1-decanoyl-2-hydroxy-sn-glycero-3-phosphocholine), as represented by formula IIId below:

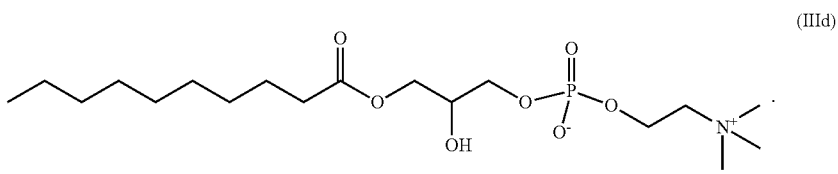 [SMILES: CCCCCCCCCC(=O)OCC(O)COP(=O)([O-])OCC[N+](C)(C)C]

(IIId)

In an aspect, a phospholipid compound of the present disclosure is 12:0 Lyso PC (1-dodecanoyl-2-hydroxy-sn-glycero-3-phosphocholine), as represented by formula IIIe below:

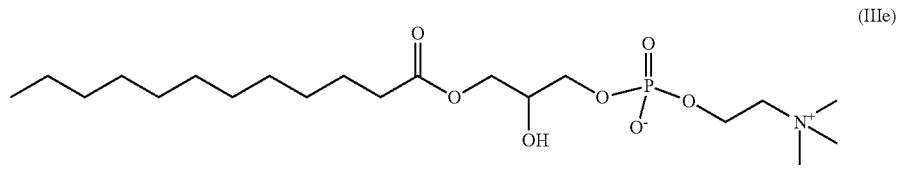 [SMILES: CCCCCCCCCCCC(=O)OCC(O)COP(=O)([O-])OCC[N+](C)(C)C]

(IIIe)

In an aspect, a phospholipid compound of the present disclosure is 13:0 Lyso PC (1-tridecanoyl-2-hydroxy-sn-glycero-3-phosphocholine), as represented by formula IIIf below:

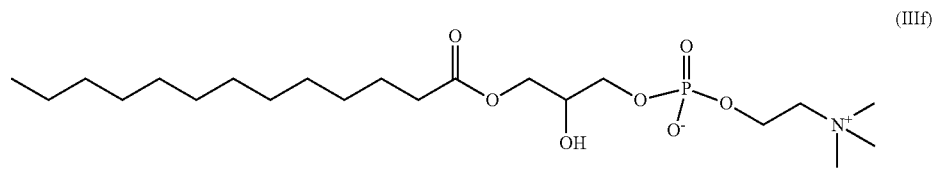 [SMILES: CCCCCCCCCCCCC(=O)OCC(O)COP(=O)([O-])OCC[N+](C)(C)C]

(IIIf)

In an aspect, compounds of the general formula IIIa are 08:0 Lyso PC, 10:0 Lyso PC, and 12:0 Lyso PC. In an aspect, compounds of the general formula IIIa are 10:0 Lyso PC and 12:0 Lyso PC. In an aspect, a compound of the general formula IIIa is 10:0 Lyso PC.

Representative phospholipid compounds having the formula IIIb are represented by structures IIIg to IIIj below.

In an aspect, a phospholipid compound of the present disclosure is ether 08:0 Lyso PC (1-octanoyl-2-hydroxy-sn-glycero-3-phosphocholine), as represented by formula IIIg below:

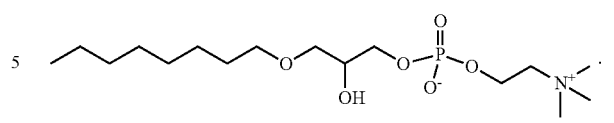

In an aspect, a phospholipid compound of the present disclosure is ether 10:0 Lyso PC (1-decanoyl-2-hydroxy-sn-glycero-3-phosphocholine), as represented by formula IIIh below:

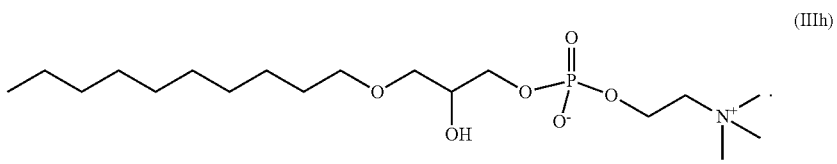 [SMILES: CCCCCCCCCCOCC(O)COP(=O)([O-])OCC[N+](C)(C)C]

In an aspect, a phospholipid compound of the present disclosure is ether 12:0 Lyso PC (1-dodecanoyl-2-hydroxy-sn-glycero-3-phosphocholine), as represented by formula IIIi below:

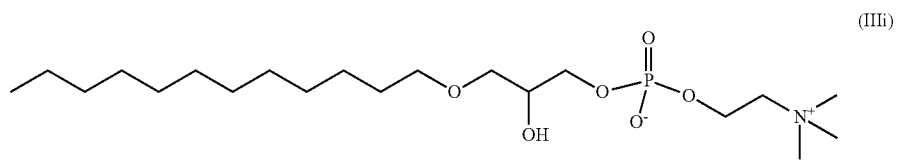 [SMILES: CCCCCCCCCCCCOCC(O)COP(=O)([O-])OCC[N+](C)(C)C]

In an aspect, a phospholipid compound of the present disclosure is ether 13:0 Lyso PC (1-tridecanoyl-2-hydroxy-sn-glycero-3-phosphocholine), as represented by formula IIIj below:

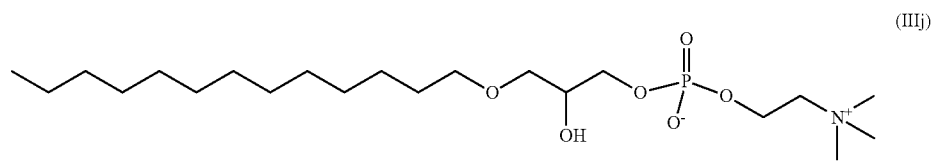 [SMILES: CCCCCCCCCCCCCOCC(O)COP(=O)([O-])OCC[N+](C)(C)C]

In an aspect, compounds of the general formula IIIb are ether 08:0 Lyso PC, ether 10:0 Lyso PC, and ether 12:0 Lyso PC. In an aspect, compounds of the general formula IIIb are ether 10:0 Lyso PC and ether 12:0 Lyso PC. In an aspect, a compound of the general formula IIIb is ether 10:0 Lyso PC.

In an aspect, a phospholipid compound of the present disclosure has the general formula II, where $R^5$ is

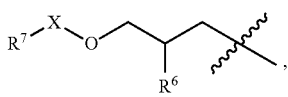

$R^6$ is

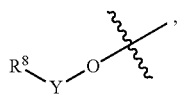

X and Y are each independently —$CH_2$— or —C(=O)—, $R^7$ is a saturated or unsaturated $C_3$ to $C_9$ acyl chain, and $R^8$ is a saturated or unsaturated $C_3$ to $C_9$ alkyl chain, or pharmaceutically acceptable, salts, solvates, and prodrugs thereof, resulting in compounds of the general formula IV:

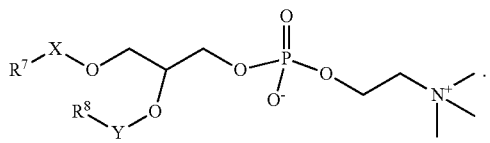

(IV)

In a further aspect, X and Y are each —C(=O)—, and $R^7$ and $R^8$ are each independently a saturated or unsaturated $C_3$ to $C_9$ alkyl chain, resulting in a phospholipid compound of the general formula IVa, or pharmaceutically acceptable salts, solvates, and prodrugs thereof:

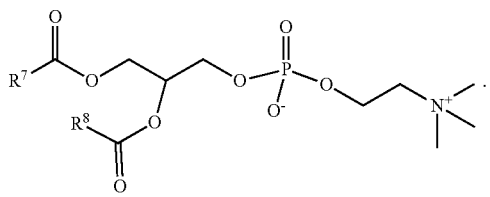

(IVa)

In another further aspect, X and Y are each —$CH_2$—, and $R^7$ and $R^8$ are each independently a saturated or unsaturated $C_3$ to $C_9$ alkyl chain, resulting in a phospholipid compound of the general formula IVb, or pharmaceutically acceptable salts, solvates, and prodrugs thereof:

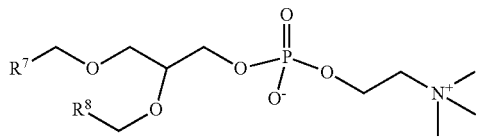

(IVb)

In another further aspect, X is —C(=O)—, Y is —$CH_2$—, and $R^7$ and $R^8$ are each independently a saturated or unsaturated $C_3$ to $C_9$ alkyl chain, resulting in a phospholipid compound of the general formula IVc, or pharmaceutically acceptable salts, solvates, and prodrugs thereof:

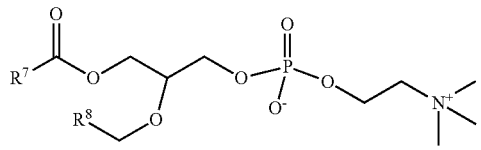

(IVc)

In another further aspect, X is —$CH_2$—, Y is —C(=O)—, and $R^7$ and $R^8$ are each independently a saturated or unsaturated $C_3$ to $C_9$ alkyl chain, resulting in a phospholipid compound of the general formula IVd, or pharmaceutically acceptable salts, solvates, and prodrugs thereof:

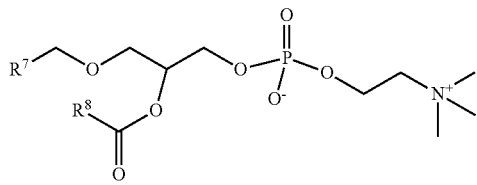

(IVd)

In an aspect, a phospholipid compound has the formula IV, IVa, IVb, IVc, or IVd, where $R^8$ is a $C_3$, $C_4$, $C_5$, $C_6$, $C_7$, $C_8$, or $C_9$ saturated or unsaturated alkyl chain. In an aspect, a phospholipid compound has the formula IV, IVa, IVb, IVc, or IVd, where $R^8$ is a $C_5$, $C_6$, or $C_7$ saturated or unsaturated alkyl chain. In an aspect, a phospholipid compound has the formula IV, IVa, IVb, IVc, or IVd, where $R^8$ is a $C_6$ saturated or unsaturated alkyl chain.

In any of the foregoing aspects, $R^7$ and $R^8$ are each a saturated alkyl chain. In any of the foregoing aspects, at least one of one of $R^7$ or $R^8$ is a saturated alkyl chain and one of one of $R^7$ or $R^8$ is optionally an unsaturated alkyl chain. In any of the foregoing aspects, $R^7$ and $R^8$ are each an unsaturated alkyl chain.

In any of the foregoing aspects, when $R^7$ and/or $R^8$ is an unsaturated alkyl chain, $R^7$ and/or $R^8$ may contain a mixture of between 1 to 3 double and/or triple bonds. In any of the foregoing aspects, when $R^7$ and/or $R^8$ is an unsaturated alkyl chain, $R^7$ and/or $R^8$ may contain a mixture of between 1 to 2 double and/or triple bonds. In any of the foregoing aspects, when $R^7$ and/or $R^8$ is an unsaturated alkyl chain, $R^7$ and/or $R^8$ may contain 1 double or triple bond.

In any of the foregoing aspects, when $R^7$ and/or $R^8$ contains 1 or more double bonds, each double bond may have a cis-configuration, a trans-configuration, or a mixture of cis- and trans-configurations. In any of the foregoing aspects, when $R^7$ and/or $R^8$ contain one or more double bonds, at least 1 of the double bonds has a cis-configuration. In any of the foregoing aspects, when $R^7$ and/or $R^8$ contain one or more double bonds, each double bond has a cis-configuration.

In an aspect, a phospholipid compound has the formula IV, IVa, IVb, IVc, or IVd, where $R^7$ and $R^8$ are identical. In an aspect, a phospholipid compound has the formula IV, IVa, IVb, IVc, or IVd, where $R^7$ and $R^8$ have identical chain lengths, the same number (or lack thereof) of double and/or triple bonds, and the same configurations of any double bonds that may be present. In an aspect, a phospholipid compound has the formula IV, IVa, IVb, IVc, or IVd, where $R^7$ and $R^8$ have identical chain lengths, where each chain is saturated. In an aspect, a phospholipid compound has the formula IV, IVa, IVb, IVc, or IVd, where $R^7$ and $R^8$ have identical chain lengths, where each chain comprises 1 or 2 double bonds, each having a cis-configuration.

In an aspect, a phospholipid compound has the formula IV, IVa, IVb, IVc, or IVd, where $R^7$ and $R^8$ are selected so that $R^7$ and $R^8$ are of the same length, resulting in the phospholipid compound of formula IV, IVa, IVb, IVc, and IVd, having 2 alkyl chains of the same length. In an aspect, a phospholipid compound has the formula IV, IVa, IVb, IVc, or IVd, where $R^7$ and $R^8$ are selected so that $R^7$ and $R^8$ have different lengths, resulting in the phospholipid compound of formula IV, IVa, IVb, IVc, and IVd, having 2 alkyl chains of different lengths.

In an aspect, a phospholipid compound has the formula IV, IVa, IVb, IVc, or IVd, where $R^7$ is a $C_3$, $C_4$, $C_5$, $C_6$, $C_7$, $C_8$, or $C_9$ saturated or unsaturated alkyl chain, and $R^3$ is a $C_3$, $C_4$, $C_5$, $C_6$, $C_7$, $C_8$, or $C_9$ saturated or unsaturated alkyl chain. In an aspect, a phospholipid compound has the formula IV, IVa, IVb, IVc, or IVd, where $R^7$ is a $C_4$, $C_5$, $C_6$, $C_7$, or $C_8$ saturated or unsaturated alkyl chain, and $R^3$ is a $C_4$, $C_5$, $C_6$, $C_7$, or $C_8$ saturated or unsaturated alkyl chain. In an aspect, a phospholipid compound has the formula IV, IVa, IVb, IVc, or IVd, where $R^7$ is a $C_5$, $C_6$, or $C_7$ saturated or unsaturated alkyl chain, and $R^3$ is a $C_5$, $C_6$, or $C_7$ saturated or unsaturated alkyl chain. In an aspect, a phospholipid compound has the formula IV, IVa, IVb, IVc, or IVd, where $R^7$ is a $C_6$ saturated or unsaturated alkyl chain, and $R^3$ is a $C_6$ saturated or unsaturated alkyl chain. In the foregoing aspects, preferably at least one of $R^7$ or $R^8$ is a saturated alkyl chain, or each of $R^7$ and $R^8$ are saturated alkyl chains.

In an aspect, a phospholipid compound has the formula IV, IVa, IVb, IVc, or IVd, where $R^7$ and $R^8$ are each a $C_4$ saturated alkyl chain, a $C_5$ saturated alkyl chain, a $C_6$ saturated alkyl chain, a $C_7$ saturated alkyl chain, or a $C_8$ saturated alkyl chain.

A phospholipid compound having the formula IV is a glycerophatidylcholine. A phospholipid compound having the formula IVa is a glycerophatidylcholine with ester linkages to both $R_7$ and $R_8$. A phospholipid compound having the formula IVb is a glycerophatidylcholine with ether linkages to both $R_7$ and $R_8$. A phospholipid compound having the formula IVc or IVd is a glycerophatidylcholine with one ester linkage and one ether linkage to the $R_7$ and $R_8$ groups. As described above, an ether linkage is resistant to hydrolytic cleavage.

Representative phospholipid compounds having the formula IVa are represented by structures IVe to IVg below.

In an aspect, a phospholipid compound of the present disclosure is 06:0 PC (1,2-dihexanoyl-sn-glycero-3-phosphocholine), as represented by formula IVe below:

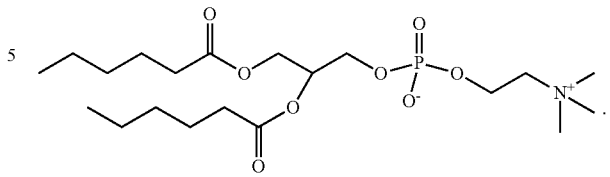

In an aspect, a phospholipid compound of the present disclosure is 07:0 PC (DHPC; 1,2-diheptanoyl-sn-glycero-3-phosphocholine), as represented by formula IVf below:

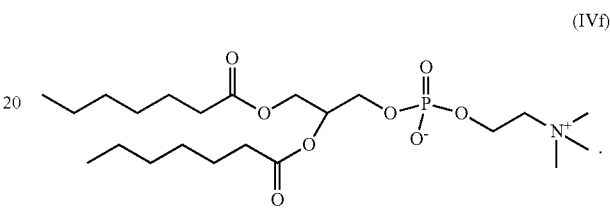

In an aspect, a phospholipid compound of the present disclosure is 08:0 PC (1,2-dioctanoyl-sn-glycero-3-phosphocholine), as represented by formula IVg below:

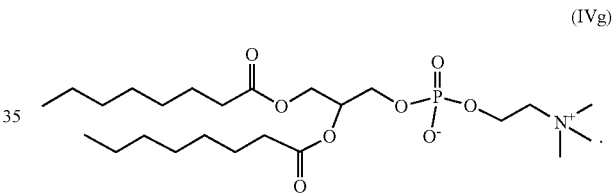

Representative phospholipid compounds having the formula IVb are represented by structures IVh to IVj below.

In an aspect, a phospholipid compound of the present disclosure is ether 06:0 PC (1,2-hexanoyl-di-O-sn-glycero-3-phosphocholine), as represented by formula IVh below:

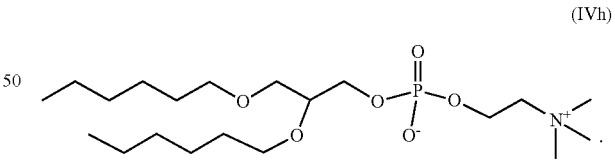

In an aspect, a phospholipid compound of the present disclosure is ether 07:0 PC (1,2-heptanoyl-di-O-sn-glycero-3-phosphocholine), as represented by formula IVi below:

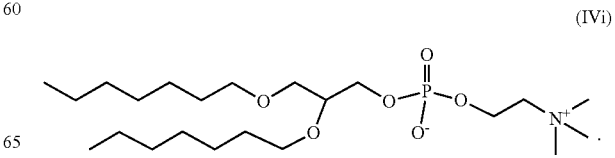

In an aspect, a phospholipid compound of the present disclosure is ether 08:0 PC (1,2-octanoyl-di-O-sn-glycero-3-phosphocholine), as represented by formula IVj below:

(IVj)

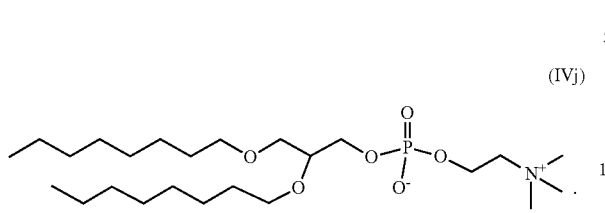

Representative phospholipid compounds having the formula IVc are represented by structures IVk to IVm below.

In an aspect, a phospholipid compound of the present disclosure is 1-hexanoyl-2-O-hexanoyl-sn-glycero-3-phosphocholine, as represented by formula IVk below:

(IVk)

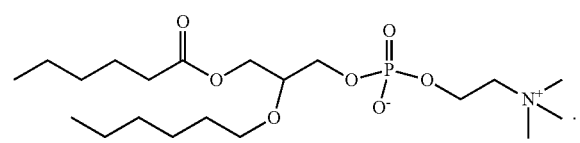

In an aspect, a phospholipid compound of the present disclosure is 1-heptanoyl-2-O-heptanoyl-sn-glycero-3-phosphocholine, as represented by formula IVl below:

(IVl)

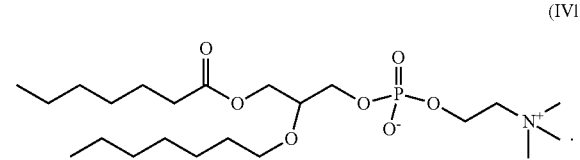

In an aspect, a phospholipid compound of the present disclosure is 1-octanoyl-2-O-octanoyl-sn-glycero-3-phosphocholine, as represented by formula IVm below:

(IVm)

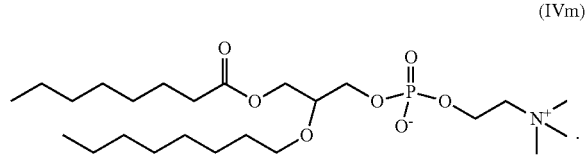 [SMILES: CCCCCCCCOC(COC(=O)CCCCCCC)COP(=O)([O-])OCC[N+](C)(C)C]

Representative phospholipid compounds having the formula IVd are represented by structures IVn to IVp below.

In an aspect, a phospholipid compound of the present disclosure is 1-O-hexanoyl-2-hexanoyl-sn-glycero-3-phosphocholine, as represented by formula IVn below:

(IVn)

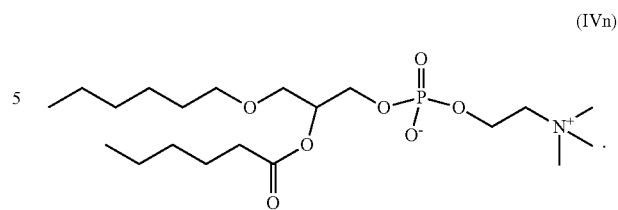 [SMILES: CCCCCCCOCC(COP(=O)([O-])OCC[N+](C)(C)C)OC(=O)CCCCCC]

In an aspect, a phospholipid compound of the present disclosure is 1-O-heptanoyl-2-heptanoyl-sn-glycero-3-phosphocholine, as represented by formula IVo below:

(IVo)

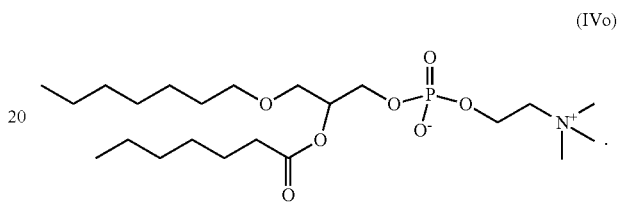

In an aspect, a phospholipid compound of the present disclosure is 1-O-octanoyl-2-octanoyl-sn-glycero-3-phosphocholine, as represented by formula IVp below:

(IVp)

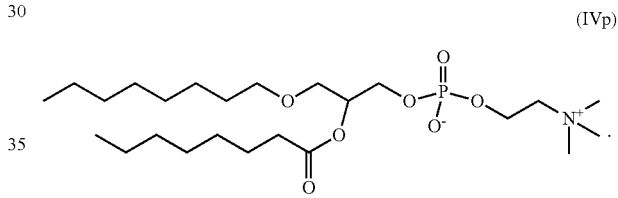

The various phospholipids that can be employed in the compositions and methods of the invention can be readily obtained from naturally resources, synthesized via standard organic chemistry protocols or purchased from commercial suppliers. For example, many phospholipids suitable for the invention can be obtained from a number of commercial vendors such as Avanti Polar Lipids Inc. (Alabaster, Ala.), Sigma-Aldrich (St. Louis, Mo.), Lipoid GmbH (Ludwigshafen, Germany), Corden Pharma, LLC (Switzerland), and NOF America Corp. (Irvine, Calif.). Many naturally existing phospholipids can also be isolated from vegetable sources like, e.g., soybeans, rape (canola) seed, wheat germ, sunflower, and flax seed, and animal material, like egg yolk, milk, or krill. There include, e.g., phosphatidylcholine, lysophosphocholine, phosphatidylethanolamine, phosphatidic acid, sphingomyelin, and phosphatidylinositol. Some phospholipids suitable for the invention may also be synthesized from naturally existing phospholipids or other known compounds. In general, synthetic phospholipids can be produced using organic chemical synthesis steps and/or enzymatic synthesis steps. Examples include, dialkyl-phosphatidylcholine synthesized from D-mannitol, mixed fatty acid chain phospholipids synthesized from glycerophosphocholine.

Antibiotics

In addition to phospholipids described herein, therapeutic compositions and related methods of the present invention also involve the use of one or more antibiotic compounds in disrupting and inhibiting formation of bacterial biofilms. As used herein, the term "antibiotic" refers to a naturally-occurring substance produced by a microorganism, such as, without limitation, a fungus or a yeast, the substance being useful in the treatment of infectious disease. Antibiotic also refers to semi-synthetic substances wherein a molecular version produced by a microorganism is subsequently modified to achieve desired properties. The commonly used generic or brand name antibiotic drugs usually fall into one of several types of antibiotics: Penicillins, Tetracyclines, Cephalosporins, Quinolones, Lincomycins, Macrolides, Sulfonamides, Glycopeptides, Aminoglycosides and Carbapenems. Specific examples of generic antibiotic drugs include amoxicillin, doxycycline, cephalexin, ciprofloxacin, clindamycin, metronidazole, azithromycin, sulfamethoxazole/trimethoprim, amoxicillin/clavulanate and levofloxacin. Examples of related brand name antibiotic drugs include Augmentin, Flagyl, (Flagyl ER), Amoxil, Cipro, Keflex, Bactrim (Bactrim DS), Levaquin, Zithromax, Avelox, and Cleocin. Any of these antibiotics and other antibiotic compounds suitable for the invention can be readily obtained from commercial drug makers, e.g., Teva Pharmaceutical Industries, Mylan, Hospira, Aspen Pharmacare, and Lupin Pharmaceuticals, Inc.

In general, any antibiotic drugs that have a cytostatic or cytotoxic effect on bacteria may be used in the methods and compositions of the invention. Any antibiotic drugs that are effective for or beneficial to treating or clearing bacterial infections in a subject, particularly in the respiratory or nasal passages of a subject, can be used in the therapeutic methods of the invention. In some embodiments, the employed antibiotic compounds are intended for bacteria that are commonly implicated in sinus infections. For example, the most common bacteria causing sinus infections include, e.g., *Staphylococcus aureus, Pseudomonas aeruginosa, Streptococcus pneumoniae, Haemophilus influenzae, Moraxella catarrhalis*, and *Streptococcus pyogenes*. Preferably, the antibiotics to be used in the methods of the invention are able to effectively kill these bacterial types.

In various embodiments, the methods of the invention can employ one or more antibiotic compounds that are routinely used in the medical field for treating infections by these and other bacterial types. In some embodiments, amoxicillin (Amoxil) or amoxicillin-clavulanate (Augmentin) may be used as the first-line drug for treatment of a suspected bacterial sinus infection. These antibiotics are usually effective against most of the species and strains of bacteria that cause sinus infections. In some other embodiments, different antibiotics may be used as first choices, esp. in subjects who are allergic to penicillin. Such antibiotics include, e.g., trimethoprim and sulfamethoxazole (Bactrim, Septra), cefaclor (Ceclor), loracarbef (Lorabid), Gentamicin (Garamycin), tobramycin, clarithromycin (Biaxin), azithromycin (Zithkromax), sulfamethoxazole (Gantanol), and ciprofloxin (Cipro). In some embodiments, the therapeutic compositions of the invention contain gentamicin. In some embodiments, the therapeutic compositions of the invention contain tobramycin. In some other embodiments, the therapeutic compositions of the invention contain more than one antibiotic compound, e.g., both gentamycin and tobramycin. In some embodiments, the subject may be treated with different antibiotics during the course of treatment. For example, if the condition of a subject is not improving after a specific period of time (e.g., 4, 5, 6, 7 or more days) following treatment with a therapeutic composition containing gentamycin or amoxicillin, a different composition containing another antibiotic compound such as tobramycin may be used.

In an embodiment, a low dose of an antibiotic is sufficient to establish an effective dose when administered alongside a phospholipid described herein. In an embodiment, when administered with a phosphocholine having 10 or more carbon atoms in in its alkyl chains, less than 1 µg/ml of gentamicin can be provided in an effective treatment of biofilms of *S. aureus*, such as less than 0.9 µg/ml, less than 0.8 µg/ml, less than 0.7 µg/ml, less than 0.6 µg/ml, less than 0.5 µg/ml, less than 0.4 µg/ml, less than 0.3 µg/ml, less than 0.2 µg/ml, less than 0.1 µg/ml, or less than 0.05 µg/ml gentamicin. In an embodiment, when administered with a lysophosphocholine derivative with 10 to 20 carbon atoms in alkyl chain (such as, but not limited to, MAPCHO-12 or MAPCHO-14), less than 0.2 µg/ml of gentamicin can be provided in an effective treatment of biofilms of *S. aureus*, such as less than 0.1 µg/ml or less than 0.05 µg/ml gentamicin. In an embodiment, when administered with a lysophosphocholine derivative with 10 to 20 carbon atoms in alkyl chain (such as, but not limited to, MAPCHO-12 or MAPCHO-14), less than 0.2 µg/ml of tobramycin can be provided in an effective treatment of biofilms of *S. aureus*, such as less than 0.1 µg/ml or less than 0.05 µg/ml tobramycin.

In general, an effective antibiotic treatment needs to be continued for a minimum of 10-14 days. In some other embodiments, the subject may be treated with the composition containing the antibiotic for a longer period of time, e.g., any number of days between 14 and 21. The exact length of treatment period depends on the subject's general health, severity of the condition, and the type of antibiotic being administered.

Treatment Methods

In one embodiment, therapeutic methods and related compositions for treating CRS and/or associated conditions in a mammalian subject are provided. CRS is often associated with several other nasal or respiratory diseases or conditions such as nasal polyposis, asthma and eosinophilia. These conditions, which may co-exist as a syndrome, are all suitable for treatment with methods of the invention. Chronic bacterial or fungal sinus infection with biofilm formation has been implicated in these conditions. Many patients afflicted with these conditions have been on multiple courses of antibiotics and/or antifungal drugs which are completely ineffective because of biofilm formation. Many of these patients have undergone repeated nasal sinus surgeries, and are commonly steroid dependent from chronic use of prednisone. Thus, in some related embodiments, the invention provides therapeutic methods for disrupting preformed bacterial biofilm or preventing formation of bacterial biofilms in a mammalian tissue. In some of these embodiments, the biofilm is present in the sinonasal passage that has been or is susceptible to be infected by a bacterial, e.g., *Staphylococcus aureus, Streptococcus pneumoniae*, and *Pseudomonas aeruginosa*.

The therapeutic methods of the invention typically involve administering to the subject, or contacting the tissue of a subject with, a therapeutically effective amount of a therapeutic composition containing at least one antibiotic compound and at least one phospholipid described herein. Upon contacting and instilled in the inflamed nasal and paranasal sinuses of subjects with CRS, the therapeutic composition is able to disrupt or remove the indwelling biofilm, and/or prevent the formation of additional biofilm, which is the root of the disease. The therapeutic activity of the therapeutic composition on the biofilm is by means of a synergistic activity that is brought about by a combination of the phospholipid and the antibiotic. As demonstrated herein, an antibiotic compound alone or a phospholipid alone showed very little or no effect in disrupting preformed bacterial biofilm or inhibiting biofilm formation. In some embodiments, the phospholipid and the antibiotic are contacted simultaneously with a mammalian tissue that has been or is suspected to be infected by a bacterial species or administered simultaneously to a subject in need of treatment. Alternatively, the antibiotic and the phospholipid can be contacted with a mammalian tissue that has been or is suspected to be infected by a bacterial species or administered to the subject in need of treatment sequentially. Thus, in some of these embodiments, the phospholipid can be administered first prior to administration of the antibiotic. In some other embodiments, the antibiotic can be administered first prior to administration of the phospholipid. Other than the phospholipid and the antibiotic, the therapeutic composition typically also contains a pharmaceutically acceptable carrier as described herein.

The therapeutic compositions containing an antibiotic and a phospholipid can be employed alone to treat subjects suffering from or at risk of developing CRS. CRS patients with or without accompanying nasal polyps are suitable for treatment with methods of the invention. In one embodiment, CRS patients with accompanying nasal polyps are treated using the therapeutic methods and compositions of the invention. In one embodiment, CRS patients without accompanying nasal polyps are treated using the therapeutic methods and compositions of the invention. Nasal polyps are polypoidal masses arising mainly from the mucous membranes of the nose and paranasal sinuses. They are overgrowths of the mucosa that frequently accompany allergic rhinitis. They are freely movable and nontender.

In one embodiment, a subject is determined to be in need of treatment with a therapeutic method or composition of the invention based on the presence or absence of a biomarker indicative of the presence and or formation of polyps, such as, but not limited to, periostin. In one embodiment, the subject is determined to be in need of treatment based on an expression pattern of periostin (Shiono et al., Auris Nasus Larnyx, 2015, 42(2), 123-7, which is hereby incorporated by reference for such teachings). In one embodiment, the subject displays a "diffuse type" periostin expression. In one embodiment, the subject displays a "superficial type" periostin expression. In one embodiment, the subject display a "superficial type" periostin expression. In one embodiment, the subject is determined to be in need of treatment based on the concentration of periostin in a in the nasal and/or sinonasal passage (Maxfield et al., Otolaryngology—Head and Neck Surgery, DOI: 10.1177/0194599817737967, which reference is hereby incorporated by reference for such teachings). In one embodiment, the subject displays a periostin concentration greater than 50 µg/ml (which is indicative of the presence of nasal polyps). In one embodiment, the subject displays a periostin concentration less than 50 µg/ml (which is indicative of the absence of nasal polyps).

In one embodiment, the administration of the therapeutic compositions by the described methods does not result in amosimia in the subject.

The therapeutic compositions of the invention can also be administered to the subject in combination with other compounds or therapies suitable for treating CRS or ameliorating symptoms of CRS. For example, the therapeutic compositions of the invention can also be used to treat CRS patients that have undergone saline washes, or used together with administration of steroids or other known therapies for CRS. In some embodiments, the therapeutic composition is co-administered to CRS patients along with an intranasal corticosteroid and decongestants for decreasing inflammation or for improving sinus drainage. In some embodiments, the therapeutic composition can be co-administered to CRS patients along with medicines that help thin the mucus (mucolytics). In some other embodiments, patients are treated with the therapeutic composition in combination with saline irrigations in order to decreasing obstruction in the sinonasal passages. In still some other embodiments, the patients are co-administered with the therapeutic composition and an antifungal compound (e.g., intranasal Amphotericin B) to control fungi infection. In these various combination therapies, the therapeutic composition of the invention can be administered to the patients prior to, concurrently with, or subsequent to treatment with the known therapy.

Any mammalian subjects suffering from chronic rhinosinusitis can be treated with the compositions and methods of the invention. Preferably, the subjects are human patients. Thus, adults, teenagers, children, infants and pre-term infants can all be treated with the compositions and methods of the invention. In general, the treatment should result in improvement in one or more symptoms in the patients associated with or mediated by CRS. These include, e.g., reduced sinus symptoms like severity of headaches, amount, color and consistency of mucous, congestion and improved sense of smell; improved quality of life as measured by standardized instruments; lowered volumes of nasal fluid or post-nasal drip; partial or complete removal of biofilm in the sinuses as determined by endoscopic examination (with biopsy for microscopic exam) or through chemical analysis of sinusoidal fluid or wash fluid, or by imaging procedures like CT (computerized tomography) or MRI; and decreased appearance of inflammation in the sinuses by endoscopic examination. Various tests or assays for monitoring these symptoms routinely practiced by physicians in diagnosing and treating CRS can be readily employed in the practice of the present invention.

The treatment methods of the invention employ a pharmaceutical composition or formulation containing at least an antibiotic and a phospholipid described herein. In some embodiments, the therapeutic composition is administered to the patients through the nasal sinus. The formulation or ingredients thereof can be provided as a dry powder, a liquid or an aerosol composition. In some embodiments, the phospholipid(s) and/or the antibiotic(s) in the therapeutic compositions of the invention are administered as dry powder to the subject in need of treatment, e.g., via an inhaler. In an embodiment, a dry powder inhaler is a single dose device, such as SPINHALER®, ROTAHALER®, or HANDIHALER®. In an embodiment, a dry powder inhaler is a multi-dose reservoir device, such as TURBUHALER®, EASYHALER®, CLICKHALER®, TWISTHALER®, or NOVOLIZER®. In an embodiment, a dry powder inhaler is a multi-unit dose device, such as AEROHALER®, DISKHALER®, DISKUS®, or ACCUHALER®. In some embodiments, the therapeutic composition is a liquid formulation. In some embodiments, the therapeutic formulation can be administered to the subjects as a microemulsion or aerosol formulation. For example, a freeze-dried preparation of the therapeutic composition can be placed into a liquid medium and put into an aerosol by any aerosol device or nebulizer. In an embodiment, a nebulizer is selected from the group consisting of a pneumatic compressor nebulizer, an ultrasonic nebulizer, a vibrating mesh or horn nebulizer, and a microprocessor-controlled breath-actuated nebulizer.

Typically, duration of treatment will be continuous until symptoms of CRS are gone or controlled. Depending on the symptoms and other specifics of the subject to be treated, the therapeutic formulation can be administered to the subjects about once a day, twice a day, three times a day, four times a day, five times a day, six times a day or even more frequently. For subjects who have undergone an extensive treatment period with substantially improved symptoms, a less frequent treatment regimen may be employed. In addition, for prophylactic purpose to prevent the development of CRS in a subject suspected of being at risk of developing the disease, a less frequent administration may also be appropriate. Thus, some subjects may be administered the therapeutic composition of the invention less frequently than once a day, e.g., every second, third to sixth day, once a week or even less frequently. Further, the therapeutic formulation may be administered to a subject at varying frequency during the treatment period. For example, a therapeutic composition of the invention can be administered to a subject daily or less frequently, i.e., every second, third to sixth day, once a week or even less frequently.

Therapeutic Compositions

The pharmaceutical compositions can be administered to a mammalian subject, such as a human patient, in a variety of forms adapted to the chosen route of administration, e.g., the nasal sinus route. Therapeutic compositions of the present invention may contain a physiologically tolerable or acceptable carrier together with the phospholipid and antibiotic compounds, as described herein, dissolved or dispersed therein as an active ingredient. In an embodiment, the therapeutic composition is not immunogenic when administered to a mammal or human patient for therapeutic purposes. Depending on the formulation and the specific patient, the amount of each of the phospholipid and the antibiotic compound in the therapeutic composition administered to a patient can be in the range of about 0.5-2,500 mg/dose, 1-1,500 mg/dose, 2-500 mg/dose, 5-100 mg/dose, or 10-50 mg/dose. Adjustments to the dose, to optimize therapeutic effectiveness, and minimize side effects, can be determined according to known procedures. The phospholipid and/or antibiotic present in the liquid or aerosol formulation can be at a concentration of, e.g., from about 0.5 mg/ml to about 50 mg/ml. Depending on the specific compounds used, the antibiotic and the phospholipid can be used with an appropriate ratio that provides optimal treatment effect. Thus, in various embodiments of the present invention, the antibiotic:phospholipid weight ratio can be in the range of about 100:1 to about 1:10,000. In some embodiments, the ratio is about 10:1, 5:1, 1:1, 1:5, 1:10, 1:100 or even lower.

In some embodiments, the therapeutic composition is processed by spray drying to produce spray-dried particles having the desired mass median aerodynamic diameter in the 1-5 μm size. The spray dried particles may then be stored and employed by the user in an aerosolization device, as above, for inhalation therapy. As indicated, the powdered particles can be delivered as a dry-powder aerosol, or the particles can be suspended in an aqueous medium for aerosolization in aqueous droplet form. Alternatively, a suitable therapeutic formulation in liquid form, e.g., a formulation solution or suspension contained in a volatile biocompatible fluid, may be formed in an aerosolization process in which the particles formed are immediately inhaled for therapeutic delivery of the active agent.

For aerosol administration, the only requirement of the therapeutic composition is that be it can be converted or processed into a suitable aerosol-particle form containing the components of the composition. In some embodiments, the therapeutic composition can be an aqueous suspension of lipid bodies prepared by lyophilization to form a dry mass that is then comminuted, e.g., by grinding, to form a composition containing dry-powder particles having a mass median aerodynamic diameter in the 1-5 μm size range. The dry-powder particles are then stored and employed in a suitable aerosolization device to produce a dry-particle aerosol suitable for inhalation treatment or for suspension in a suitable solvent, for aerosolization as a particle suspension.

In some embodiments, the formulation can be prepared via microemulsion. In some of these embodiments, the volume of the formulation to be administered to the nasal sinuses can be, e.g., from about 0.5 ml to about 100 ml, from about 1 ml to about 50 ml, from about 2.5 ml to about 25 ml, or from 5 ml to about 10 ml. In some embodiments, the therapeutic formulation can be administered, e.g., by a syringe device with a plastic tube through which the phospholipid and the antibiotic compound will be instilled into the sinuses. In some other embodiments, the therapeutic formulation can be administered with a container that squirts fluid upon squeezing into the nasal sinuses. See, e.g., U.S. Pat. No. 6,520,384.

In some other embodiments, the invention contemplates processing a liquid therapeutic formation by means of a user-controlled nebulizer or aerosolizer, to generate an aqueous-droplet aerosol containing the therapeutic formulation in lipid-body form. Components of the therapeutic formulation of this embodiment can be present in ordered, crystalline, or amorphous lipid particles suspended in the aerosol droplets.

As noted above, the formulation of the invention can be prepared as a solution formulation or as a particulate formulation. The therapeutic agent, as well as any other components of the therapeutic formulation, can also be incorporated into liposomal, crystalline, or amorphous lipid bodies suspended in an aqueous, organic, or mixed solvent. Liposomal-like therapeutic compositions of the present invention are generally sterile liposome suspensions. These liposomes may be multiple compartment or multilamellar vesicles, single compartment vesicles, macrovesicles or other colloidal forms. The multilamellar vesicles are generally the most common. Multilamellar vesicles (MLVs) can be formed by simple lipid-film hydration techniques, preferably under sterile condition. Liposomal-like therapeutic compositions may be made by a variety of techniques well known in the art. See, e.g., Szoka, F. Jr. et al., *Ann. Rev. Biophys. Bioeng.*, 9:467-508, 1980; and Olson, F. et al., *Biochim. Biophys. Acta*, 557:9-23, 1979. The formulation of liposomes may be stored as a lipid dispersion, for aerosolization in aqueous-droplet form, or the liposome formulation may be lyophilized, powdered, and administered as a dry-powder aerosol. Alternatively, a liposome dispersion may spray-dried, forming dried lipid particles in powder form, for administration as a powdered aerosol.

Freeze drying (lyophilization) is one standard method for producing a dry powder from a solution or a suspension. See, for example, Freide, M. et al., *Anal. Biochem.*, 211(1): 117-122, 1993; Sarbolouki, M. N. and T. Toliat, *PDA J. Pharm. Sci. Technol.*, 52(1):23-27, 1998). Following lyophilization, the dried therapeutic formulation is comminuted, e.g., by grinding or other conventional means, to form desired size particles. Techniques that make use of the supercritical properties of liquefied gases have been employed in the generation of microparticles and powders containing therapeutic proteins (Niven, R. W., In: MODULATED DRUG THERAPY WITH INHALATION AEROSOLS: REVISITED, A.

J. Hickey, ed., Marcel Dekker, New York). Particles with crystal habits and characteristics suitable for inhalation purposes can be prepared by these methods. Exemplary supercritical fluid processing techniques include: rapid expansion of supercritical fluids (RESS), the use of gas-antisolvent (GAS) precipitation to prepare particles, and the solution-enhanced dispersion of supercritical fluids (SEDS) (see, U.S. Pat. Nos. 5,301,644; 5,707,634; 5,770,559; 5,981,474; 5,833,891; 5,874,029, and 6,063,138).

Spray drying may also be used advantageously for producing dried lipid particles of desired sizes. (See, Master, K., SPRAY DRYING HANDBOOK, 5$^{th}$ edition, J. Wiley & Sons, New York, 1991; Maa, Y. F. et al., *Pharm. Res.*, 15(5):768-775, 1998; Maa, Y. F., *Pharm. Dev. Technol.*, 2(3):213-223, 1997). Various spray-drying methods have been described in the patent literature, See, for example, U.S. Pat. Nos. 6,174,496; 5,976,574; 5,985,284; 6,001,336; 6,015,256; 5,993,805; 6,223,455; 6,284,282; and 6,051,257.

In some related embodiments, the invention provides therapeutic kits or therapeutic combinations, as well as related pharmaceutical compositions, for disrupting preformed bacterial biofilms or for treating CRS as described herein. The kits and compositions typically contain at least one antibiotic and at least one phospholipid compound described herein. Any of the other components described above for disrupting preformed bacterial biofilm and treating CRS may also be provided in the kits or pharmaceutical compositions. Therapeutic kits of the invention may also include one or more of the above-described devices for administering the compounds or therapeutic formulations of the invention, as well as tubes, buffers, and etc. The various components of the kits may be present in separate containers, or some or all of them may be pre-combined into a reagent mixture in a single container, as desired. In addition to the above components, the kits of the invention may further include instructions for practicing the methods of the invention. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), etc., on which the information has been recorded. Yet another form of these instructions that may be present is a website address which may be used via the internet to access the information.

EXAMPLES

The following examples are intended to illustrate, but not limit, the present invention.

Example 1 Phospholipids and Antibiotics Together to Disrupt Biofilms

We performed in vitro studies of the capacity of phospholipids together with antibiotics to disrupt preformed bacterial biofilms. The tests were conducted as follows. Biofilm formation was obtained by culturing (1) *S. aureus* in tryptic soy broth media supplemented with 5% glucose; and (2) *P. aeruginosa* in cation-adjusted Mueller Hinton Broth after incubation at 37 degrees C. for 24 hours in 96 well plates. The medium was then removed and replaced by treatment solutions of antibiotics, antibiotics+phospholipids, phospholipids alone, or control solutions. Phospholipid concentration used in the assays was 512 µg/ml although in some studies, was 1025 µg/ml. After 24 hours at 37 degrees C., media was removed and fresh medium was added and the 96-well plates incubated at 37 degrees C. for 24 hours. Media were then removed and biofilm at the base of the wells was stained with crystal violet and quantitated.

Figure 2:
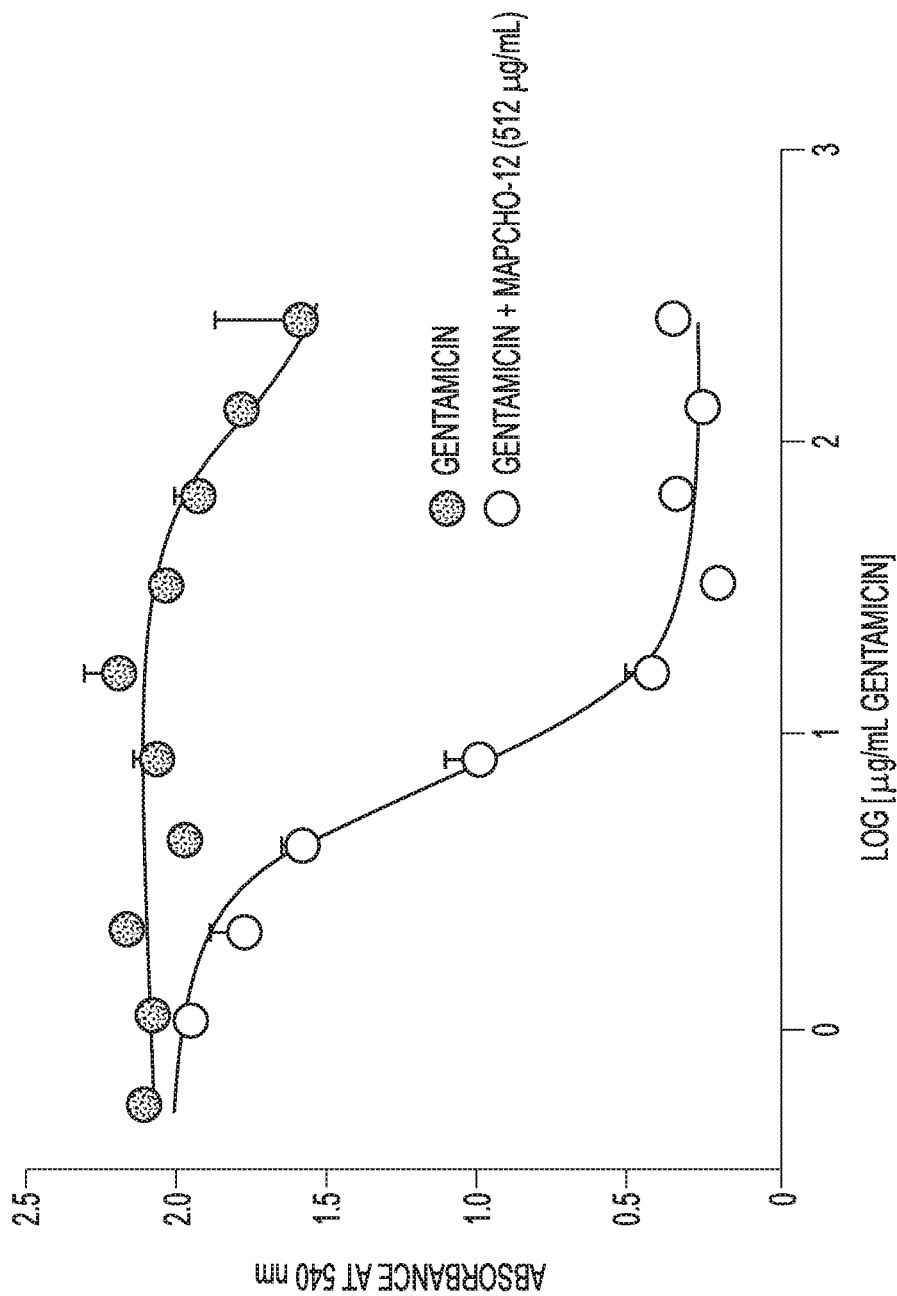
FIG. 2 shows susceptibility of preformed S. aureus (ATCC BAA-1720) biofilms to gentamicin in the presence of phospholipid MAPCHO-12.

Results from the studies were shown in FIG. 2. The results demonstrated the capacity of the phospholipid dodecylphosphocholine (MAPCHO-12) together with gentamicin to disrupt preformed biofilm of *S. aureus*. As shown in the figure, gentamicin alone was not successful. Similarly, the phospholipid alone also did not disrupt the biofilm (data not shown). With disruption of the biofilm by the phospholipid/gentamicin combination, the *S. aureus* was also sterilized.

Example 2 Phospholipids and Antibiotics Together Inhibit Biofilm Formation

We also performed in vitro tests of the capacity of phospholipids together with antibiotics to prevent formation of biofilms. Freshly grown *S. aureus* and *P. aeruginosa* were quantitated and placed in 96-well plates together with phospholipids plus gentamicin and tobramycin (antibiotics), phospholipids alone, antibiotics alone or controls solution. After 24 hours at 37 degrees C., the fluids were removed and the wells stained with crystal violet, and then the density of crystal violet in the wells was quantitated by absorption of light at 540 nm.

Figure 3:
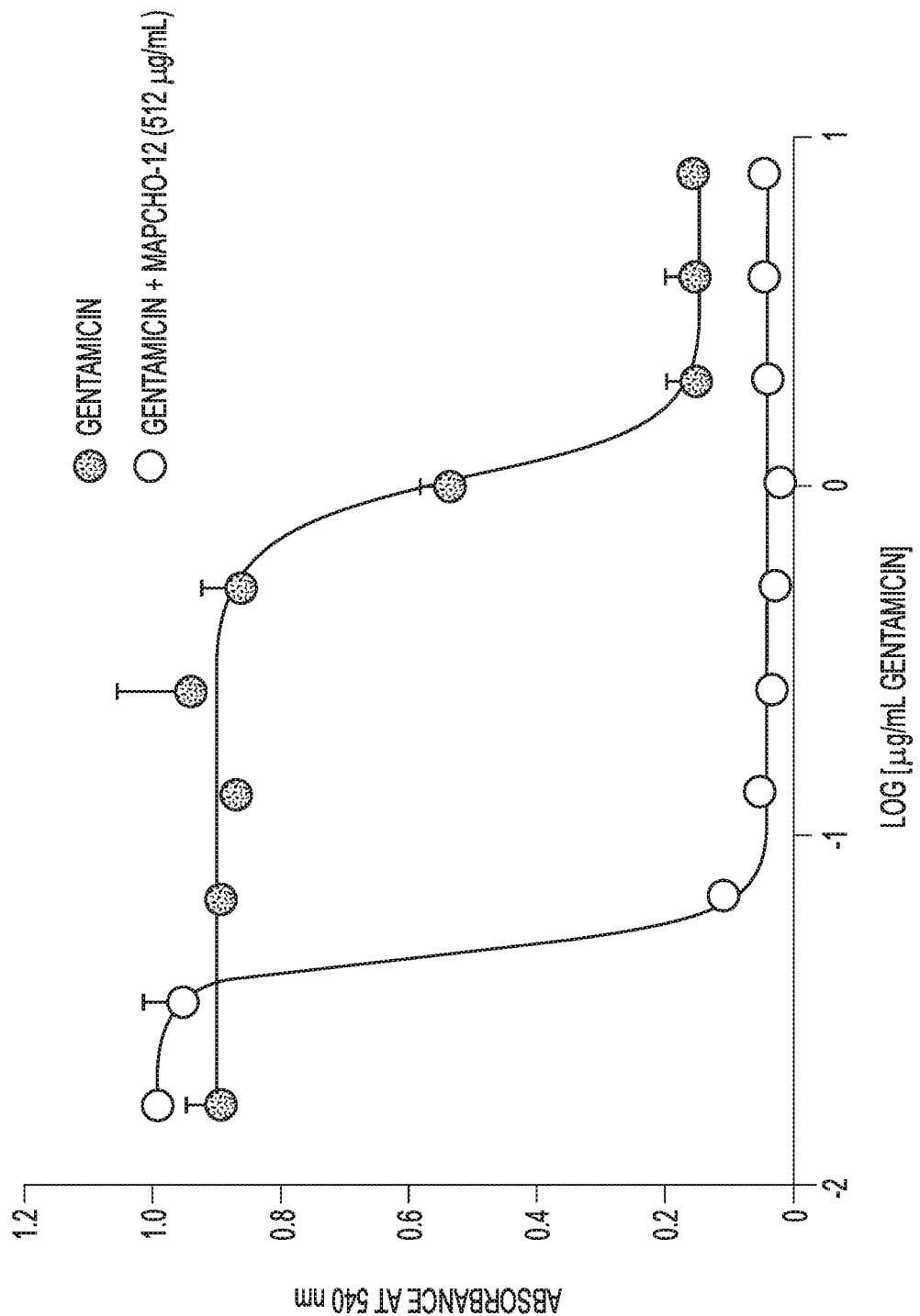
FIG. 3 shows susceptibility of S. aureus (ATCC BAA-1720) biofilm formation to gentamicin in the presence of phospholipid MAPCHO-12.

FIG. 3 shows the results from the tests, which demonstrated positive effect of the phospholipid dodecylphosphocholine (MAPCHO-12) and gentamicin, vs. negative activity of gentamicin alone, on the formation of a biofilm produced by *S. aureus*. As shown in the figure, whereas gentamicin alone does not prevent the formation of the biofilm by *S. aureus* at low concentrations of the gentamicin, the combination of gentamicin at low concentrations and the phospholipid did prevent biofilm formation. The phospholipid alone also did not prevent biofilm formation.

The same results as shown in FIG. 3 were also obtained with two other phospholipids shown in FIG. 1, dihydrophosphocholine (DPHC) and tetradecylphosphocholine. It was also observed that phospholipids that had little to no hydrophobic side-chains showed no activities in disrupting preformed bacterial biofilm of biofilms or preventing biofilm formation.

Example 3 Phospholipids and Antibiotics Together Disrupt Biofilms

We performed in vitro studies of the capacity of phospholipids together with antibiotics to disrupt preformed bacterial biofilms. The tests were conducted as follows. Biofilm formation was obtained by culturing *P. aeruginosa* in cation-adjusted Mueller Hinton Broth after incubation at 37 degrees C. for 24 hours in 96 well plates. The medium was then removed and replaced by treatment solutions of gentamicin, phospholipids plus gentamicin, or control solutions. Either three or four different phospholipids (MAPCHO-10, MAPCHO-12, MAPCHO-14, and MAPCHO-16) were tested at three different phospholipid test concentrations (512 µg/ml, 1024 µg/ml, and 2048 µg/ml). After 24 hours at 37 degrees C., media was removed and fresh medium was added and the 96-well plates were incubated at 37 degrees C. for either 6 hours or 24 hours. Media were then removed and biofilm at the base of the wells was stained with crystal violet and quantitated.

Figure 4A:
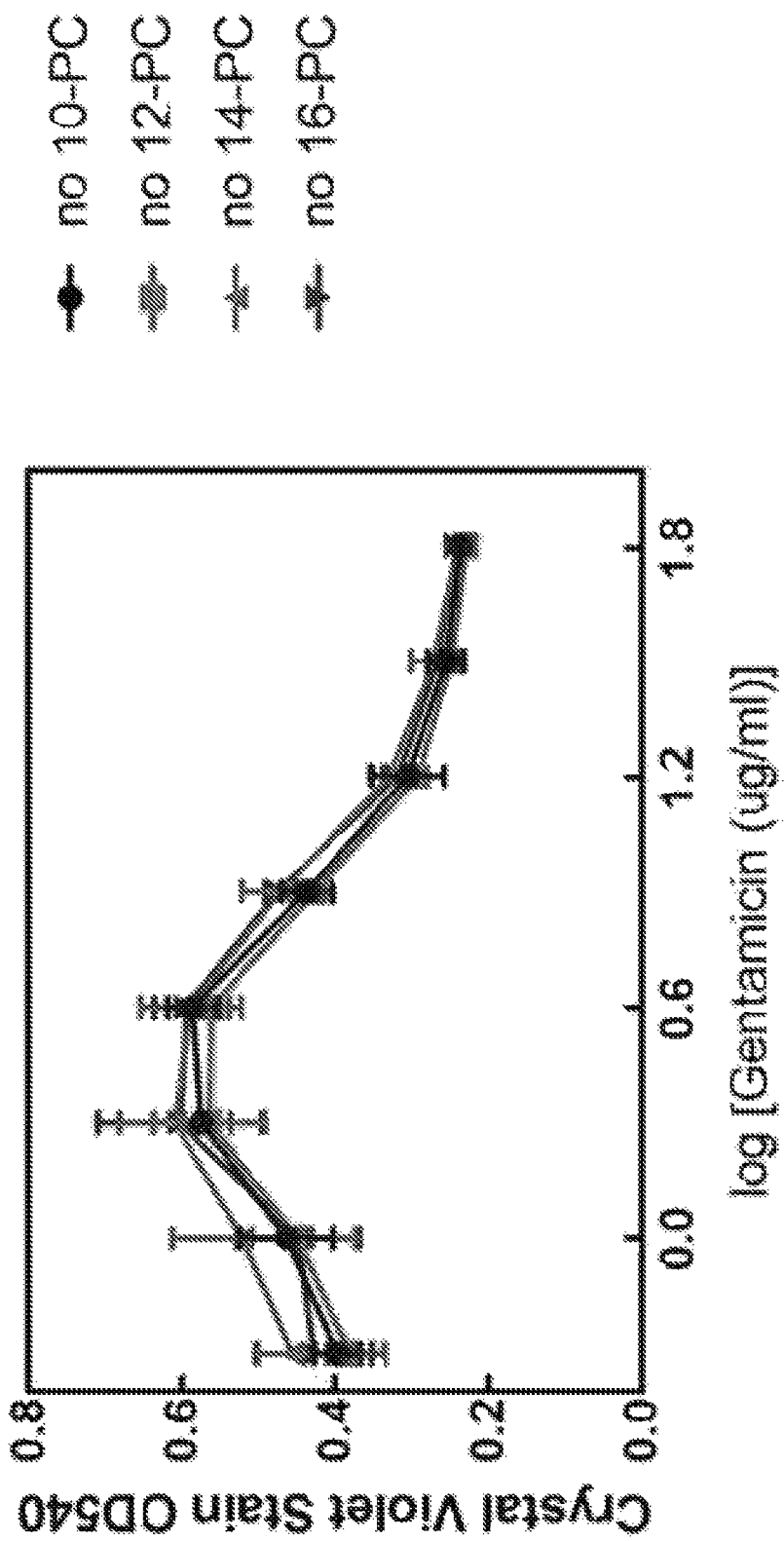
FIGS. 4A, 4B, 4C, and 4D show disruption of preformed P. aeruginosa biofilms 6 h after treatment with gentamicin, either in the absence of a phospholipid (FIG. 4A), or in the presence of a phospholipid at 512, 1024, or 2048 µg/ml concentrations (FIGS. 4B, 4C, and 4D, respectively). The phospholipids investigated are MAPCHO-10, MAPCHO-12, MAPCHO-14, and MAPCHO-16.
Figure 4B:
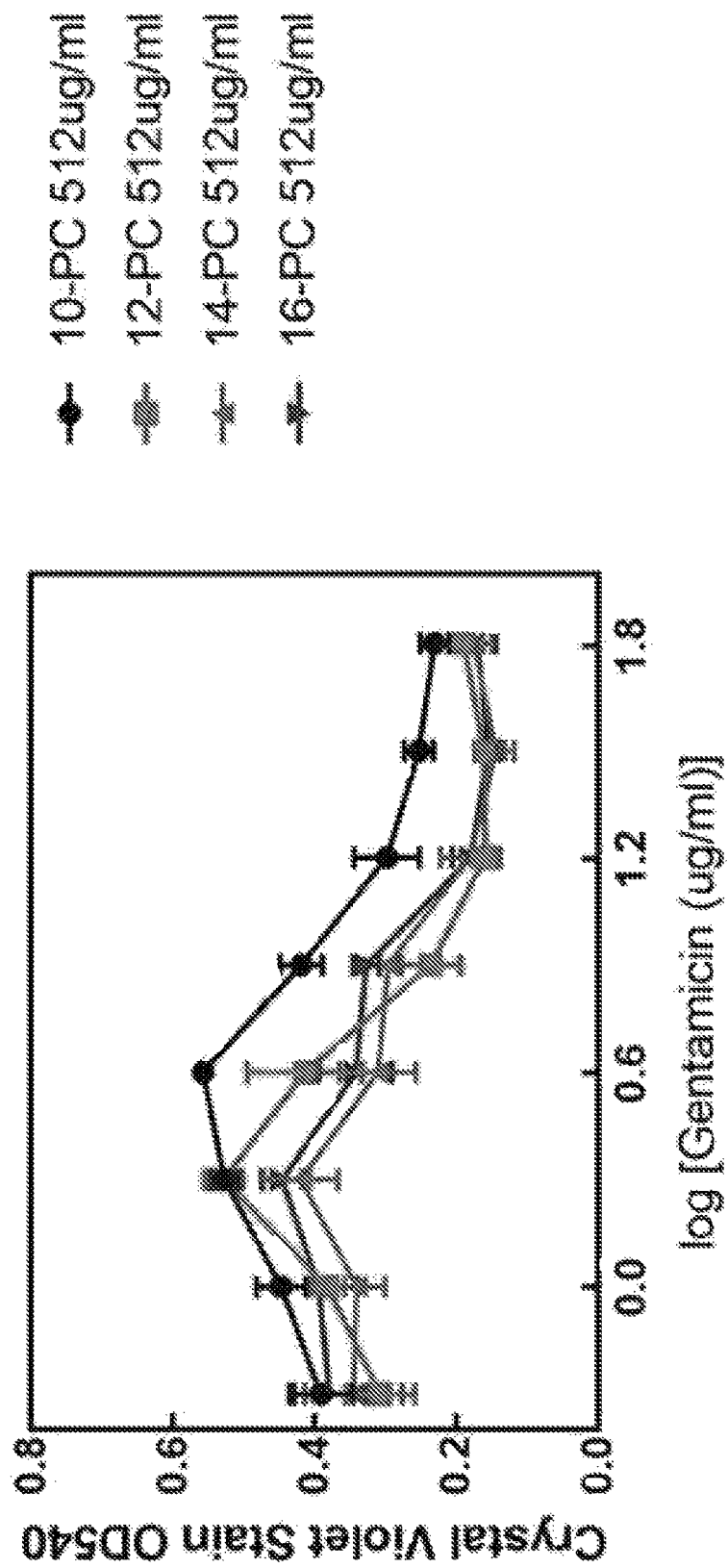
Figure 4C:
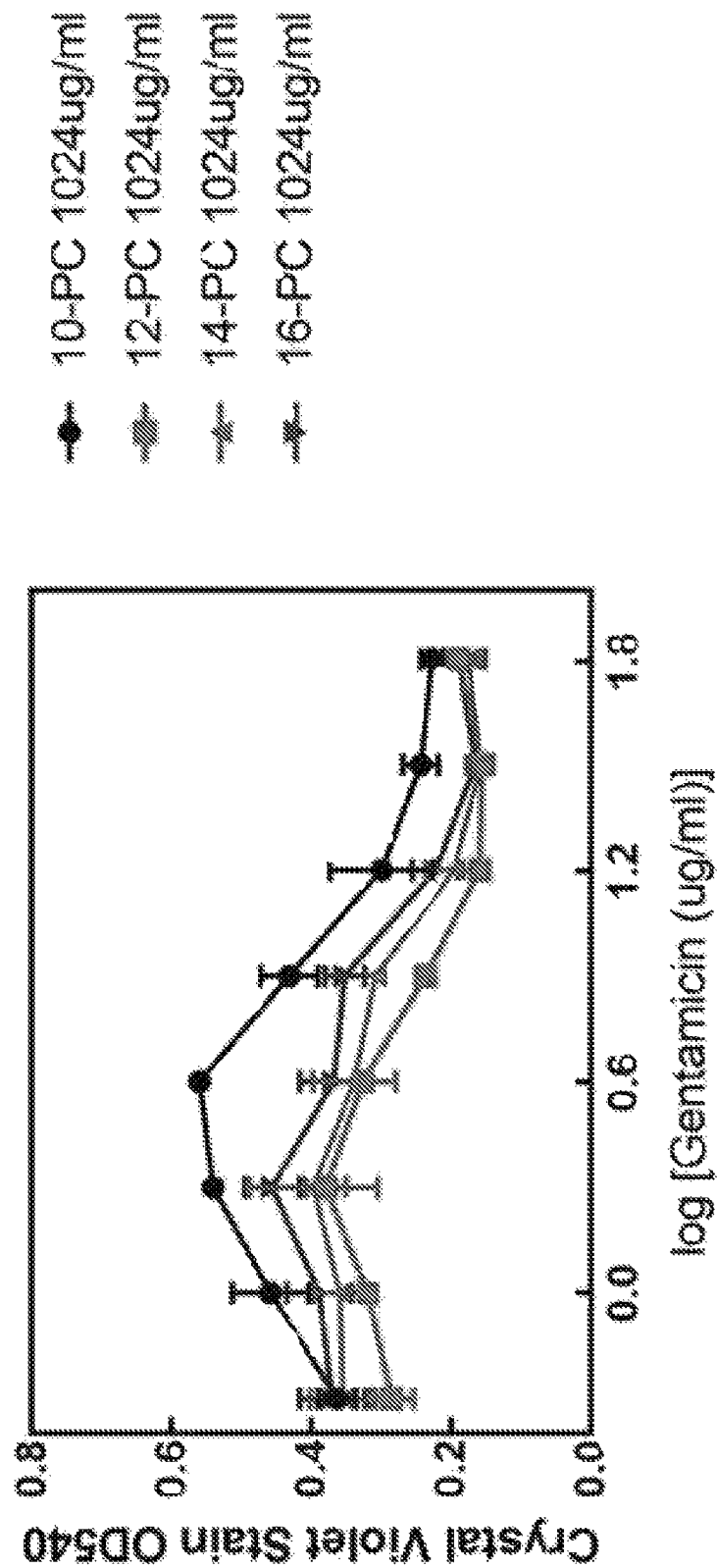
Figure 4D:
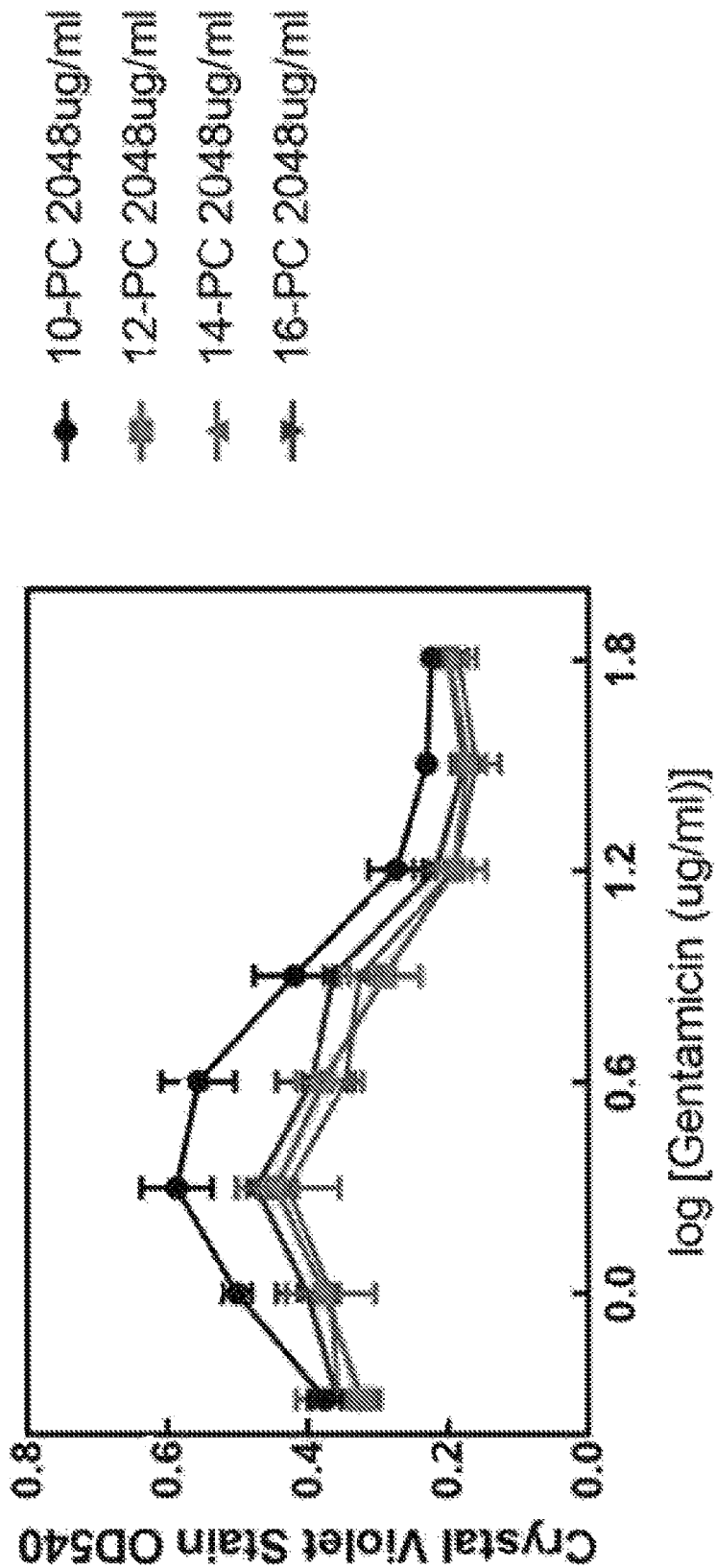

FIGS. 4A, 4B, 4C, and 4D show the results from the tests at the 6 h time point. The results demonstrated that disruption of *P. aeruginosa* biofilms occurs upon treatment with gentamicin in combination with any of MAPCHO-12, MAPCHO-14, or MAPCHO-16, at any of the three phospholipid doses (512 µg/ml, 1024 µg/ml, and 2048 µg/ml). Gentamicin alone did not induce biofilm disruption (FIG. 4A).

Figure 5C:
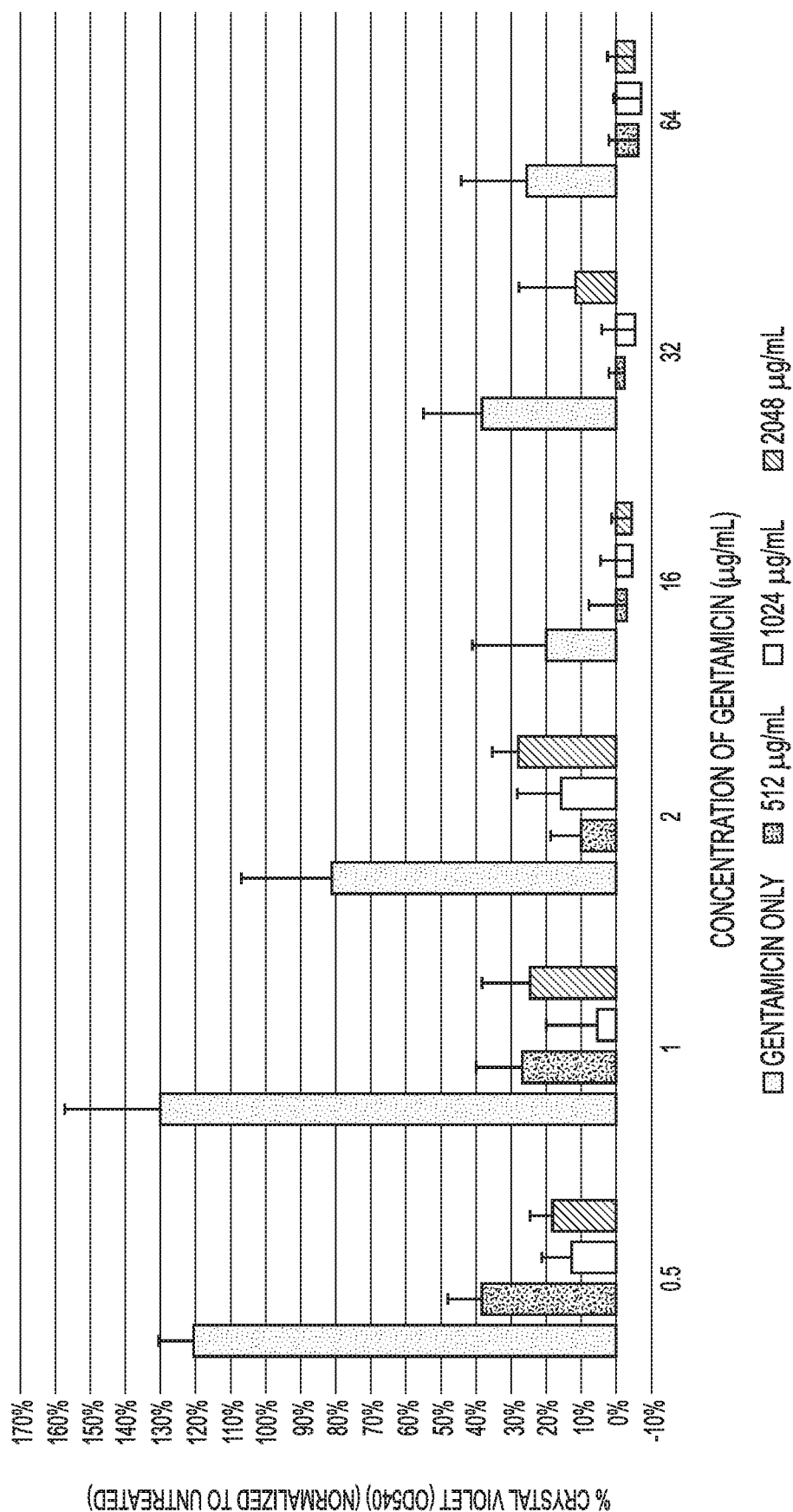

FIGS. 5A, 5B, and 5C show the results from the tests at the 24 h time point. The results demonstrated that nearly complete eradication of *P. aenrginosa* biofilms occurs upon treatment with gentamicin in combination with any of MAPCHO-12, MAPCHO-14, or MAPCHO-16, at any of the three phospholipid doses (512 µg/ml, 1024 µg/ml, and 2048 µg/ml).

Example 4 Phospholipids and Antibiotics Together Inhibit Growth of Planktonic Bacteria We performed in vitro studies of the capacity of phospholipids together with antibiotics to inhibit the growth of planktonic bacteria. The tests were conducted as follows. Freshly grown *P. aeruginosa* was quantitated and placed in 96-well plates together with gentamicin alone, phospholipids plus gentamicin, or control solutions. Four different phospholipids (MAPCHO-10, MAPCHO-12, MAPCHO-14, and MAPCHO-16) were tested at two different phospholipid test concentrations (1024 µg/ml and 2048 µg/ml). After 24 hours at 37 degrees C., media was removed and fresh medium was added and the 96-well plates were incubated at 37 degrees C. for either 6 hours or 24 hours. Bacterial density was then analyzed and measured at OD600.

Figure 6A:
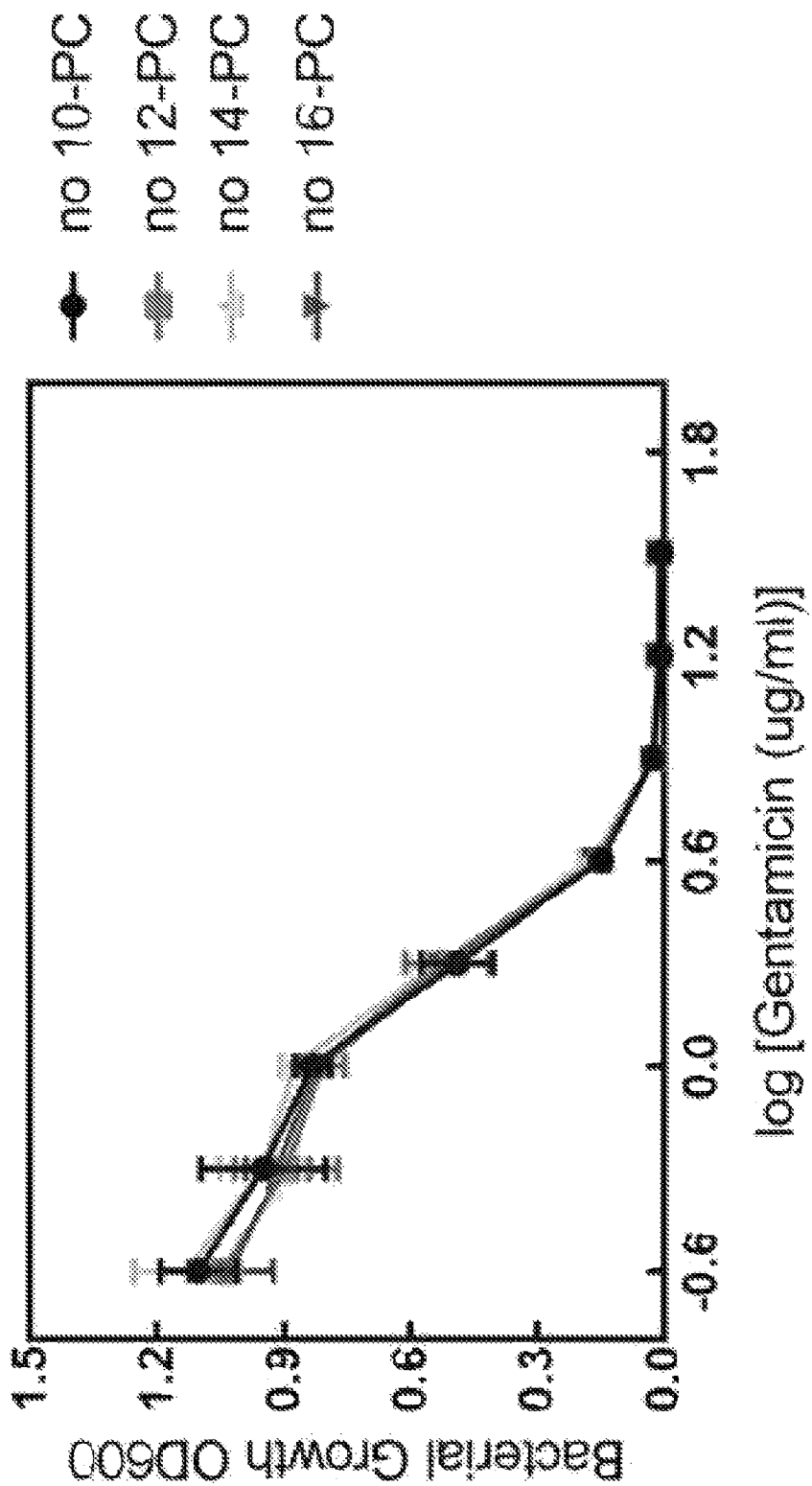
FIGS. 6A, 6B, and 6C show inhibition of the growth of P. aeruginosa 6 h after treatment with gentamicin, either in the absence of a phospholipid (FIG. 6A), or in the presence of a phospholipid at 1024 or 2048 µg/ml concentrations (FIGS. 6B and 6C, respectively). The phospholipids investigated are MAPCHO-10, MAPCHO-12, MAPCHO-14, and MAPCHO-16.
Figure 6B:
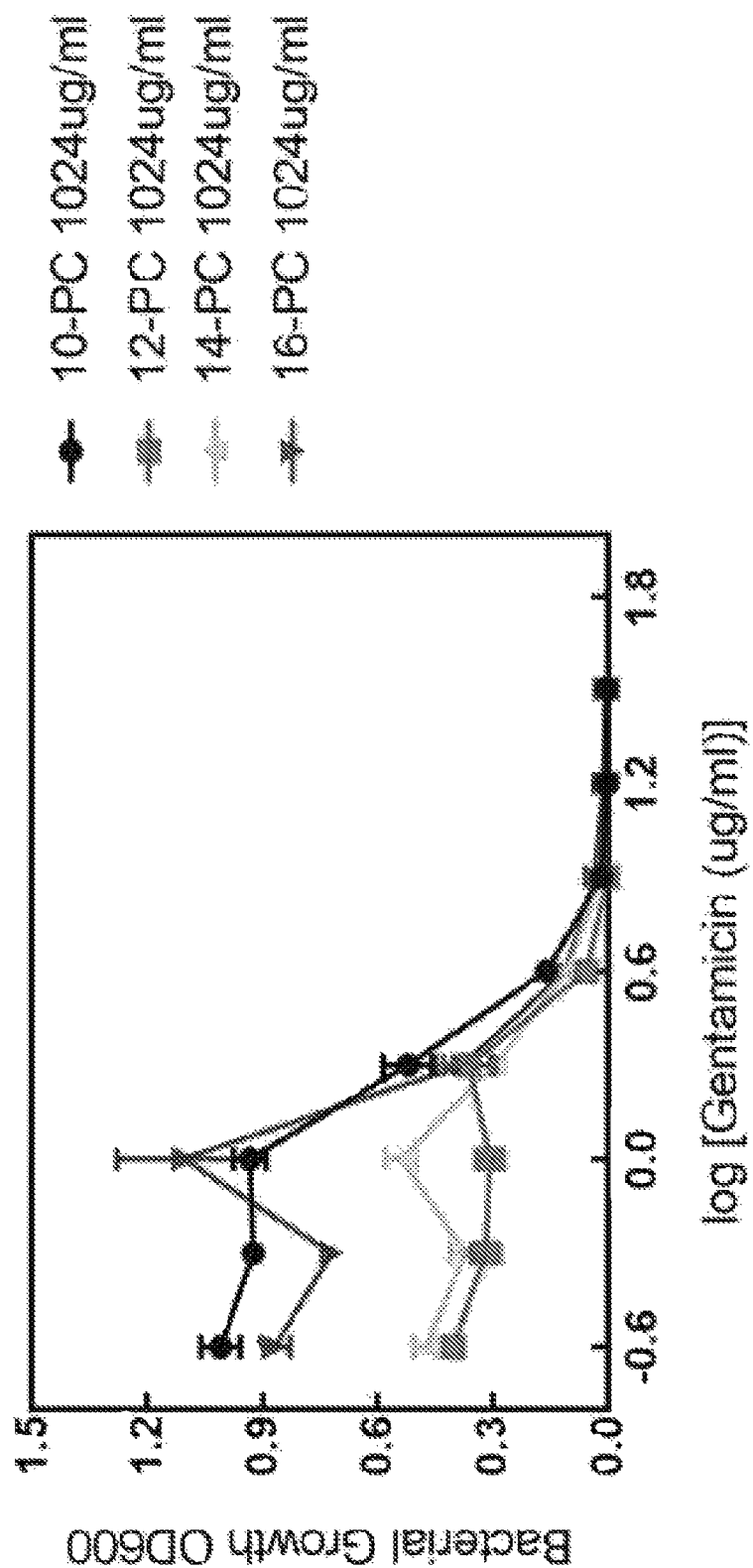
Figure 6C:
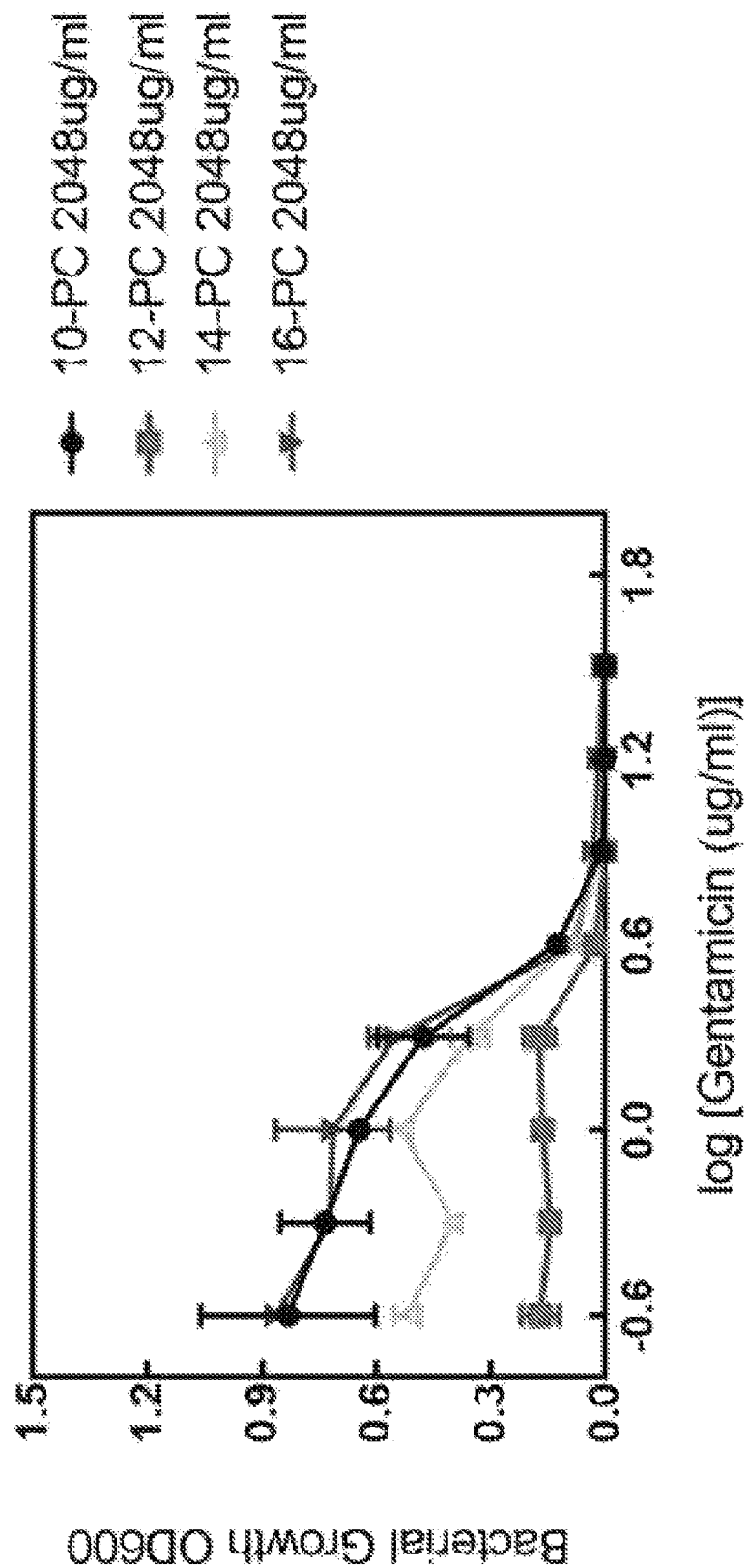

FIGS. 6A, 6B, and 6C show the results from the tests at the 6 h time point. The results demonstrated that moderate inhibition of *P. aeruginosa* growth is observed upon treatment with gentamicin in combination with either MAPCHO-12 or MAPCHO-14, at phospholipid doses of 1024 µg/ml and 2048 µg/ml (FIGS. 6B and 6C), as compared to treatment with gentamicin alone (FIG. 6A).

Figure 7A:
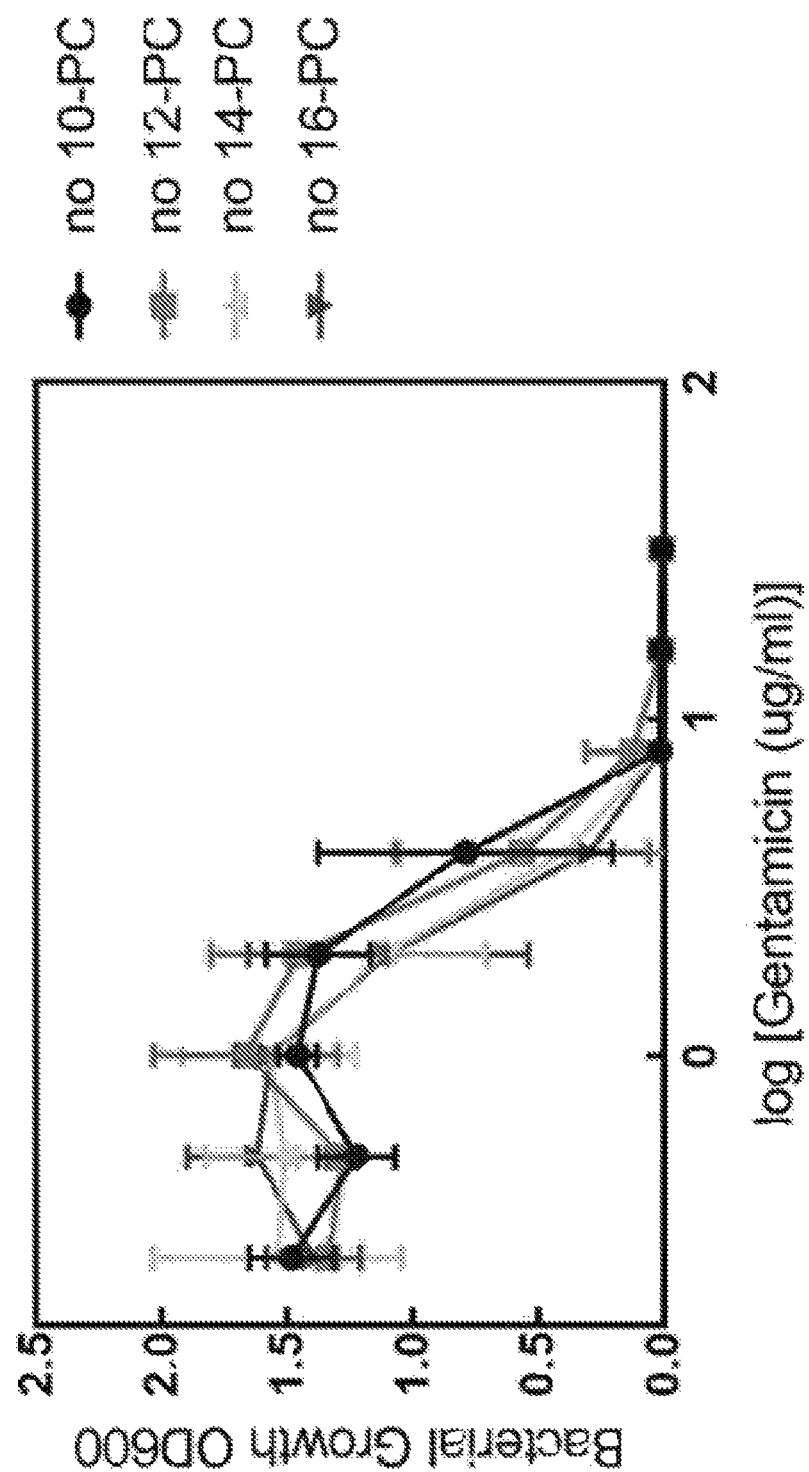
FIGS. 7A, 7B, and 7C show inhibition of P. aeruginosa growth 24 h after treatment with gentamicin, either in the absence of a phospholipid (FIG. 7A), or in the presence of a phospholipid at 1024 or 2048 µg/ml concentrations (FIGS. 7B and 7C, respectively). The phospholipids investigated are MAPCHO-10, MAPCHO-12, MAPCHO-14, and MAPCHO-16.
Figure 7B:
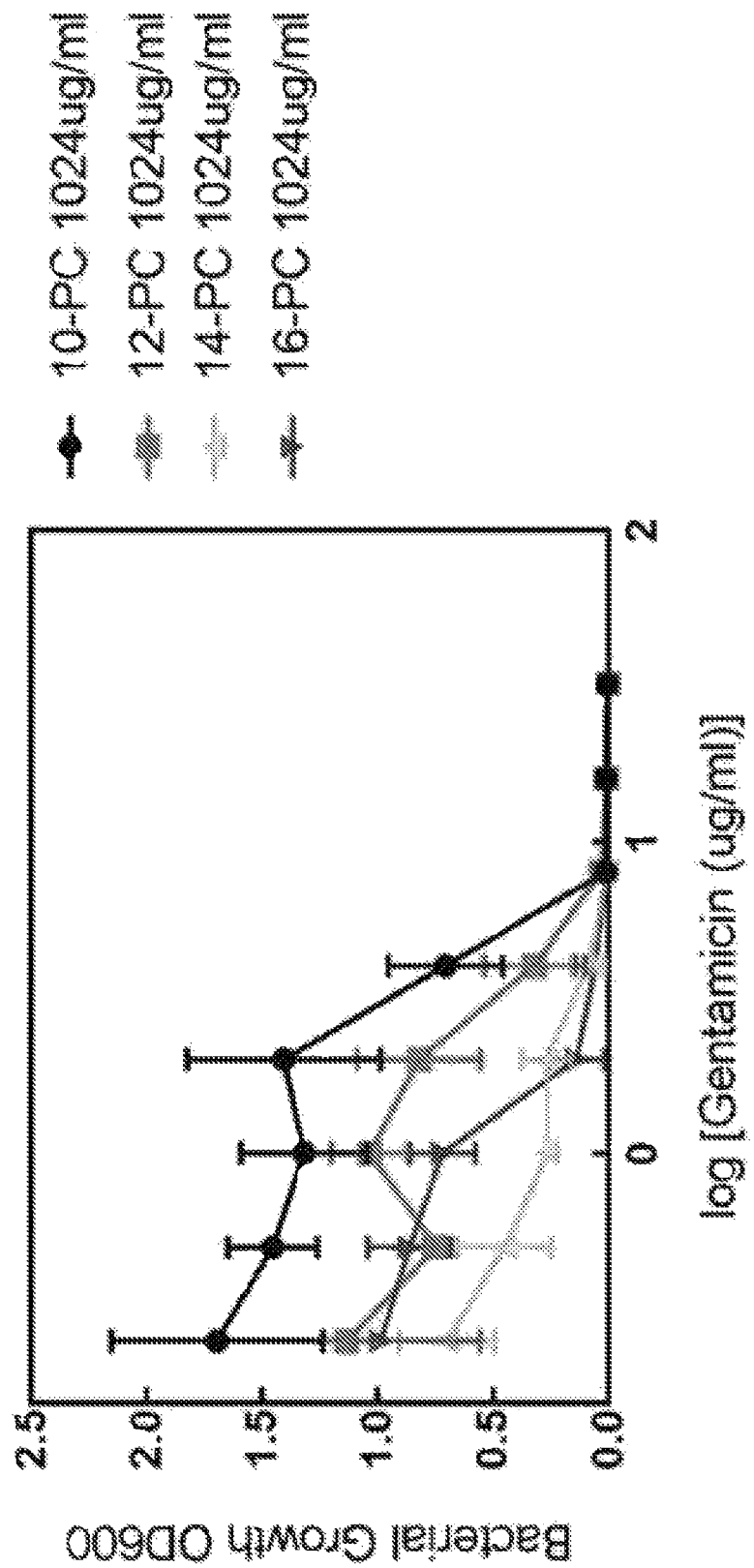
Figure 7C:
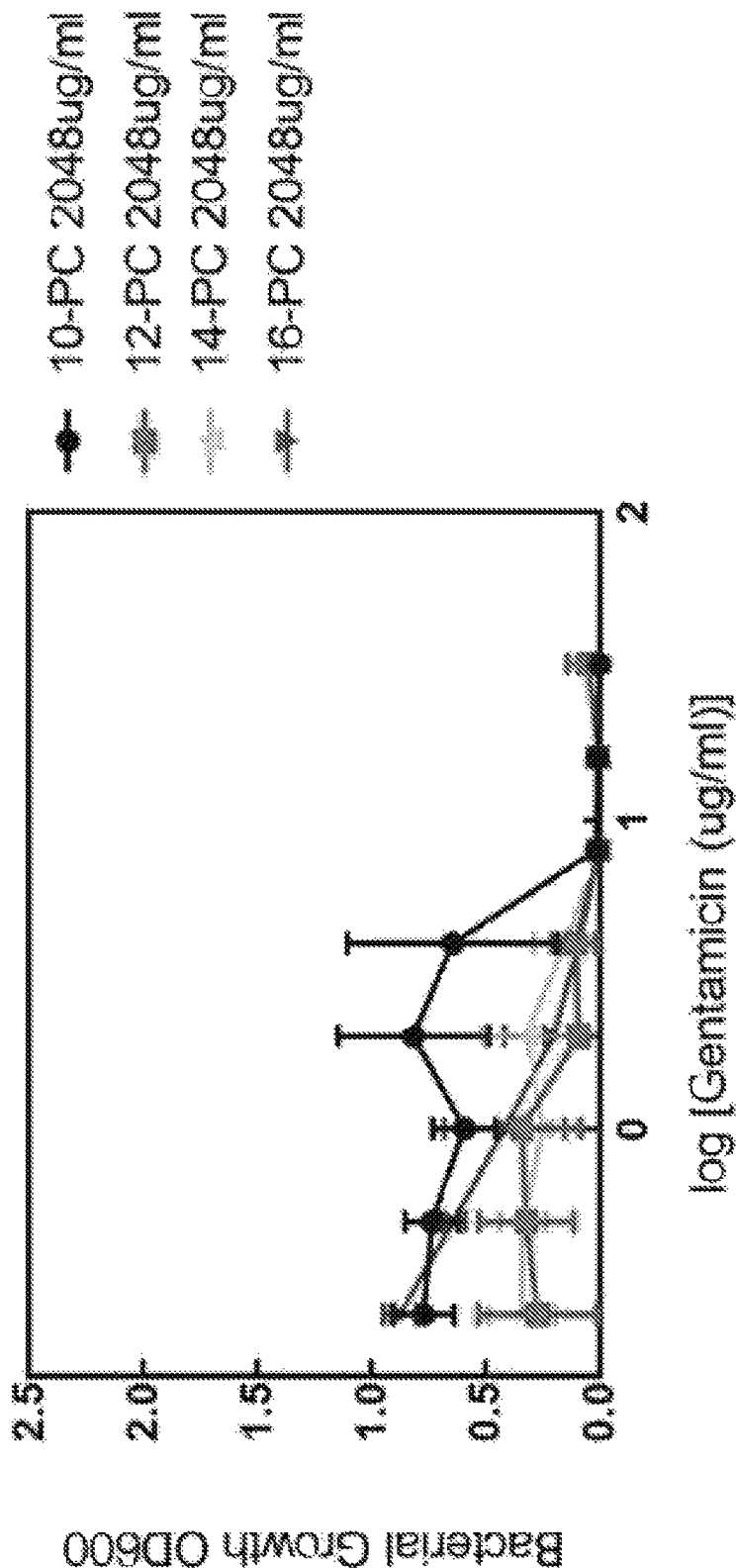

FIGS. 7A, 7B, and 7C show the results from the tests at the 24 h time point. The results demonstrated that significant inhibition of *P. aeruginosa* growth is observed upon treatment with gentamicin in combination with MAPCHO-14 at phospholipid doses of 1024 µg/ml and 2048 µg/ml (FIGS. 7B and 7C), as compared to treatment with gentamicin alone (FIG. 7A). Similarly, significant inhibition is observed upon treatment with gentamicin in combination with MAPCHO-12 at the highest phospholipid dose of 2048 µg/ml (FIG. 7C), as compared to treatment with gentamicin alone.

Example 5 Phospholipids and Antibiotics Together Prevent the Formation of Biofilms We performed in vitro tests of the capacity of phospholipids together with antibiotics to prevent formation of biofilms. Freshly grown *P. aeruginosa* was quantitated and placed in 96-well plates together with gentamicin alone, phospholipids plus gentamicin, or control solutions. Four different phospholipids (MAPCHO-10, MAPCHO-12, MAPCHO-14, and MAPCHO-16) were tested at two different phospholipid test concentrations (1024 µg/ml and 2048 µg/ml). After 24 hours at 37 degrees C., the fluids were removed and the wells stained with crystal violet, and then the density of crystal violet in the wells was quantitated.

Figure 8A:
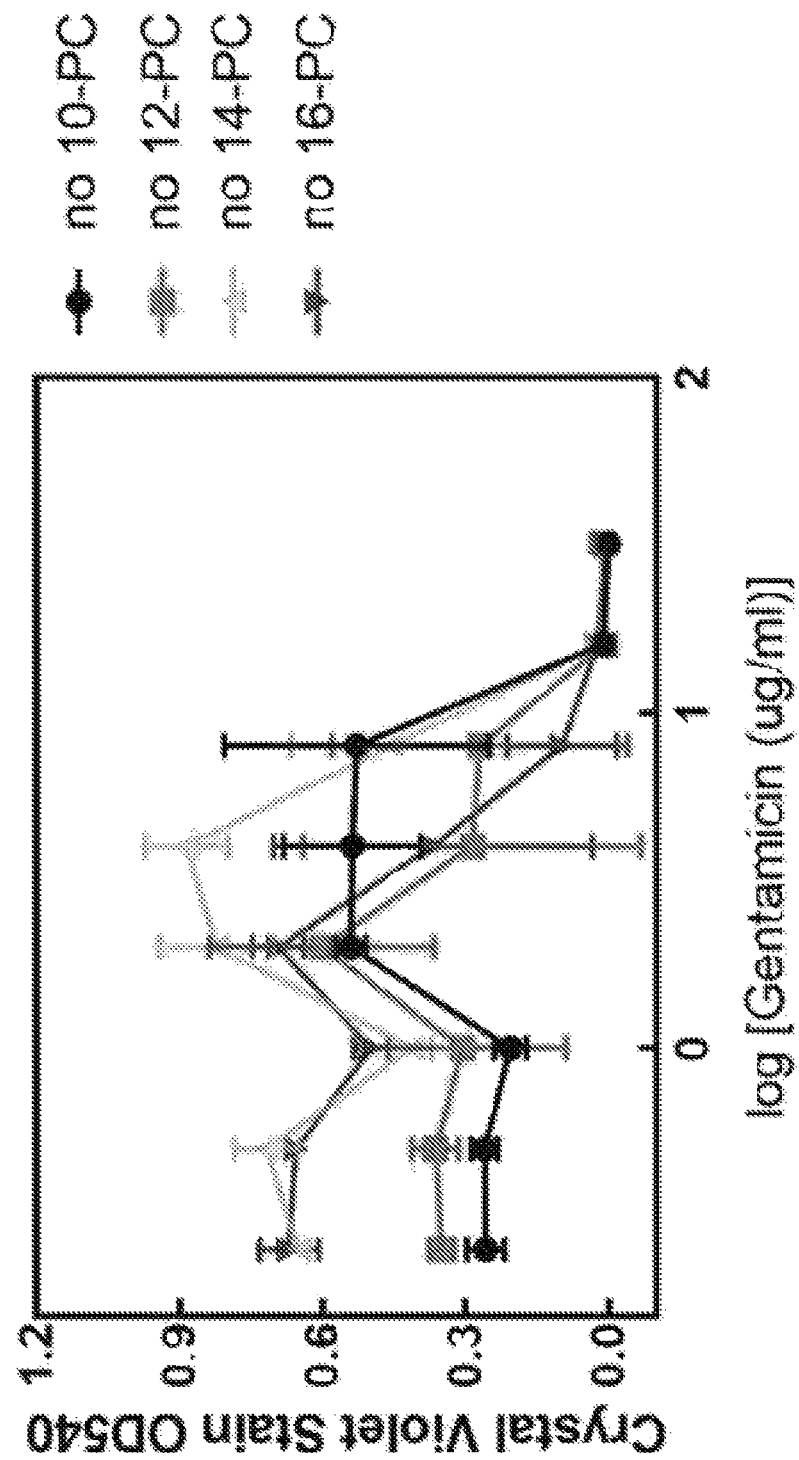
FIGS. 8A, 8B, and 8C show prevention of P. aeruginosa biofilm formation 24 h after treatment with gentamicin, either in the absence of a phospholipid (FIG. 8A), or in the presence of a phospholipid at 1024 or 2048 µg/ml concentrations (FIGS. 8B and 8C, respectively). The phospholipids investigated are MAPCHO-10, MAPCHO-12, MAPCHO-14, and MAPCHO-16.
Figure 8B:
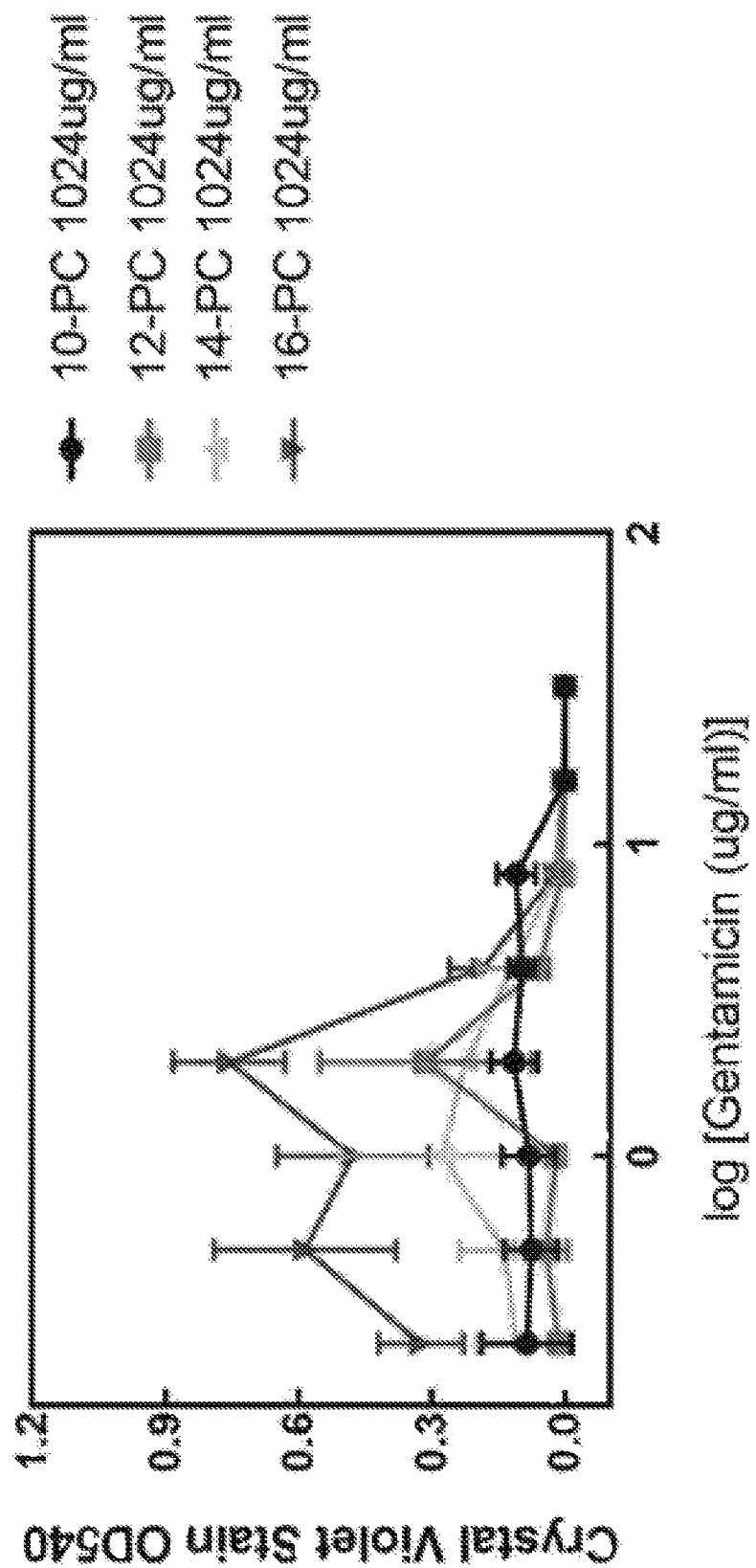
Figure 8C:
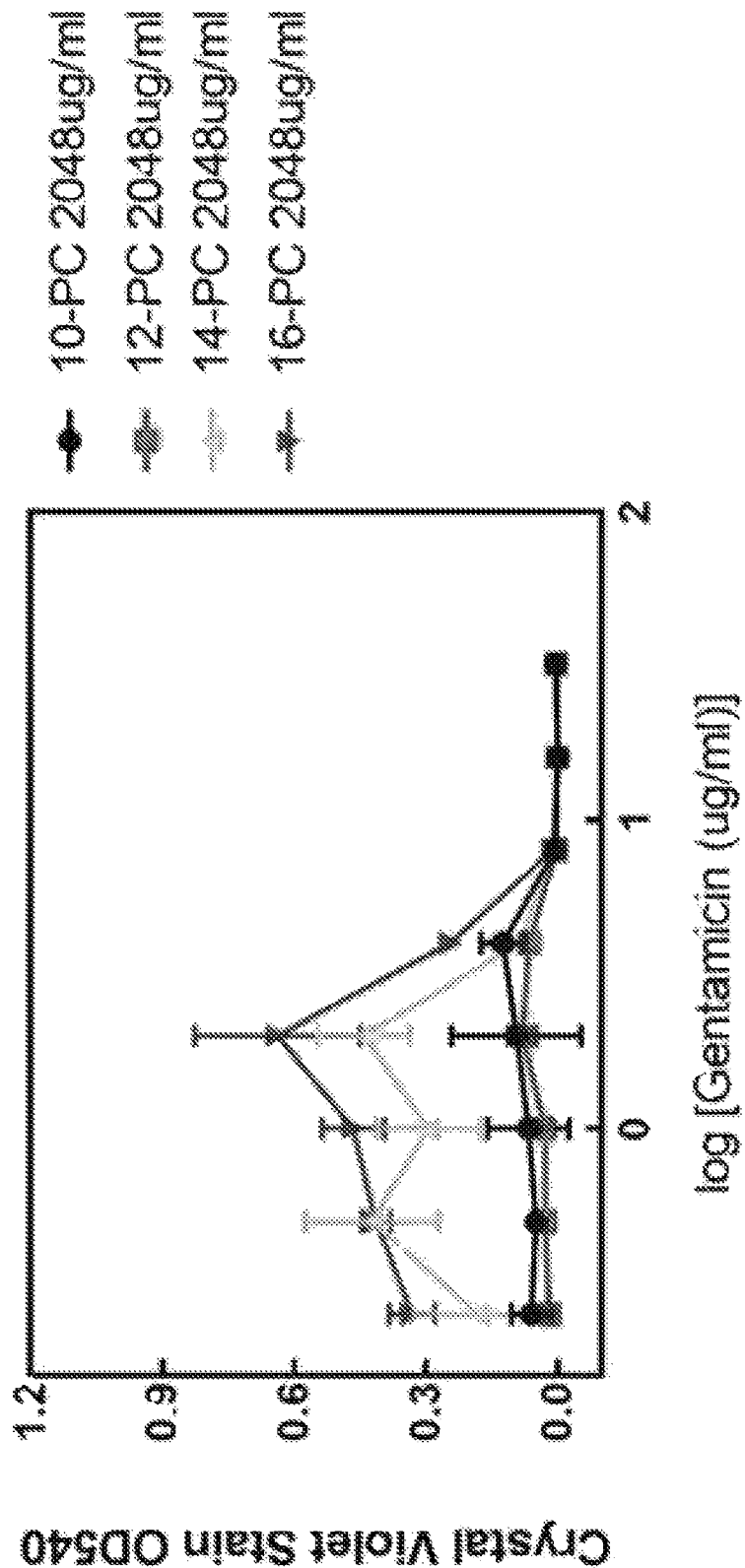

FIGS. 8A, 8B, and 8C show the results from the tests. FIG. 8A shows that gentamicin alone was unable to prevent *P. aeruginosa* biofilm formation. FIGS. 8B and 8C show that the combinations of gentamicin with any of MAPCHO-12, MAPCHO-14, or MAPCHO-16, at either tested phospholipid concentration, are effective at preventing *P. aeruginosa* biofilm formation.

Example 6 Phospholipids and Antibiotics Together Inhibit the Growth of Bacteria We performed in vitro studies of the capacity of phospholipids together with antibiotics to prevent bacterial growth. Freshly grown *P. aeruginosa* was quantitated and placed in 96-well plates together with gentamicin alone, phospholipids plus gentamicin, or control solutions. Three different phospholipids (MAPCHO-12, MAPCHO-14, and MAPCHO-16) were tested at three different phospholipid test concentrations (512 µg/ml, 1024 µg/ml, and 2048 µg/ml). After 24 hours at 37 degrees C., bacterial density was then analyzed and measured at OD600.

Figure 9A:
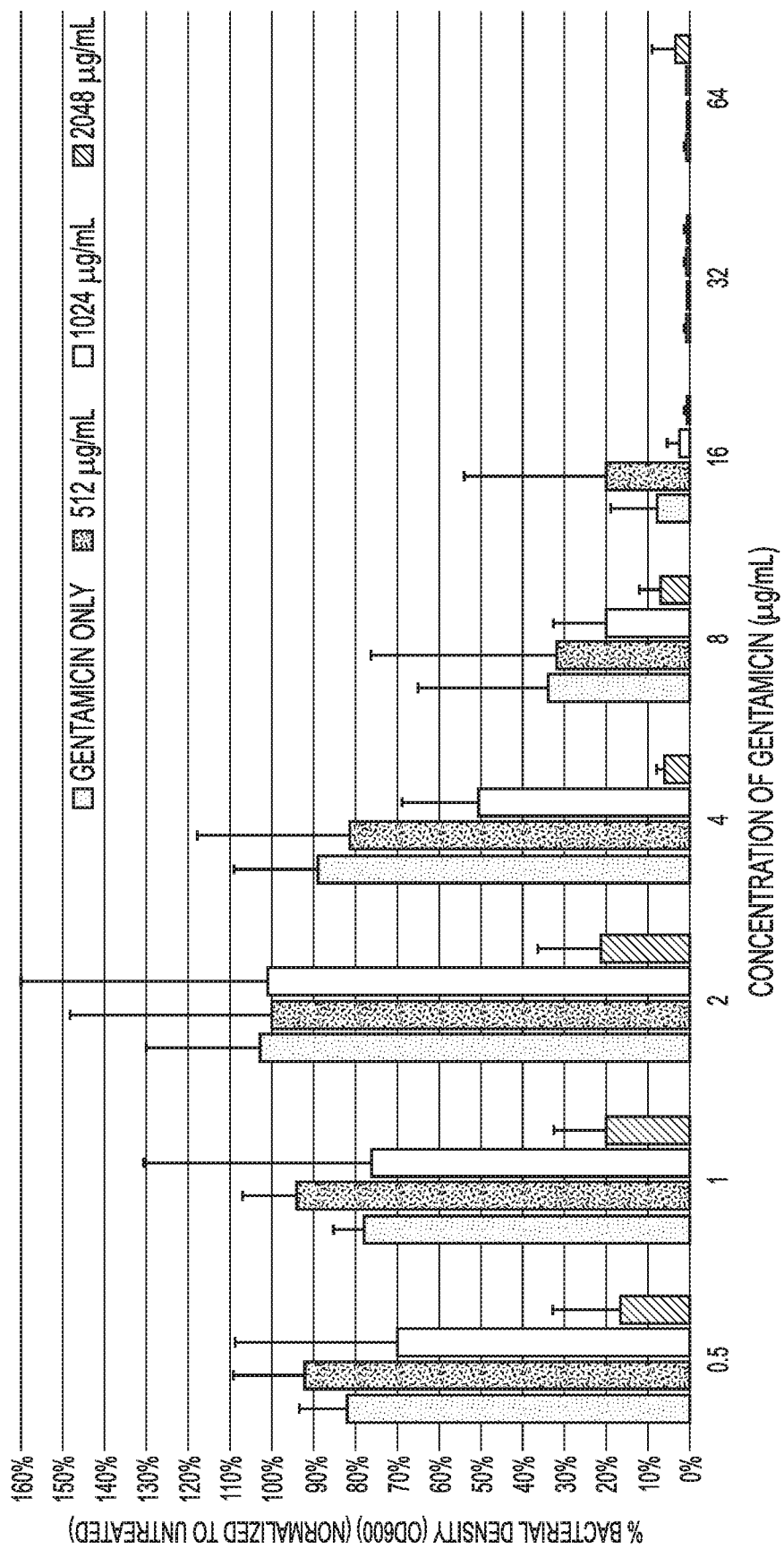
FIGS. 9A, 9B, and 9C show prevention of P. aeruginosa growth in biofilms 24 h after treatment with gentamicin, either in the absence of a phospholipid or in the presence of a phospholipid at 512, 1024 or 2048 µg/ml concentrations. The phospholipids investigated are MAPCHO-12 (FIG. 9A), MAPCHO-14 (FIG. 9B), and MAPCHO-16 (FIG. 9C).
Figure 9B:
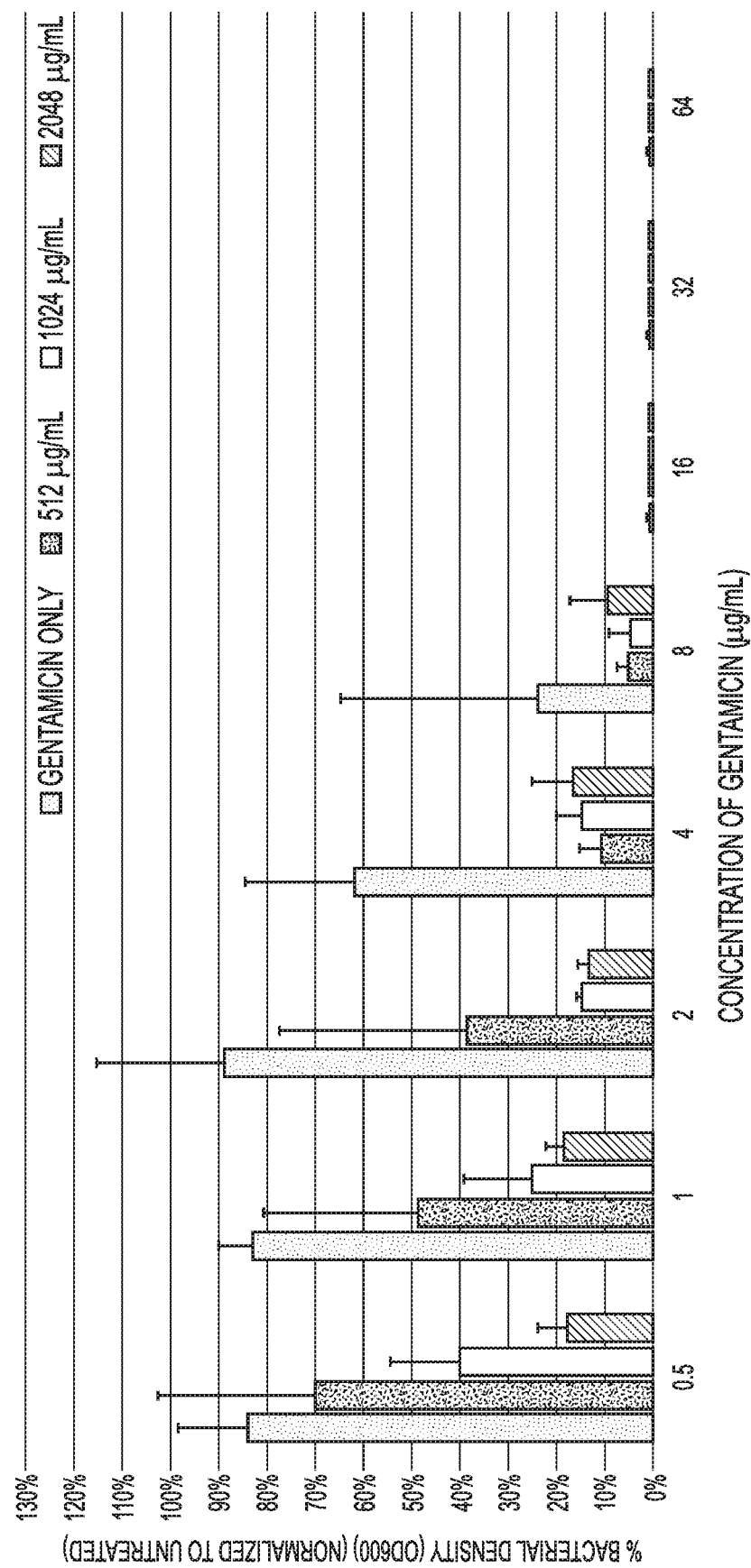
Figure 9C:
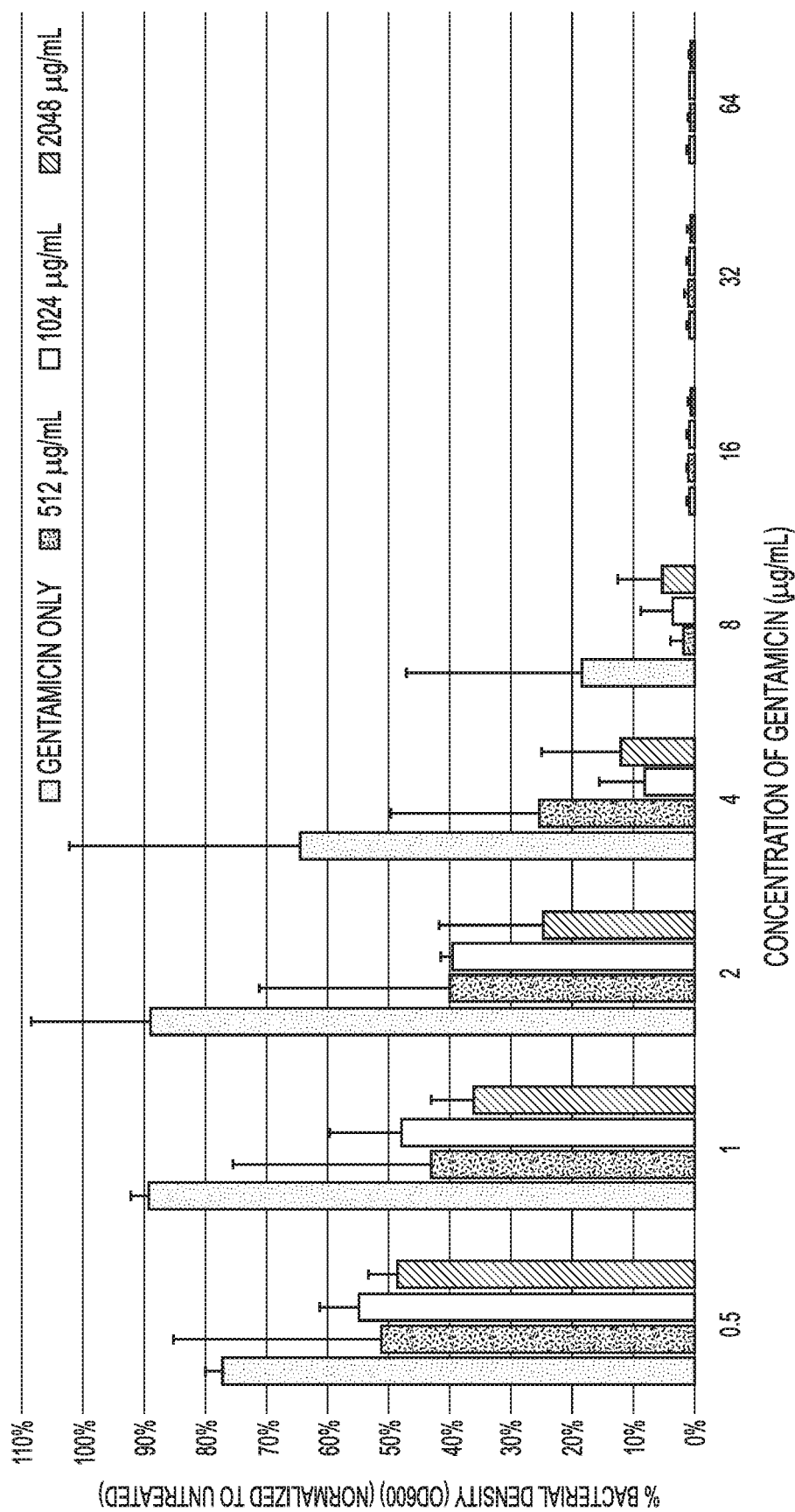

FIGS. 9A, 9B, and 9C show the results from the tests for MAPCHO-12, MAPCHO-14, and MAPCHO-16, respectively. FIGS. 9B and 9C show that MAPCHO-14 and MAPCHO-16 were each more effective in combination with gentamicin to inhibit *P. aeruginosa* bacterial growth relative to treatment with gentamicin alone.

Example 7 Phospholipids and Antibiotics Together Inhibit Further Growth of Biofilms We performed in vitro studies of the capacity of phospholipids together with antibiotics to eradicate preformed bacterial biofilms. The tests were conducted as follows. Biofilm formation was obtained by culturing *P. aeruginosa* in cation-adjusted Mueller Hinton Broth after incubation at 37 degrees C. for 24 hours in 96 well plates. The medium was then removed and replaced by treatment solutions of gentamicin, phospholipids plus gentamicin, or control solutions. Four different phospholipids (MAPCHO-10, MAPCHO-12, MAPCHO-14, and MAPCHO-16) were tested at three different phospholipid test concentrations (512 µg/ml, 1024 µg/ml, and 2048 µg/ml). After 24 hours at 37 degrees C., media was removed and fresh medium was added and the 96-well plates were incubated at 37 degrees C. for 6 hours. Bacterial density was then analyzed and measured at OD600.

Figure 10A:
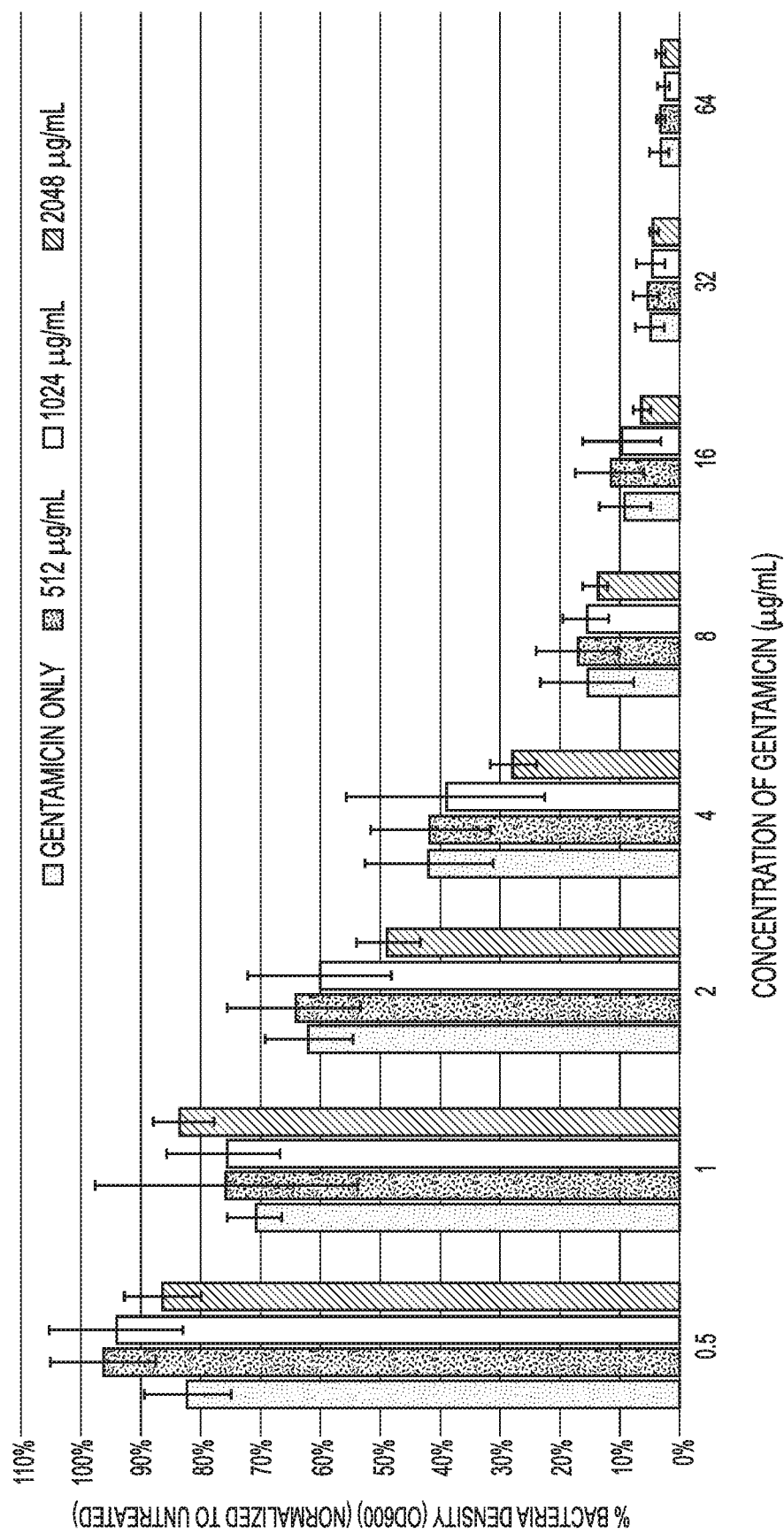
FIGS. 10A, 10B, 10C, and 10D show inhibition of bacterial growth (bacteria density) of P. aeruginosa in preformed biofilm 6 h after treatment with gentamicin, either in the absence of a phospholipid, or in the presence of a phospholipid at 512, 1024, or 2048 µg/ml concentrations. The phospholipids investigated are MAPCHO-10 (FIG. 10A), MAPCHO-12 (FIG. 10B), MAPCHO-14 (FIG. 10C), and MAPCHO-16 (FIG. 10D).
Figure 10B:
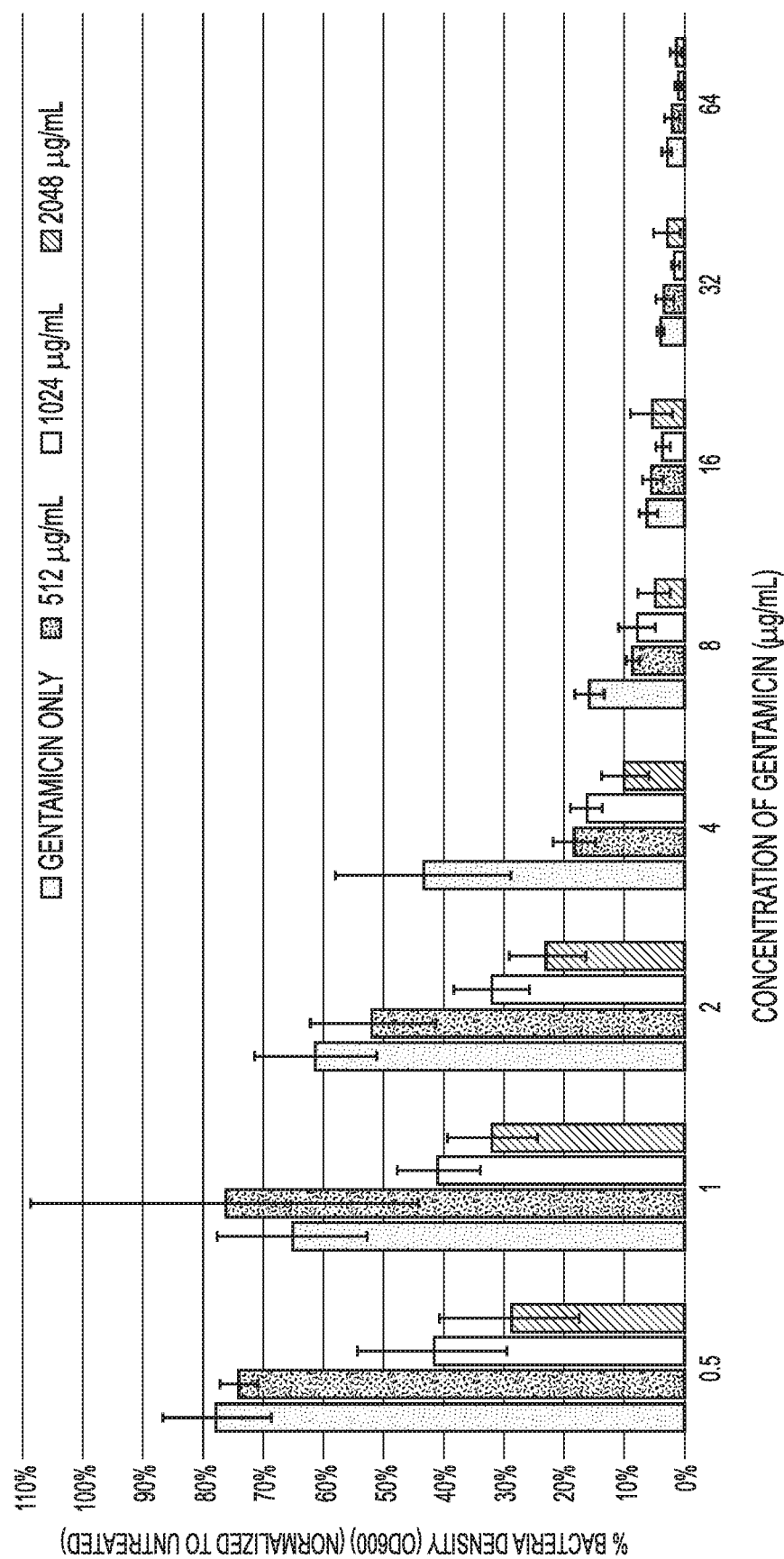
Figure 10C:
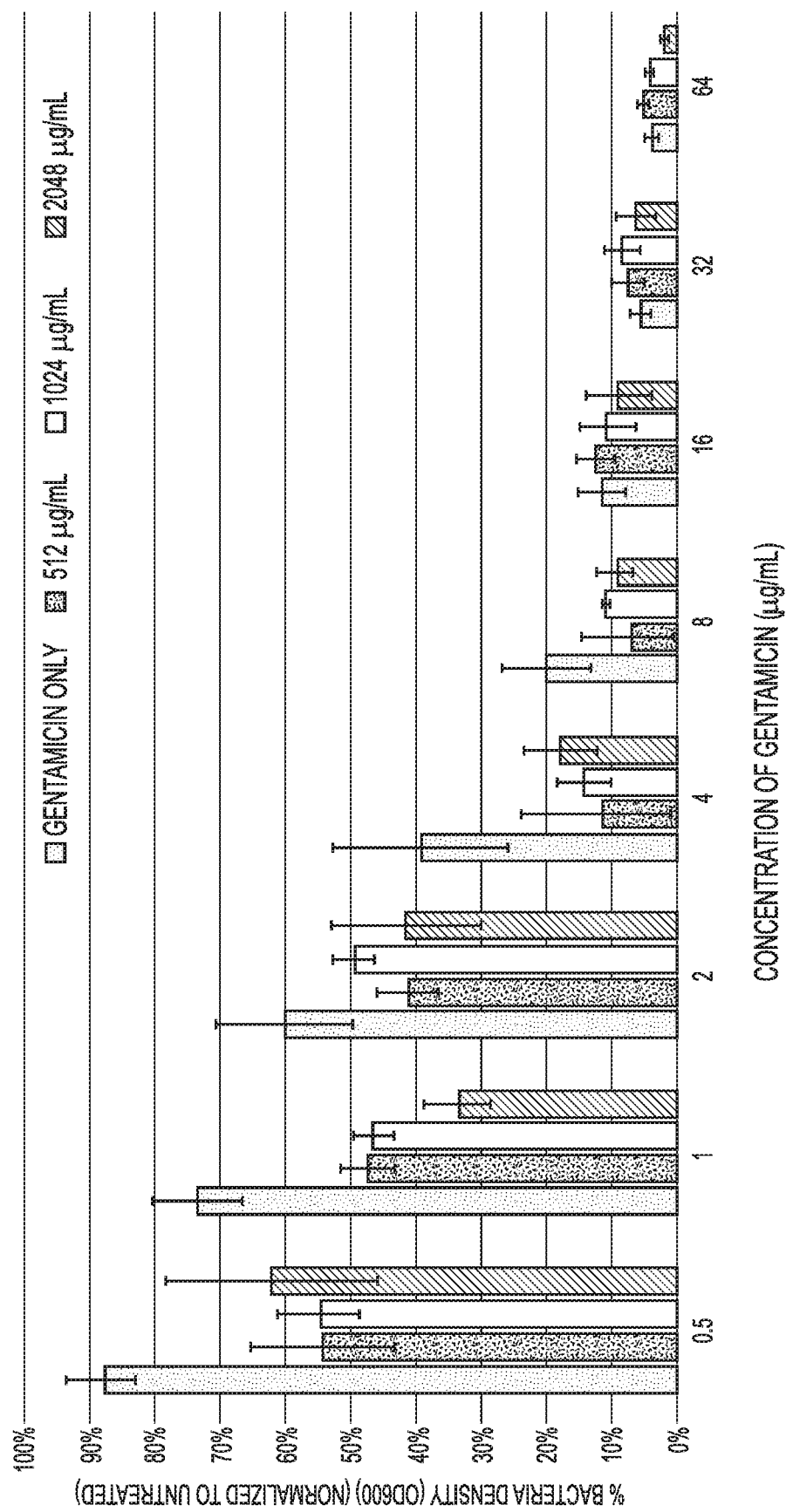
Figure 10D:
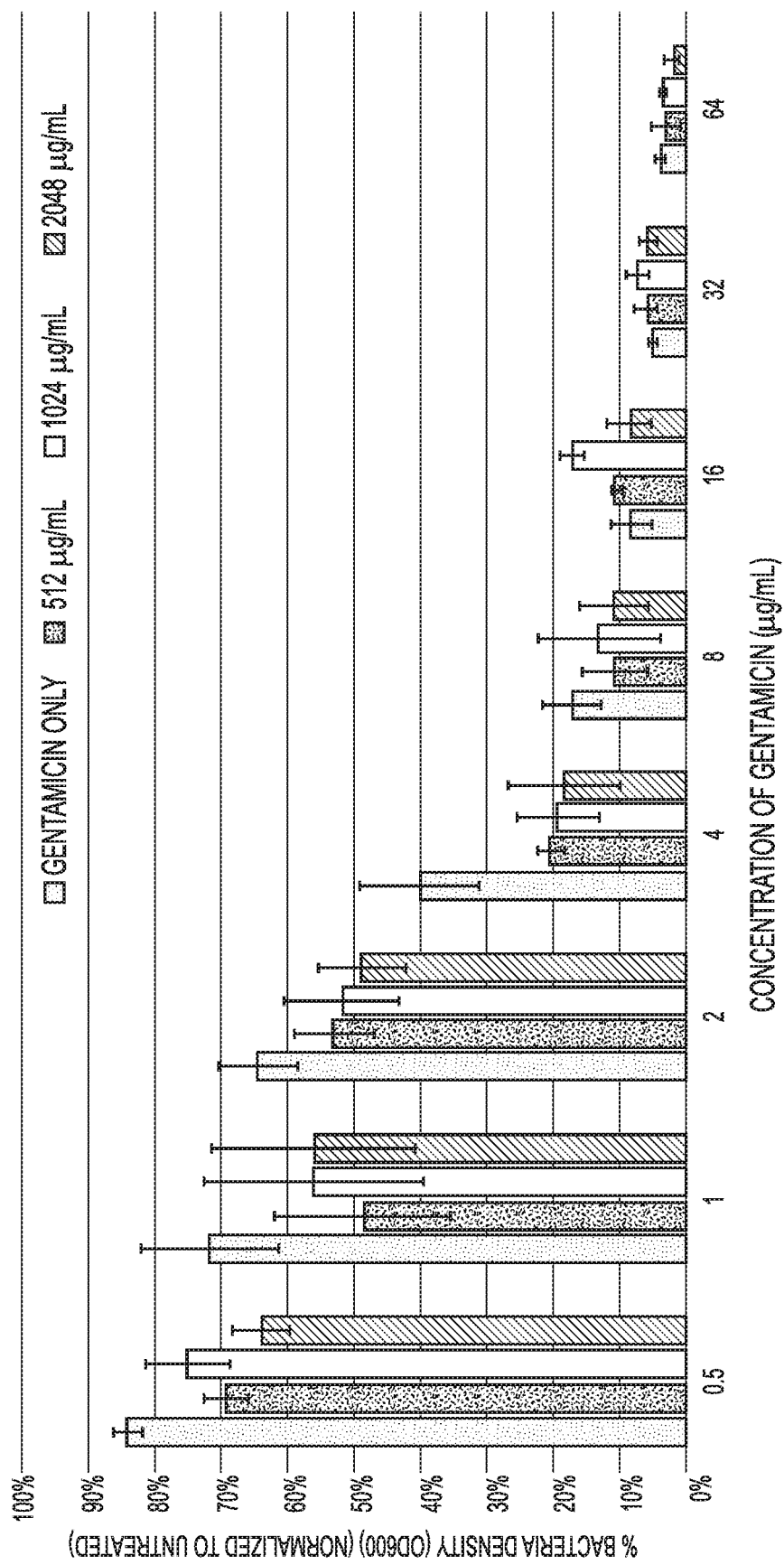

FIGS. 10A, 10B, 10C, and 10D show the results from the tests for MAPCHO-10, MAPCHO-12, MAPCHO-14, and MAPCHO-16, respectively. FIGS. 10B, 10C, and 10D show that any of MAPCHO-12, MAPCHO-14, and MAPCHO-16, proved to be more effective in combination with gentamicin to inhibit *P. aeruginosa* bacterial growth relative to treatment with gentamicin alone.

Example 8 Phospholipids and Antibiotics Together Inhibit Growth of Planktonic Bacteria We performed in vitro studies of the capacity of phospholipids together with antibiotics to inhibit the growth of planktonic bacteria. The tests were conducted as follows. Freshly grown *S. aureus* was quantitated and placed in 96-well plates together with gentamicin alone, phospholipids plus gentamicin, or control solutions. Two different phospholipids (MAPCHO-10 and MAPCHO-12) were tested at three different phospholipid test concentrations (256 µg/ml, 512 µg/ml, and 1024 µg/ml). After 24 hours at 37 degrees C., media was removed and fresh medium was added and the 96-well plates were incubated at 37 degrees C. for 6 hours. Bacterial density was then analyzed and measured at OD600.

Figure 11A:
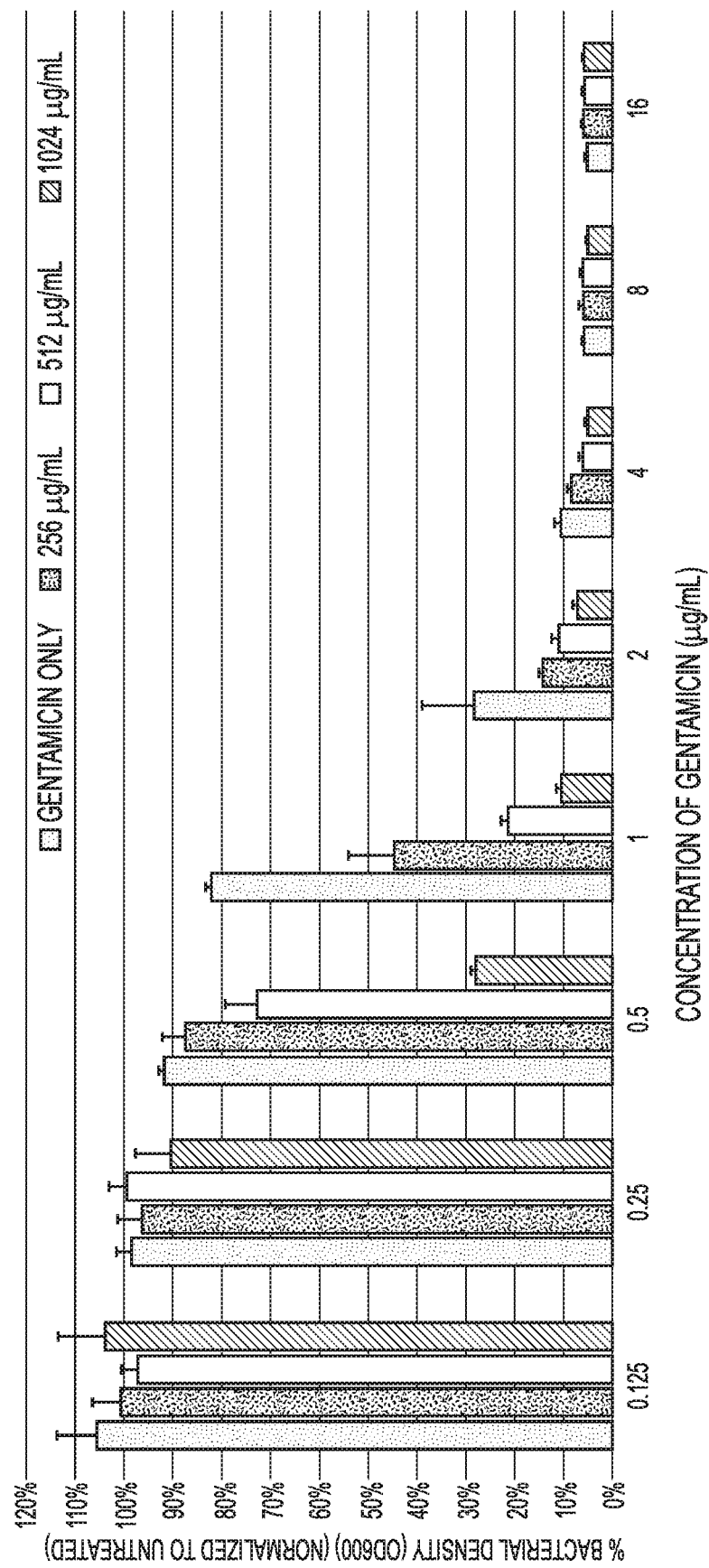
FIGS. 11A and 11B show inhibition of bacterial growth (bacteria density) of S. aureus 6 h after treatment with gentamicin, either in the absence of a phospholipid, or in the presence of a phospholipid at 256, 512, or 1024 µg/ml concentrations. The phospholipids investigated are MAPCHO-10 (FIG. 11A) and MAPCHO-12 (FIG. 11B).
Figure 11B:
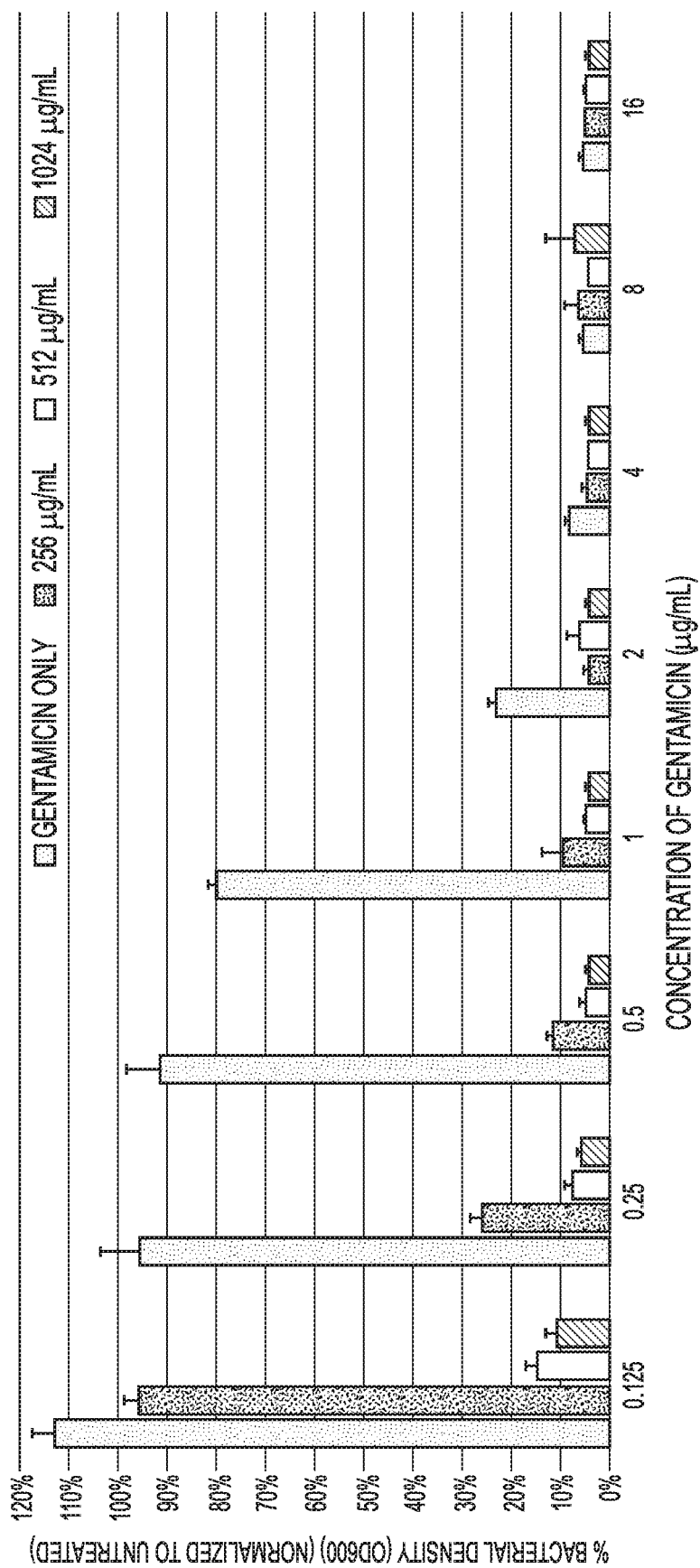

FIGS. 11A and 11B show the results from the tests for MAPCHO-10 and MAPCHO-12, respectively. The results demonstrated that moderate inhibition of S. aureus growth is observed upon treatment with gentamicin in combination with MAPCHO-10 as compared to treatment with gentamicin alone (FIG. 11A), while strong inhibition of S. aureus growth is observed upon treatment with gentamicin in combination with MAPCHO-12 as compared to treatment with gentamicin alone (FIG. 11B).

Example 9 Phospholipids and Antibiotics Together Prevent the Formation of Biofilms We performed in vitro tests of the capacity of phospholipids together with antibiotics to prevent formation of biofilms. Freshly grown S. aureus was quantitated and placed in 96-well plates together with gentamicin alone, phospholipids plus gentamicin, or control solutions. Two different phospholipids (MAPCHO-10 and MAPCHO-12) were tested at three different phospholipid test concentrations (256 µg/ml, 512 µg/ml, and 1024 µg/ml). After 6 hours at 37 degrees C., the fluids were removed and the wells stained with crystal violet, and then the density of crystal violet in the wells was quantitated.

Figure 12A:
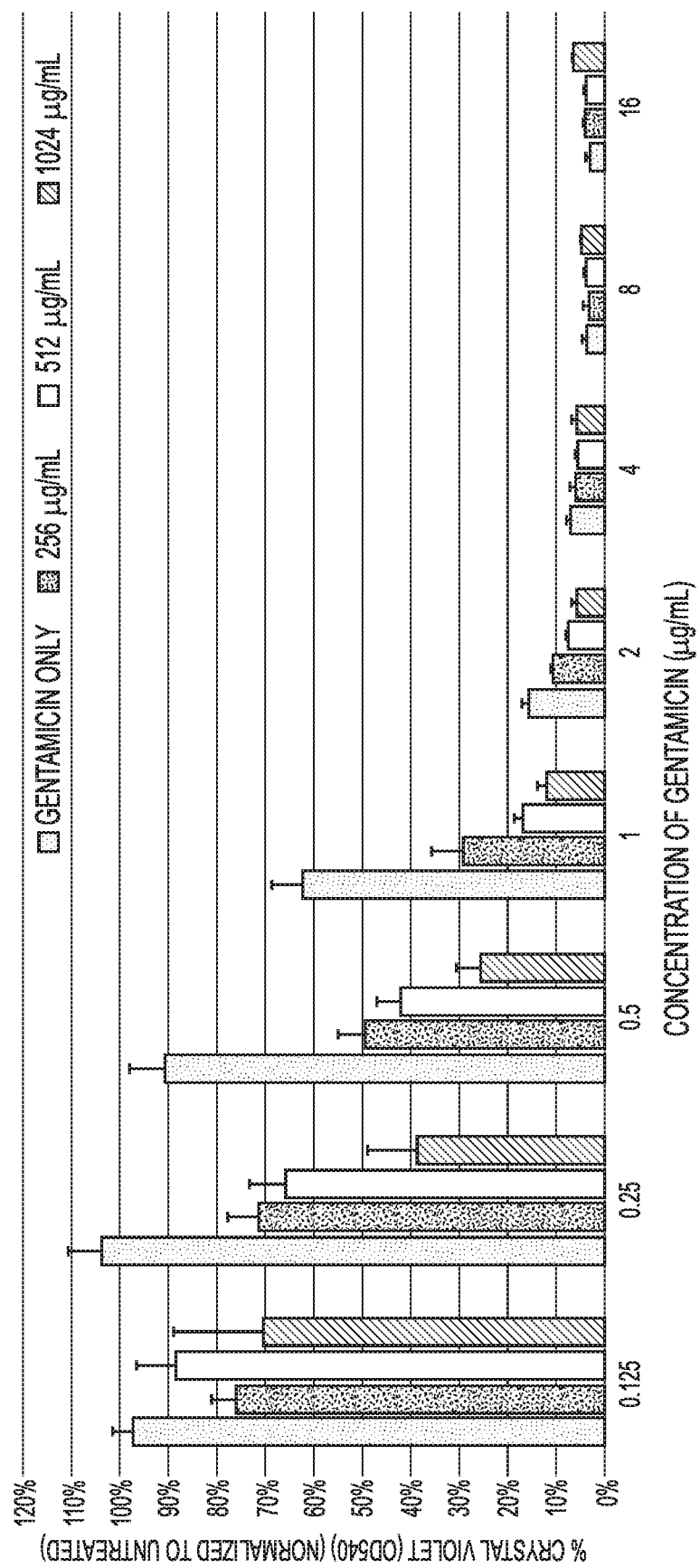
FIGS. 12A and 12B show prevention of S. aureus biofilm formation 6 h after treatment with gentamicin, either in the absence of a phospholipid, or in the presence of a phospholipid at 256, 512, or 1024 µg/ml concentrations. The phospholipids investigated are MAPCHO-10 (FIG. 12A) and MAPCHO-12 (FIG. 12B).
Figure 12B:
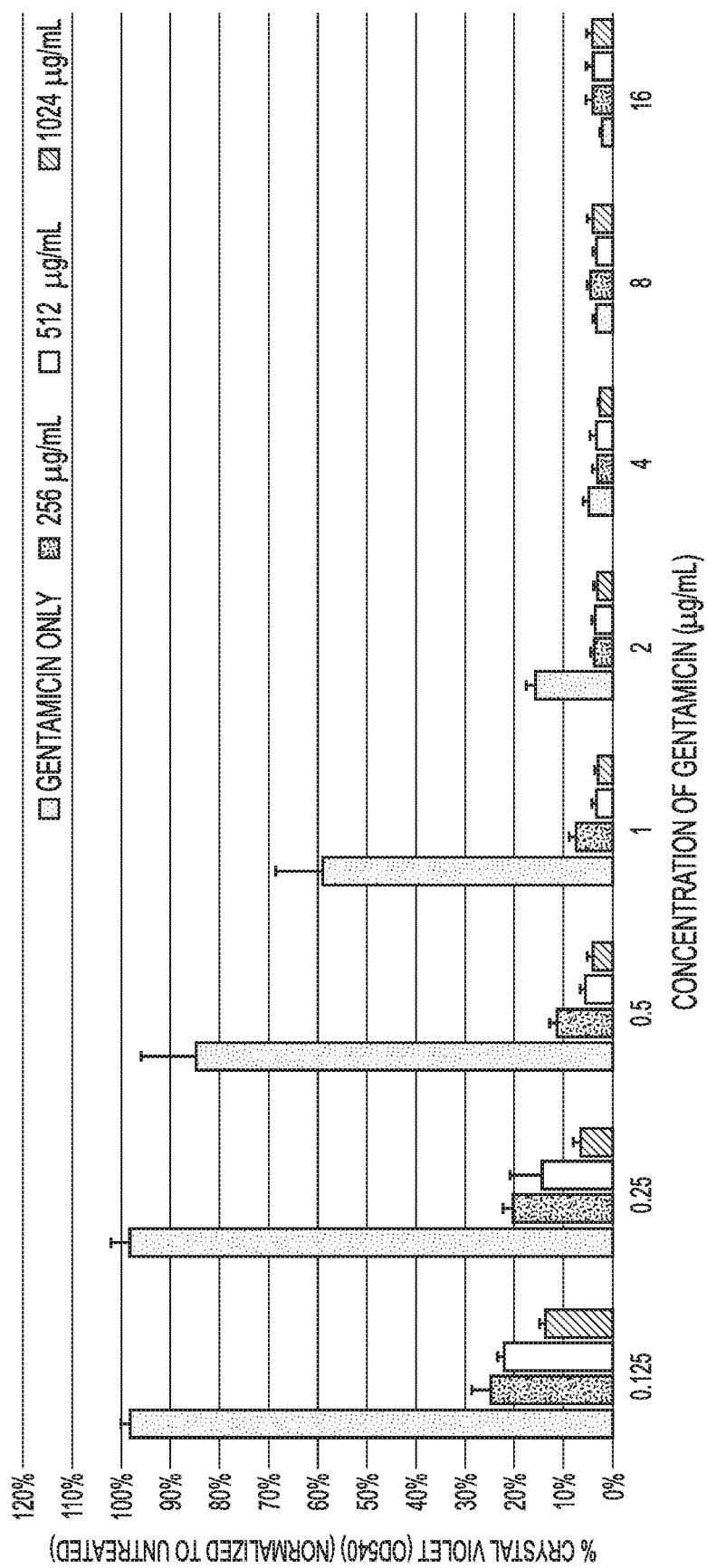

FIGS. 12A and 12B show the results from the tests for MAPCHO-10 and MAPCHO-12, respectively. The results demonstrated that either MAPCHO-10 or MAPCHO-12, when dosed in combination with gentamicin, is more effective at preventing S. aureus biofilm formation as compared to treatment with gentamicin alone.

Example 10 Phospholipids and Antibiotics Together Inhibit Growth of Planktonic Bacteria We performed in vitro studies of the capacity of phospholipids together with antibiotics to inhibit the growth of planktonic bacteria. The tests were conducted as follows. Freshly grown MRSA was quantitated and placed in 96-well plates together with gentamicin alone, phospholipids plus gentamicin, or control solutions. Two different phospholipids (MAPCHO-10 and MAPCHO-12) were tested at three different phospholipid test concentrations (256 µg/ml, 512 µg/ml, and 1024 µg/ml). After 24 hours at 37 degrees C., media was removed and fresh medium was added and the 96-well plates were incubated at 37 degrees C. for 6 hours. Bacterial density was then analyzed and measured at OD600.

Figure 13A:
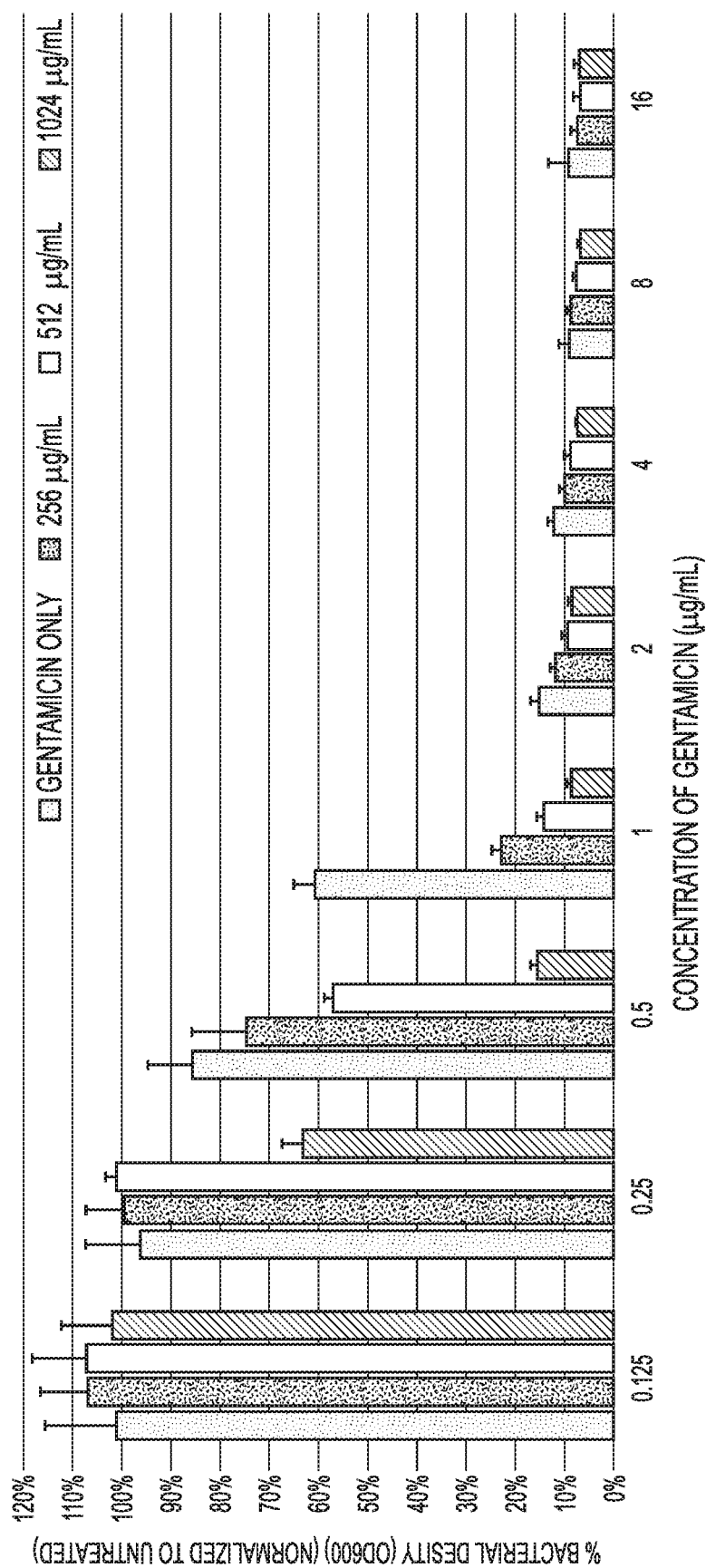
FIGS. 13A and 13B show inhibition of bacterial growth (bacteria density) of MRSA 6 h after treatment with gentamicin, either in the absence of a phospholipid, or in the presence of a phospholipid at 256, 512, or 1024 µg/ml concentrations. The phospholipids investigated are MAPCHO-10 (FIG. 13A) and MAPCHO-12 (FIG. 13B).
Figure 13B:
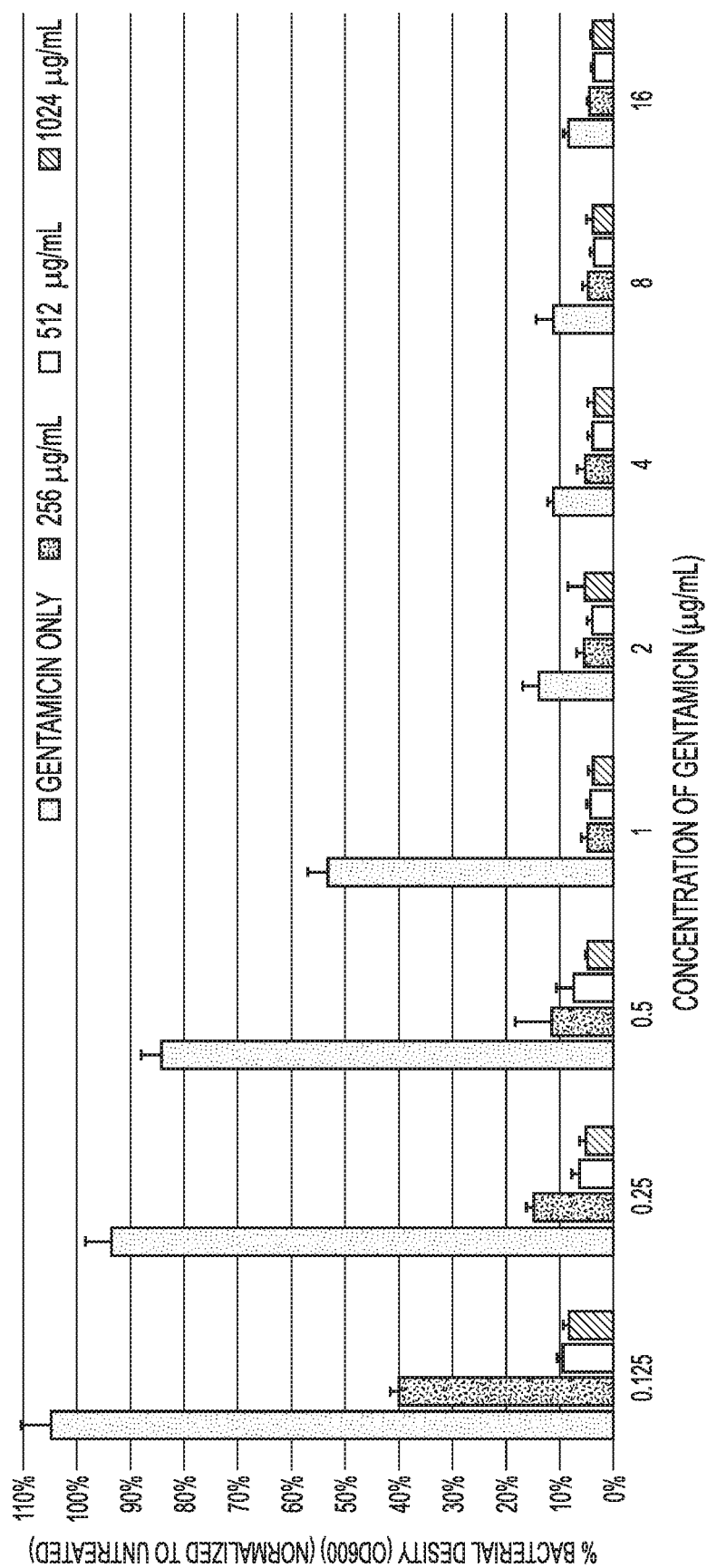

FIGS. 13A and 13B show the results from the tests for MAPCHO-10 and MAPCHO-12, respectively. The results demonstrated that moderate inhibition of MRSA growth is observed upon treatment with gentamicin in combination with MAPCHO-10 as compared to treatment with gentamicin alone (FIG. 13A), while strong inhibition of MRSA growth is observed upon treatment with gentamicin in combination with MAPCHO-12 as compared to treatment with gentamicin alone (FIG. 13B).

Example 11 Phospholipids and Antibiotics Together Prevent the Formation of Biofilms We performed in vitro tests of the capacity of phospholipids together with antibiotics to prevent formation of biofilms. Freshly grown MRSA was quantitated and placed in 96-well plates together with gentamicin alone, phospholipids plus gentamicin, or control solutions. Two different phospholipids (MAPCHO-10 and MAPCHO-12) were tested at three different phospholipid test concentrations (256 µg/ml, 512 µg/ml, and 1024 µg/ml). After 6 hours at 37 degrees C., the fluids were removed and the wells stained with crystal violet, and then the density of crystal violet in the wells was quantitated.

Figure 14A:
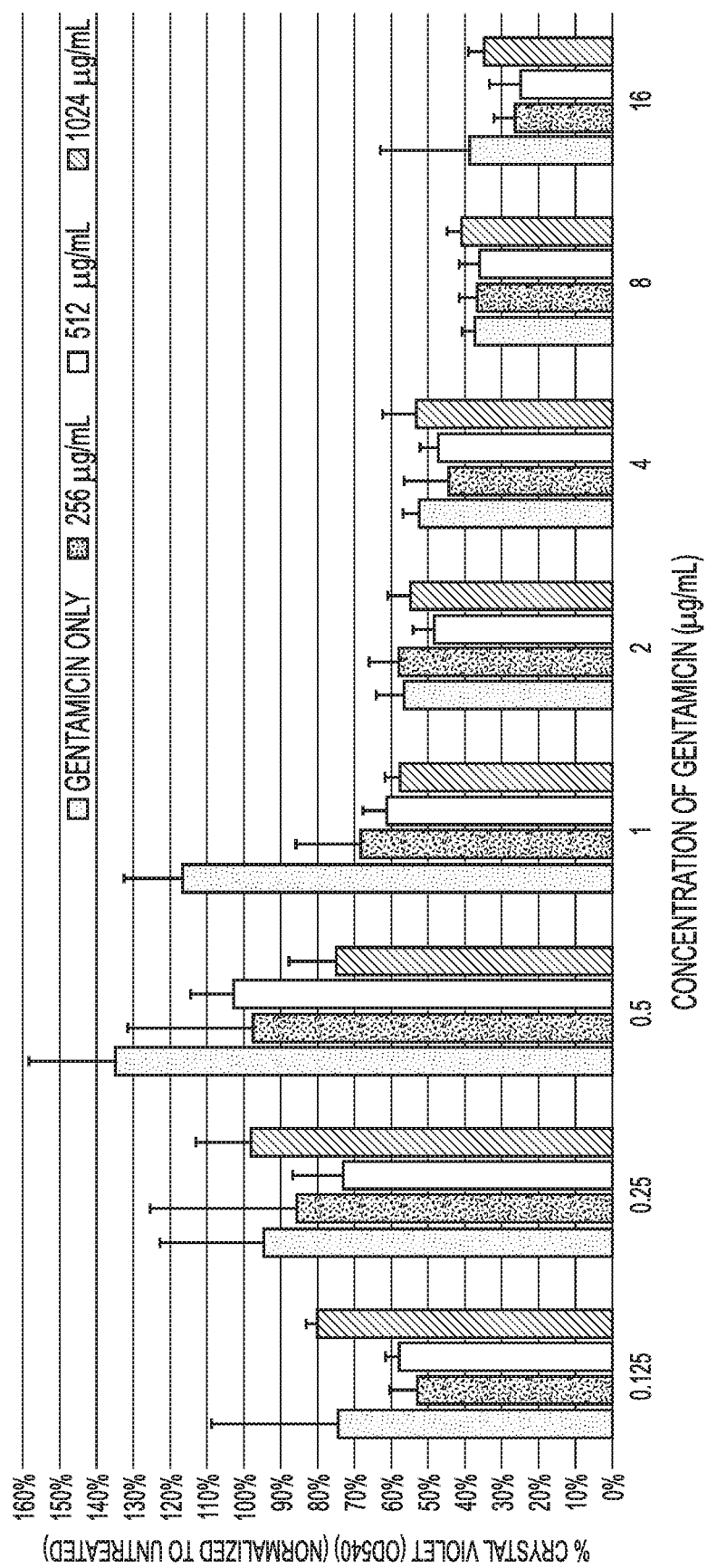
FIGS. 14A and 14B show prevention of MRSA biofilm formation 6 h after treatment with gentamicin, either in the absence of a phospholipid, or in the presence of a phospholipid at 256, 512, or 1024 µg/ml concentrations. The phospholipids investigated are MAPCHO-10 (FIG. 14A) and MAPCHO-12 (FIG. 14B).
Figure 14B:
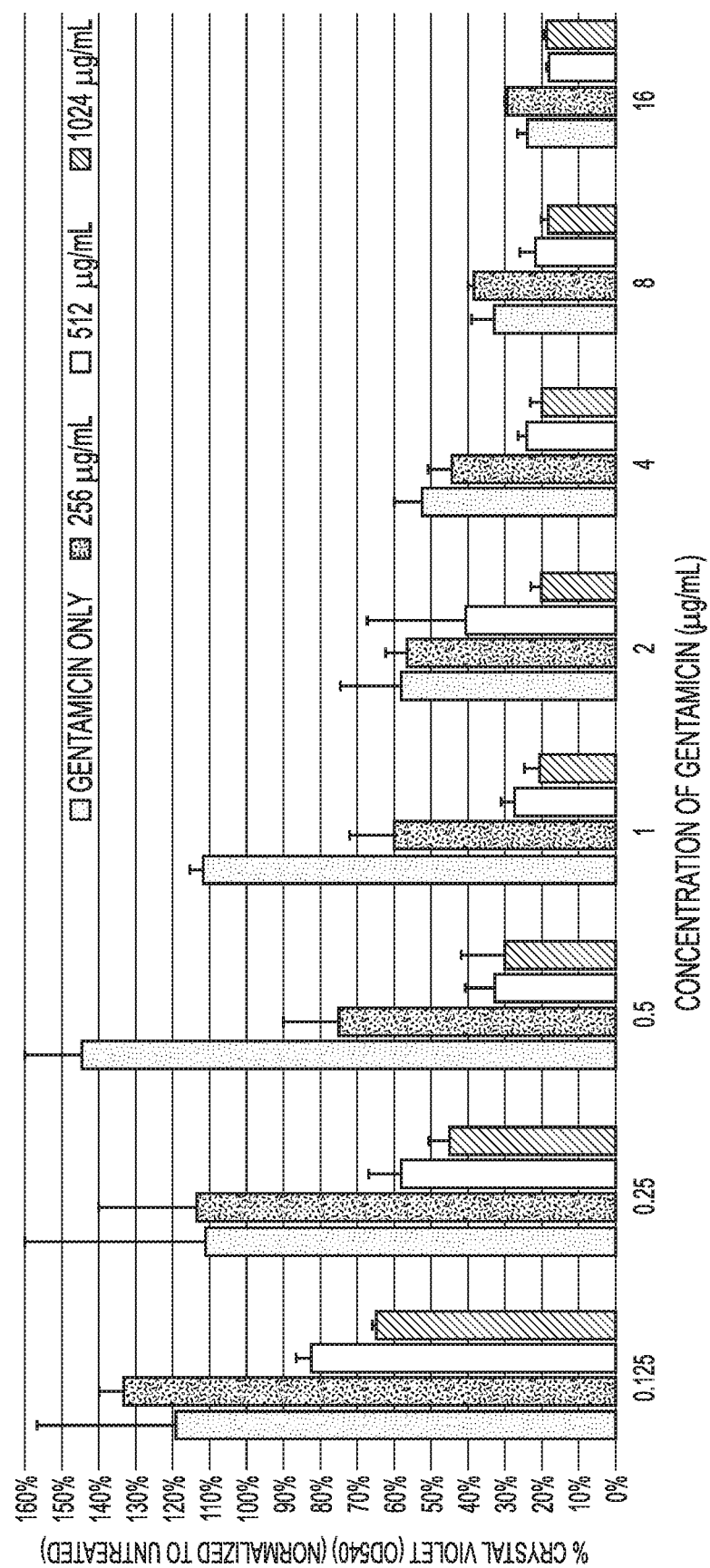

FIGS. 14A and 14B show the results from the tests for MAPCHO-10 and MAPCHO-12, respectively. The results demonstrated that MAPCHO-12, when dosed in combination with gentamicin, tends to be more effective at preventing MRSA biofilm formation as compared to treatment with gentamicin alone at the 512 µg/ml and 1024 µg/ml phospholipid test concentrations.

Example 12 Phospholipids and Antibiotics Together Inhibit Biofilm Formation

We also performed in vitro tests of the capacity of phospholipids together with antibiotics to prevent formation of biofilms. Freshly grown S. aureus (NCTC 8325) were quantitated and placed in 96-well plates together with phospholipids plus gentamicin and tobramycin (antibiotics) or antibiotics alone. After 24 hours at 37 degrees C., the fluids were removed and the wells stained with crystal violet, and then the density of crystal violet in the wells was quantitated by absorption of light at 540 nm.

Figure 15:
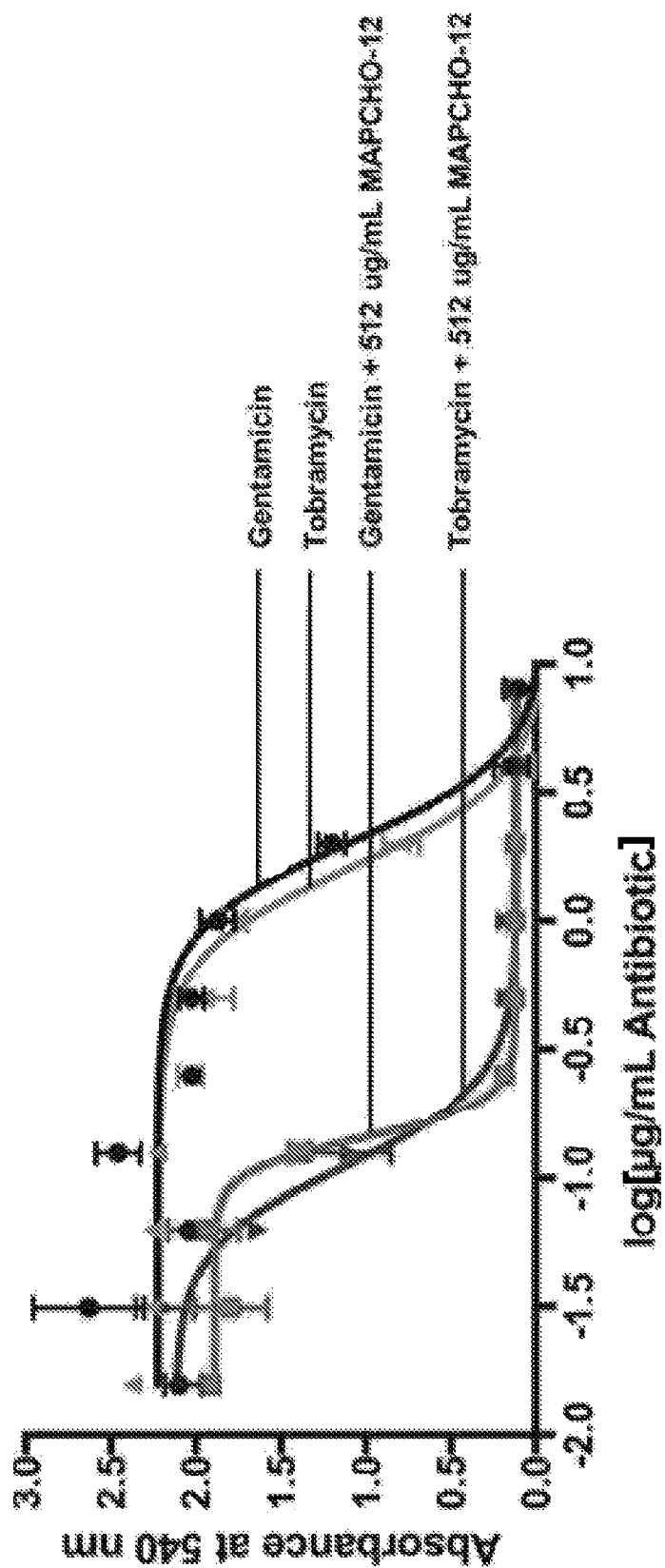
FIG. 15 shows the susceptibility of *S. aureus* (NCTC 8325) biofilm formation to either gentamicin or tobramycin treatment in the presence or absence of phospholipid MAPCHO-12.
Figure 16:
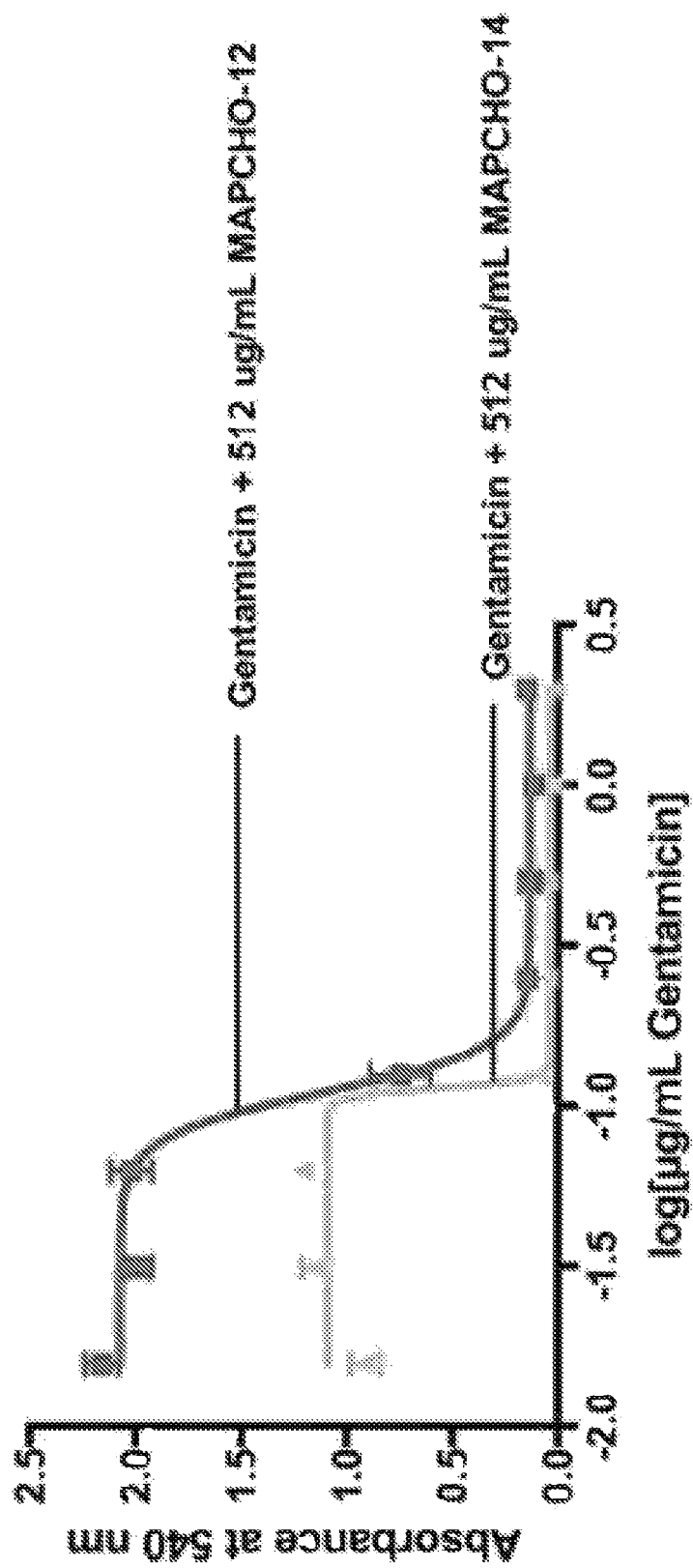
FIG. 16 shows the susceptibility of *S. aureus* (NCTC 8325) biofilm formation to gentamicin treatment in the presence of either phospholipid MAPCHO-12 or MAPCHO-14.
Figure 17:
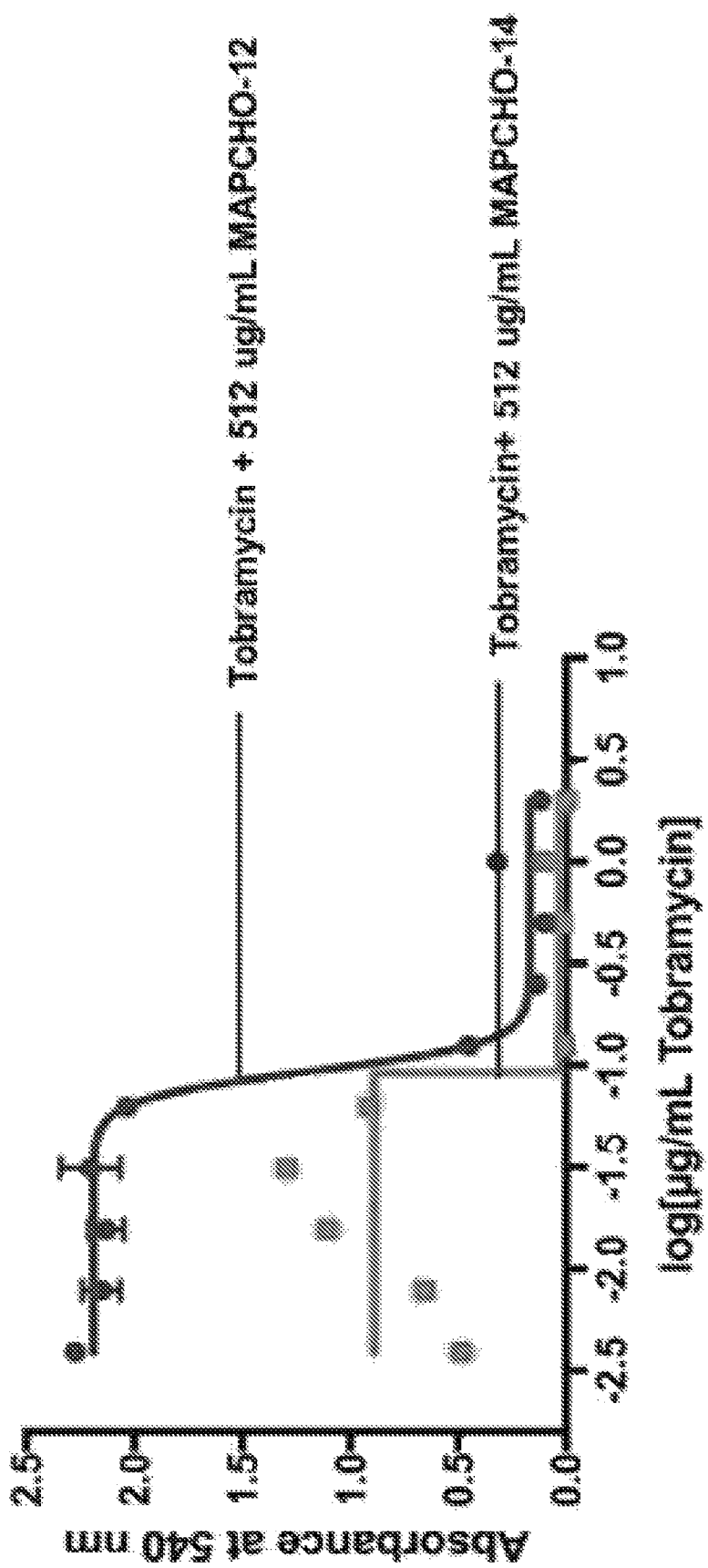
FIG. 17 shows the susceptibility of *S. aureus* (NCTC 8325) biofilm formation to tobramycin treatment in the presence of either phospholipid MAPCHO-12 or MAPCHO-14.

FIG. 15 shows the results from the tests, which demonstrated positive effects of a 512 µg dose of the phospholipid dodecylphosphocholine (MAPCHO-12) in combination with either tobramycin or gentamicin on the formation of a biofilm produced by S. aureus as compared to treatment with either tobramycin or gentamicin alone. FIGS. 16 and 17 illustrate similar positive effects of a 512 µg dose of tetradecylphosphocholine (MAPCHO-14) combined with either gentamycin or tobramycin, respectively, on the formation of biofilm produced by S. aureus.

As shown in FIG. 15, whereas treatment with either gentamicin or tobramycin alone did not prevent the formation of the biofilm by S. aureus at low antibiotic concentrations, the combination of either tobramycin or gentamicin with phospholipid MAPCHO-12 was able to prevent biofilm formation at low concentrations. The phospholipid alone also did not prevent biofilm formation (data not shown).

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. Unless otherwise indicated, the invention illustratively described herein suitably may be practiced in the absence of any element or elements, or limitation or limitations, which is not specifically disclosed herein as essential. Unless otherwise indicated, the methods and processes illustratively described herein suitably may be practiced in differing orders of steps, and that they are not necessarily restricted to the orders of steps indicated herein or in the claims.

Unless otherwise indicated, the terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method of disrupting preformed bacterial biofilm or preventing formation of biofilms by a bacterium, comprising contacting the bacterium with a therapeutically effective amount of at least one antibiotic and at least one phospholipid, thereby disrupting preformed bacterial biofilm or preventing formation of biofilms by the bacterium; wherein the at least one phospholipid is represented by formula II, or a pharmaceutically acceptable salt thereof:

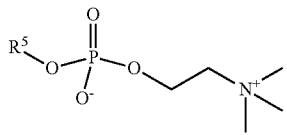

wherein:
R$^5$ is a saturated or unsaturated C$_{11}$, C$_{12}$, C$_{13}$, C$_{14}$, or C$_{15}$ alkyl chain.

2. The method of claim 1, wherein the bacterium is present in a sinonasal passage of a mammalian subject.

3. The method of claim 1, wherein the antibiotic and the phospholipid are present as a dry powder or liquid formulation.

4. The method of claim 1, wherein R$^5$ is a saturated or unsaturated C$_{12}$, C$_{13}$, or C$_{14}$ alkyl chain.

5. The method of claim 1, wherein R$^5$ is a saturated C$_{11}$, C$_{12}$, C$_{13}$, C$_{14}$, or C$_{15}$ alkyl chain.

6. The method of claim 1, wherein when R$^5$ is an unsaturated alkyl chain R$^5$ has between 1 to 3 double bonds having a cis-configuration, a trans-configuration, or a mixture of cis- and trans-configurations.

7. The method of claim 1, wherein the phospholipid and the antibiotic are present in a pharmaceutical composition.

8. The method of claim 1, wherein the phospholipid and the antibiotic are contacted with the bacterium simultaneously.

9. The method of claim 1, wherein the phospholipid is dodecylphosphocholine, or a pharmaceutically acceptable salt thereof.

10. The method of claim 1, wherein the phospholipid is tetradecylphosphocholine, or a pharmaceutically acceptable salt thereof.

11. The method of claim 1, wherein the at least one antibiotic comprises one or both of gentamicin and tobramycin.

12. A method of treating or preventing chronic rhinosinusitis (CRS), comprising administering to a subject afflicted with or at risk of developing CRS a therapeutically effective amount of at least one antibiotic and at least one phospholipid, thereby treating or preventing CRS in the subject; wherein the at least one phospholipid is represented by formula II, or a pharmaceutically acceptable salt thereof:

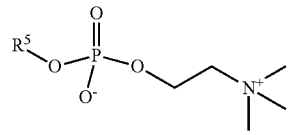

wherein:
R$^5$ is a saturated or unsaturated C$_{11}$, C$_{12}$, C$_{13}$, C$_{14}$, or C$_{15}$ alkyl chain.

13. The method of claim 12, wherein R$^5$ is a saturated or unsaturated C$_{12}$, C$_{13}$, or C$_{14}$ alkyl chain.

14. The method of claim 12, wherein R$^5$ is a saturated C$_{11}$, C$_{12}$, C$_{13}$, C$_{14}$, or C$_{15}$ alkyl chain.

15. The method of claim 12, wherein when R$^5$ is an unsaturated alkyl chain R$^5$ has between 1 to 3 double bonds having a cis-configuration, a trans-configuration, or a mixture of cis- and trans-configurations.

16. The method of claim 12, wherein the phospholipid is dodecylphosphocholine, or a pharmaceutically acceptable salt thereof.

17. The method of claim 12, wherein the phospholipid is tetradecylphosphocholine, or a pharmaceutically acceptable salt thereof.

18. The method of claim 12, wherein the phospholipid and the antibiotic are administered to the subject simultaneously.

19. The method of claim 12, wherein the phospholipid and the antibiotic are administered to the subject sequentially.

20. The method of claim 12, wherein a pharmaceutical composition comprising the phospholipid and the antibiotic are administered through a nasal sinus of the subject.

21. The method of claim 20, wherein the pharmaceutical composition is a dry composition, an aerosolized composition or a liquid composition.

22. The method of claim 20, wherein the pharmaceutical composition is administered to the subject via an inhaler, a syringe device, an aerosol device or a nebulizer.

23. The method of claim 20, wherein the pharmaceutical composition is administered to the subject in combination with a steroid or an antifungal compound.

24. The method of claim 12, further comprising examining the subject for improved sinus symptoms, a lowered volume of nasal fluid or post-nasal drip, a partial or complete removal of biofilm in a sinus, or a decreased appearance of inflammation in the sinus.

25. A therapeutic kit or pharmaceutical composition for treating or preventing chronic rhinosinusitis (CRS), comprising at least one antibiotic and at least one phospholipid, wherein the phospholipid is represented by formula II, or a pharmaceutically acceptable salt thereof:

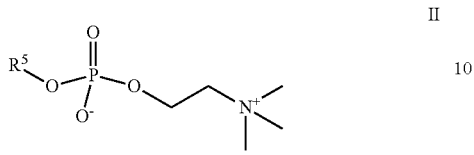

wherein:
$R^5$ is a saturated or unsaturated $C_{11}$, $C_{12}$, $C_{13}$, $C_{14}$, or $C_{15}$ alkyl chain.

26. The kit or composition of claim 25, wherein the at least one phospholipid is dodecylphosphocholine, or a pharmaceutically acceptable salt thereof, or tetradecylphosphocholine, or a pharmaceutically acceptable salt thereof, and the at least one antibiotic comprises one or both of gentamicin and tobramycin.

27. The kit or composition of claim 25, wherein $R^5$ is a saturated $C_{11}$, $C_{12}$, $C_{13}$, $C_{14}$, or $C_{15}$ alkyl chain.

28. The kit or composition of claim 25, wherein $R^5$ is a saturated or unsaturated $C_{12}$, $C_{13}$, or $C_{14}$ alkyl chain.

* * * * *